United States Patent
Dominguez-Bendala et al.

(10) Patent No.: US 11,466,255 B2
(45) Date of Patent: Oct. 11, 2022

(54) METHODS AND COMPOSITIONS FOR CONVERTING NON-ENDOCRINE PANCREATIC TISSUE INTO INSULIN-PRODUCING CELLS

(71) Applicants: Juan Dominguez-Bendala, Miramar, FL (US); Luca Inverardi, Miami Beach, FL (US); Ricardo L. Pastori, Doral, FL (US); Camillo Ricordi, Miami, FL (US)

(72) Inventors: Juan Dominguez-Bendala, Miramar, FL (US); Luca Inverardi, Miami Beach, FL (US); Ricardo L. Pastori, Doral, FL (US); Camillo Ricordi, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 1095 days.

(21) Appl. No.: 15/573,870

(22) PCT Filed: May 2, 2016

(86) PCT No.: PCT/US2016/030442
§ 371 (c)(1),
(2) Date: Nov. 14, 2017

(87) PCT Pub. No.: WO2016/179106
PCT Pub. Date: Nov. 10, 2016

(65) Prior Publication Data
US 2018/0155692 A1   Jun. 7, 2018

Related U.S. Application Data

(60) Provisional application No. 62/155,665, filed on May 1, 2015.

(51) Int. Cl.
| | |
|---|---|
| *A61K 38/18* | (2006.01) |
| *A61P 5/50* | (2006.01) |
| *A61P 3/10* | (2006.01) |
| *C12N 5/071* | (2010.01) |
| *A61K 48/00* | (2006.01) |
| *A61K 35/39* | (2015.01) |

(52) U.S. Cl.
CPC ............ *C12N 5/0676* (2013.01); *A61K 35/39* (2013.01); *A61K 38/1875* (2013.01); *A61K 48/00* (2013.01); *A61P 3/10* (2018.01); *A61P 5/50* (2018.01); *C12N 2501/155* (2013.01)

(58) Field of Classification Search
CPC .......... A61K 38/1875; A61P 5/50; A61P 3/10
See application file for complete search history.

(56) References Cited

U.S. PATENT DOCUMENTS

| | | | |
|---|---|---|---|
| 2002/0072115 A1 | 6/2002 | Harrison et al. | |
| 2007/0155661 A1* | 7/2007 | Kim ................... | A61K 38/1875 424/93.1 |
| 2011/0033930 A1 | 2/2011 | Scharfmann et al. | |
| 2011/0047633 A1 | 2/2011 | Vukicevic et al. | |
| 2012/0135927 A1* | 5/2012 | Tseng ....................... | A61P 3/10 514/8.8 |
| 2013/0122586 A1* | 5/2013 | Kanamune ........... | C12N 5/0676 435/354 |
| 2014/0057831 A1 | 2/2014 | Bosukonda et al. | |

FOREIGN PATENT DOCUMENTS

WO   WO-2004/113512 A2   12/2004

OTHER PUBLICATIONS

Gomez-Puerto et al., J. Pathol., 2019, vol. 247:9-20.*
Chen et al., Development, 2004, vol. 131:2219-2231.*
Jiramongkolchai et al., Biochem. Soc. Trans., 2016, vol. 44(4):1117-1134.*
Daneman, D., Lancet, 2006, vol. 367:847-858.*
Sugimoto et al., Nat. Med., 2012, vol. 18(3):396-404.*
Afrikanova et al., Is stage-specific embryonic antigen 4 a marker for human ductal stem/progenitor cells?, Biores. Open Access, 1(4):184-91 (2012).

(Continued)

*Primary Examiner* — Xiaozhen Xie
(74) *Attorney, Agent, or Firm* — Marshall, Gerstein & Borun LLP

(57) ABSTRACT

Compositions and methods are provided for generating islet-like cell clusters. The methods include culturing a whole non-islet pancreatic cell discard or cells sorted therefrom with an effective amount of a molecule having Bone Morphogenetic Protein (BMP) activity (e.g., a BMP polypeptide). The effective amount of said molecule having BMP activity (e.g., BMP polypeptide) is sufficient to induce the formation of islet-like cell clusters. The methods further include treating or attenuating insulin-deficiency disorders, including type 1 diabetes. In one non-limiting embodiment, an insulin-deficiency disorder in a subject is treated or attenuated by culturing a whole non-islet pancreatic cell discard or cells sorted therefrom with an effective amount of a molecule having BMP activity (e.g., a BMP polypeptide) such that tho formation of islet-like cell clusters occurs. A therapeutically effective amount of the islet-like cell clusters which produce insulin are then transplanted into a subject in need to treat the insulin-deficiency disorder.

8 Claims, 21 Drawing Sheets
Specification includes a Sequence Listing.

(56) References Cited

OTHER PUBLICATIONS

Ahlgren et al., Beta-cell-specific inactivation of the mouse Ipf1/Pdx1 gene results in loss of the beta-cell phenotype and maturity onset diabetes, Genes Dev., 12(12):1763-8 (1998).
Baeyens et al., Can beta-cells be derived from exocrine pancreas?, Diabetes Obes. Metab., 10 Suppl 4:170-8 (2008).
Baeyens et al., Transient cytokine treatment induces acinar cell reprogramming and regenerates functional beta cell mass in diabetic mice, Nat. Biotechnol., 32(1):76-83 (2014).
Bellin et al., Prolonged insulin independence after islet allotransplants in recipients with type 1 diabetes, Am. J. Transplant., 8(11):2463-70 (2008).
Bonner-Weir et al., A second pathway for regeneration of adult exocrine and endocrine pancreas. A possible recapitulation of embryonic development, Diabetes, 42(12):1715-20 (1993).
Bonner-Weir et al., In vitro cultivation of human islets from expanded ductal tissue, Proc. Natl. Acad. Sci. USA, 97(14):7999-8004 (2000).
Bonner-Weir et al., The pancreatic ductal epithelium serves as a potential pool of progenitor cells, Pediatr. Diabetes, 5 Suppl 2:16-22 (2004).
Bonner-Weir et al., Transdifferentiation of pancreatic ductal cells to endocrine beta-cells, Biochem. Soc. Trans., 36(Pt. 3):353-6 (2008).
Bravo-Egana et al., Quantitative differential expression analysis reveals miR-7 as major islet microRNA, Biochem. Biophys. Res. Commun., 366(4):922-6 (2008).
Bruun et al., Inhibition of beta cell growth and function by bone morphogenetic proteins, Diabetologia, 57(12):2546-54 (2014).
Buchwald et al., Feasibility of localized immunosuppression: 1. Exploratory studies with glucocorticoids in a biohybrid device designed for cell transplantation, Pharmazie, 65(6):421-8 (2010).
Cardinale et al., Multipotent stem/progenitor cells in human biliary tree give rise to hepatocytes, cholangiocytes, and pancreatic islets, Hepatology, 54(6):2159-72 (2011).
Cardinale et al., The biliary tree—a reservoir of multipotent stem cells, Nat. Rev. Gastroenterol. Hepatol., 9(4):231-40 (2012).
Cavelti-Weder et al., Hyperglycaemia attenuates in vivo reprogramming of pancreatic exocrine cells to beta cells in mice, Diabetologia, 59(3):522-32 (2016).
Cechin et al., Influence of in vitro and in vivo oxygen modulation on B cell differentiation from human embryonic stem cells, Stem Cells Transl. Med., 3(3):277-89 (2014).
Cheifetz et al., Influence of osteogenic protein-1 (OP-1;BMP-7) and transforming growth factor-beta 1 on bone formation in vitro, Connect. Tissue Res., 35(1-4):71-8 (1996).
Chen et al., Signal transduction and biological functions of bone morphogenetic proteins, Front Biosci., 9:349-58 (2004).
Chung et al., Suppression of Alk8-mediated Bmp signaling cell-autonomously induces pancreatic beta-cells in zebrafish, Proc. Natl. Acad. Sci. USA, 107(3):1142-7 (2010).
Corradini et al., BMP6 treatment compensates for the molecular defect and ameliorates hemochromatosis in Hfe knockout mice, Gastroenterology, 139(5):1721-9 (2010).
Corritore et al., β-Cell differentiation of human pancreatic duct-derived cells after in vitro expansion, Cell Reprogram., 16(6):456-66 (2014).
D'Amour et al., Production of pancreatic hormone-expressing endocrine cells from human embryonic stem cells, Nat. Biotechnol., 24(11):1392-401 (2006).
Dominguez-Bendala et al., Intracardial embryonic delivery of developmental modifiers in utero, Cold Spring Harb. Protoc., 2012(9):962-8 (2012).
Dominguez-Bendala et al., MicroRNA-7 control of β-cell replication, Diabetes, 62(3):694-5 (2013).
Dominguez-Bendala et al., TAT-mediated neurogenin 3 protein transduction stimulates pancreatic endocrine differentiation in vitro, Diabetes, 54(3):720-6 (2005).
Dominguez-Bendala et al., The Human Endocrine Pancreas: New Insights on Replacement and Regeneration, Trends Endocrinol. Metab., 27(3):153-62 (2016).
Edlund, Developmental biology of the pancreas, Diabetes, 50 Suppl 1:S5-9 (2001).
Edlund, Pancreatic organogenesis—developmental mechanisms and implications for therapy, Nat. Rev. Genet., 3(7):524-32 (2002).
Edlund, Transcribing pancreas, Diabetes, 47(12):1817-23 (1998).
Fritsche et al., Relationships among age, proinsulin conversion, and beta-cell function in nondiabetic humans, Diabetes, 51 Suppl 1:S234-9 (2002).
Furuyama et al., Continuous cell supply from a Sox9-expressing progenitor zone in adult liver, exocrine pancreas and intestine, Nat. Genet., 43(1):34-41 (2011).
Gannon et al., Regulatory regions driving developmental and tissue-specific expression of the essential pancreatic gene pdx1, Dev. Biol., 238(1):185-201 (2001).
Gannon, BuMP-ing up insulin secretion by pancreatic beta cells, Cell Metab., 5(3):157-9 (2007).
Goulley et al., BMP4-BMPR1A signaling in beta cells is required for and augments glucose-stimulated insulin secretion, Cell Metab., 5(3):207-19 (2007).
Gu et al., Direct lineage tracing reveals the ontogeny of pancreatic cell fates during mouse embryogenesis, Mech. Dev., 120(1):35-43 (2003).
Hammer et al., The rat elastase I regulatory element is an enhancer that directs correct cell specificity and developmental onset of expression in transgenic mice, Mol. Cell Biol., 7(8):2956-67 (1987).
Herrera et al., A rapid and sensitive bioassay for the simultaneous measurement of multiple bone morphogenetic proteins. Identification and quantification of BMP4, BMP6 and BMP9 in bovine and human serum, BMC Cell Biol., 10:20 (2009).
Hrvatin et al., MARIS: method for analyzing RNA following intracellular sorting, PLoS One, 9(3):e89459 (2014).
Hunter et al., Phase 1 safety and tolerability study of BMP-7 in symptomatic knee osteoarthritis, BMC Musculoskelet. Disord., 11:232 (2010).
Inada et al., Timing and expression pattern of carbonic anhydrase II in pancreas, Dev. Dyn., 235(6):1571-7 (2006).
International Application No. PCT/US16/30442, International Preliminary Report on Patentability, dated Nov. 7, 2017.
International Application No. PCT/US16/30442, International Search Report and Written Opinion, dated Sep. 23, 2016.
Jiang et al., Bone morphogenetic proteins promote development of fetal pancreas epithelial colonies containing insulin-positive cells, J. Cell Sci., 115(Pt. 4):753-60 (2002).
Jin et al., Cells with surface expression of CD133highCD71low are enriched for tripotent colony-forming progenitor cells in the adult murine pancreas, Stem Cell Res., 16(1):40-53 (2016).
Jin et al., Colony-forming cells in the adult mouse pancreas are expandable in Matrigel and form endocrine/acinar colonies in laminin hydrogel, Proc. Natl. Acad. Sci. USA, 110(10):3907-12 (2013).
Kawaguchi, Sox9 and programming of liver and pancreatic progenitors, J. Clin. Invest., 123(5):1881-6 (2013).
Kayton et al., Human islet preparations distributed for research exhibit a variety of insulin-secretory profiles, Am. J. Physiol. Endocrinol. Metab., 308(7):E592-602 (2015).
Kim et al., A draft map of the human proteome, Nature, 509(7502):575-80 (2014).
Klein et al., BMP-7 Induces Adult Human Pancreatic Exocrine-to-Endocrine Conversion, Diabetes, 64(12):4123-34 (2015).
Klein et al., MicroRNA expression in alpha and beta cells of human pancreatic islets, PLoS One, 8(1):e55064 (2013).
Kopp et al., Sox9+ ductal cells are multipotent progenitors throughout development but do not produce new endocrine cells in the normal or injured adult pancreas, Development, 138(4):653-65 (2011).
Kubota et al., Clonogenic hepatoblasts, common precursors for hepatocytic and biliary lineages, are lacking classical major histocompatibility complex class I antigen, Proc. Natl. Acad. Sci. USA, 97(22):12132-7 (2000).

(56) References Cited

OTHER PUBLICATIONS

Kuo et al., BMP-9 as a potent brown adipogenic inducer with anti-obesity capacity, Biomaterials, 35(10):3172-9 (2014).
Larsson et al., Relative hyperproinsulinemia as a sign of islet dysfunction in women with impaired glucose tolerance, J. Clin. ENdocrinol. Metab., 84(6):2068-74 (1999).
Lee et al., Expansion and conversion of human pancreatic ductal cells into insulin-secreting endocrine cells, eLife, 2:e00940 (2013).
Lemper et al., Reprogramming of human pancreatic exocrine cells to β-like cells, Cell Death Differ., 22(7):1117-30 (2015).
Li et al., In vivo reprogramming of pancreatic acinar cells to three islet endocrine subtypes, eLife, 3:e01846 (2014).
Lima et al., Suppression of epithelial-to-mesenchymal transitioning enhances ex vivo reprogramming of human exocrine pancreatic tissue toward functional insulin-producing β-like cells, Diabetes, 62(8):2821-33 (2013).
Loganathan et al., Insulin degradation by acinar cell proteases creates a dysfunctional environment for human islets before/after transplantation: benefits of β-1 antitrypsin treatment, Transplantation, 92(11):1222-30 (2011).
Léon et al., The P2Y(1) receptor is involved in the maintenance of glucose homeostasis and in insulin secretion in mice, Purinergic Signal, 192):145-51 (2005).
Maric et al., BMP signaling in rats with TNBS-induced colitis following BMP7 therapy, Am. J. Physiol. Gastrointest. Liver Physiol., 302(10):G1151-62 (2012).
Miyazono et al., BMP receptor signaling: transcriptional targets, regulation of signals, and signaling cross-talk, Cytokine Growth Factor Rev., 1693):251-63 (2005).
Nieto et al., Antisense miR-7 impairs insulin expression in developing pancreas and in cultured pancreatic buds, Cell Transplant, 21(8):1761-74 (2012).
Pagliuca et al., Generation of functional human pancreatic β cells in vitro, Cell, 159(2):428-39 (2014).
Pedraza et al., Macroporous three-dimensional PDMS scaffolds for extrahepatic islet transplantation, Cell Transplant, 22(7):1123-35 (2013).
Pileggi et al., Heme oxygenase-1 induction in islet cells results in protection from apoptosis and improved in vivo function after transplantation, Diabetes, 50(9):1983-91 (2001).
Pileggi et al., MicroRNAs in islet immunobiology and transplantation, Immunol. Res., 57(1-3):185-96 (2013).
Pileggi et al., Reversal of diabetes by pancreatic islet transplantation into a subcutaneous, neovascularized device, Transplantation, 81(9):1318-24 (2006).
Poggioli et al., Quality of life after islet transplantation, Am. J. Transplant., 6(2):371-8 (2006).
Rezania et al., Reversal of diabetes with insulin-producing cells derived in vitro from human pluripotent stem cells, Nat. Biotechnol., 32(11):1121-33 (2014).
Ricordi et al., Automated method for isolation of human pancreatic islets, Diabetes, 37(4):413-20 (1988).
Ricordi et al., Clinical islet transplantation: advances and immunological challenges, Nat. Rev. Immunol., 4(4):259-68 (2004).
Rocher et al., SMAD-PI3K-Akt-mTOR pathway mediates BMP-7 polarization of monocytes into M2 macrophages, PLoS One, 8(12):e84009 (2013).
Roder et al., Disproportionately elevated proinsulin levels reflect the degree of impaired B cell secretory capacity in patients with noninsulin-dependent diabetes mellitus, J. Clin. Endocrinol. Metab., 83(2):604-8 (1998).
Rose et al., Evolutionary silencing of the human elastase I gene (ELA1), Hum. Mol. Genet., 6(6):897-903(1997).
Russ et al., In vitro proliferation of cells derived from adult human beta-cells revealed by cell-lineage tracing, Diabetes, 57(6):1575-83 (2008).
Seaberg et al., Clonal identification of multipotent precursors from adult mouse pancreas that generate neural and pancreatic lineages, Nat. Biotechnol., 22(9):1115-24 (2004).
Shapiro et al., Islet transplantation in seven patients with type 1 diabetes mellitus using a glucocorticoid-free immunosuppressive regimen, N. Engl. J. Med., 343(4):230-8 (2000).
Singh, Stem cells and other innovative intra-articular therapies for osteoarthritis: what does the future hold?, BMC Med., 10:44 (2012).
Smukler et al., The adult mouse and human pancreas contain rare multipotent stem cells that express insulin, Cell Stem Cell, 8(3):281-93 (2011).
Song et al., Feasibility of localized immunosuppression: 3. Preliminary evaluation of organosilicone constructs designed for sustained drug release in a cell transplant environment using dexamethasone, Pharmazie, 67(5):394-9 (2012).
Sugimoto et al., Activin-like kinase 3 is important for kidney regeneration and reversal of fibrosis, Nat. Med., 18(3):396-404 (2012).
Sugimoto et al., BMP-7 functions as a novel hormone to facilitate liver regeneration, FASEB J., 21(1):256-64 (2007).
Sui et al., Role of BMP signaling in pancreatic progenitor differentiation from human embryonic stem cells, Stem Cell Rev., 9(5):569-77 (2013).
Szabat et al., Kinetics and genomic profiling of adult human and mouse β-cell maturation, Islets, 3(4):175-87 (2011).
Szabat et al., Maturation of adult beta-cells revealed using a Pdx1/insulin dual-reporter lentivirus, Endocrinology, 150(4):1627-35 (2009).
Taichai et al., Pancreatic β cell dedifferentiation as a mechanism of diabetic β cell failure, Cell, 150(6):1223-34 (2012).
Ten Dijke et al., Identification of type I receptors for osteogenic protein-1 and bone morphogenetic protein-4, J. Biol. Chem., 269(25):16985-8 (1994).
Urbina et al., BMP-7 attenuates adverse cardiac remodeling mediated through M2 macrophages in prediabetic cardiomyopathy, Am. J. Physiol. Heart Circ. Physiol., 307(5):H762-72 (2014).
Vargas et al., TAT-mediated transduction of MafA protein in utero results in enhanced pancreatic insulin expression and changes in islet morphology, PLoS One, 6(8):e22364 (2011).
Wandzioch et al., Dynamic signaling network for the specification of embryonic pancreas and liver progenitors, Science, 324(5935):1707-10 (2009).
Wang et al., Biliary tree stem cells, precursors to pancreatic committed progenitors: evidence for possible life-long pancreatic organogenesis, Stem Cells, 31(9):1966-79 (2013).
Xiao et al., Concise Review: New Insights Into the Role of Macrophages in β-Cell Proliferation, Stem Cells Transl. Med., 4(6):655-8 (2015).
Yasmin et al., Identification of bone morphogenetic protein 7 (BMP7) as an instructive factor for human epidermal Langerhans cell differentiation, J. Exp. Med., 210(12):2597-610 (2013).
Yatoh et al., Differentiation of affinity-purified human pancreatic duct cells to beta-cells, Diabetes, 56(7):1802-9 (2007).
Zeisberg et al., BMP-7 counteracts TGF-beta1-induced epithelial-to-mesenchymal transition and reverses chronic renal injury, Nat. Med., 9(7):964-8 (2003).
Zhou et al., In vivo reprogramming of adult pancreatic exocrine cells to beta-cells, Nature, 455(7213):627-32 (2008).
Todorov et al., Generation of human islets through expanson and differentiation of non-islet pancreatic cells discarded (Pancreatic discard) after islet isolation, Pancreas, 32(2): 130-8 (2006).
Dichman et al., Expresson and misexpression of members of the FGF and TGFbeta families of growth factors in the developing mouse pancreas, Dev. Dynam., 226(4): 663-74 (2003).

* cited by examiner

| PREPS | DAY 0 | (CTRL) | (BMP-7) | (BMP-7 + DM) |
|---|---|---|---|---|
| 1 | 0.32 | 6.1 | 64.7 | n.d. |
| 2 | 0.3 | 4.86 | 15.41 | n.d. |
| 3 | 0.3 | 14.8 | 46.6 | n.d. |
| 4 | 1.6 | 9 | 21 | n.d. |
| 5 | 0.15 | 5.9 | 19.89 | n.d. |
| 6 | 0.1 | 7.3 | 23.5 | n.d. |
| 7 | 0.1 | 18.1 | 75.5 | 19.5 |
| 8 | 0.5 | 5.0 | 51.7 | 24.8 | p=0.0078

Figure 4
a
| Rinal prep & mouse ID | POD | pM 0 min | pM 60 min | POD | pM 0 min | pM 60 min |
|---|---|---|---|---|---|---|
| HP 2120 (Control) #609 | 39 | 0 | 0 | 122 | 0 | 0 |
| HP 2120 (BMP7+) #611 | | 0 | 57.36 | | 1.68 | 10.8 |
| HP 2120 (BMP7+) #612 | | 7.4 | 42.41 | | 0.42 | 68.33 |
| HP 2120 (BMP7+) #615 | | 0 | 230.12 | | 0 | 14.53 |
| HP 2120 (BMP7+) #616 | | 0 | 100.14 | | 0 | 0 |
| HP 2121 (Control) #595 | 31 | 0 | 0 | 114 | 0 | 0 |
| HP 2121 (BMP7+) #598 | | 6.16 | 27.03 | | 0 | 1.74 |
| HP 2121 (BMP7+) #614 | | 8.61 | 132.24 | | 0 | 0 |
| HP 2121 (BMP7+) #617 | | 0 | 0 | | 0 | 12.76 |
| HP 2121 (BMP7+) #618 | | 0 | 0 | | 3.26 | 65.99 |
| HP 2122 (Control) #251 | 25 | 0 | 0 | 108 | 0 | 0 |
| HP 2122 (BMP7+) #249 | | 17.93 | 212.42 | | 0 | 57.67 |
| HP 2122 (BMP7+) #480 | | 12.25 | 28.82 | | Died | Died |
| HP 2122 (BMP7+) #489 | | 0 | 37.88 | | 0 | 0 |
| HP 2122 (BMP7+) #491 | | 17.87 | 77.54 | | Died | Died |
| Sham/Saline #701 | 25 | 0 | 0 | 108 | 0 | 0 |
| Sham/Saline #702 | | 0 | 0 | | Died | Died |
| Sham/Saline #703 | | 0 | 0 | | 0 | 0 |
| Sham/Saline #704 | | 0 | 0 | | 0 | 0 |
| Sham/Saline #705 | | 0 | 0 | | 0 | 0 |
b
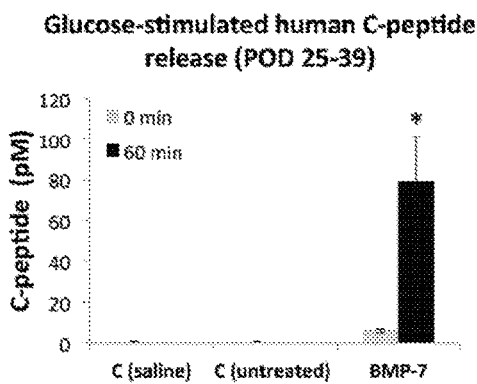
c
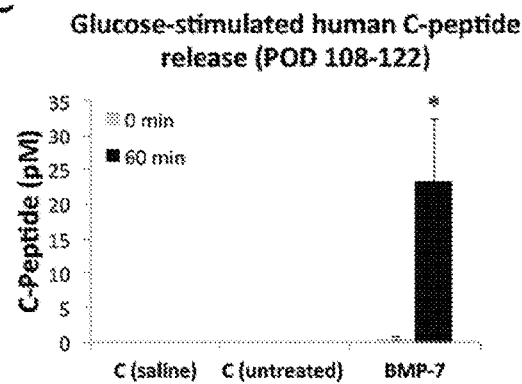

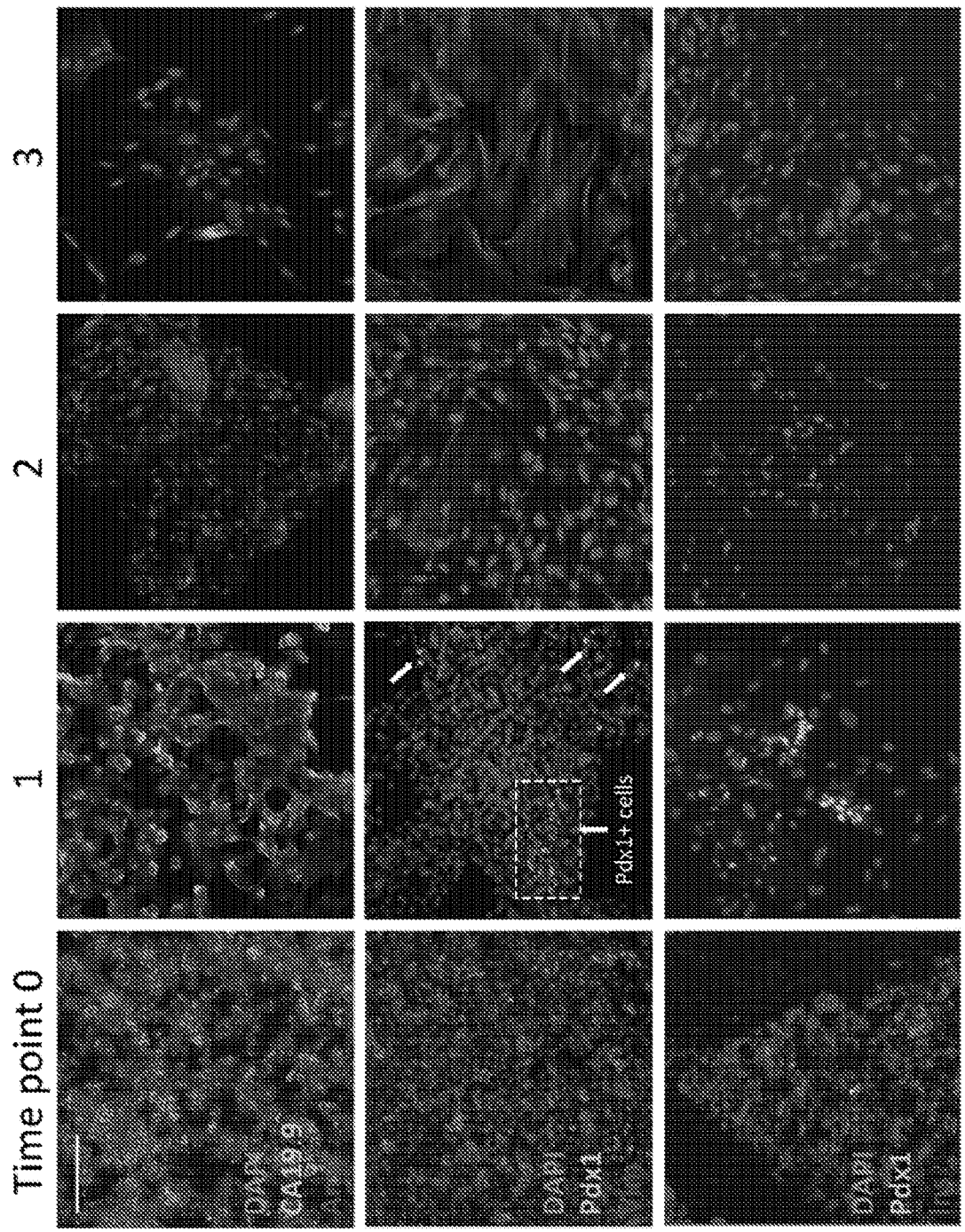

| b | Count | % of total | % of PDX1+ cells | % of PDX1+/ALK3+ cells |
|---|---|---|---|---|
| DAPI nuclei in tile | 48,189 | 100 | ~ | ~ |
| PDX1+ cells | 11,139 | 23.12 | 100 | ~ |
| PDX1+/CAII+ | 8,935 | 18.54 | 80.21 | ~ |
| PDX1+/ALK3+ | 2,094 | 4.34 | 18.8 | 100 |
| PDX1+/ALK3+/CAII+ | 2,048 | 4.24 | 18.39 | 97.8 |
| PDX1+/ALK3+/CAII- | 46 | 0.09 | 0.41 | 2.2 |

Figure 13

| Name | Host | Source/ cat. number | Dilution/ Conc. |
|---|---|---|---|
| Amylase 2B | Mouse | SantaCruz (sc-46657) | 1:200 |
| a-Amylase | Rabbit | Sigma (A8273) | 1:200 |
| Cytokeratin 19 | Mouse | Dako (M0888) | 1:100 |
| CA19-9 | Mouse | Leica (NCL-L-CA19-9) | 1:100 |
| Mucin-6 | Mouse | Leica (NCL-L-MUC-6) | 1:100 |
| PDX1 | Goat | R&D systems (AF2419) | 15 µg/mL |
| NKX6.1 | Mouse | DSHB (F55A12-s) | 2 µg/mL |
| MafA | Mouse | Abcam (ab57807) | 1:100 |
| Insulin | Guinea pig | Dako (A0564) | 1:250 |
| C-peptide | Mouse | Chemicon (CBL94) | 1:100 |
| Anti-proinsulin C-peptide clone CPEP-01 | Mouse | Millipore 05-1109 | 1:25 |
| Glucagon | Rabbit | Biogenex (PU039-UP) | 1:200 |
| Glucagon | Rabbit | Dako (A0565) | 1:250 |
| Pancreatic Polypeptide | Rabbit | Chemicon (AB939) | 1:200 |
| Somatostatin | Rabbit | Dako (A0566) | 1:200 |
| Vimentin | Rabbit | GeneTex (GTX100619) | 1:500 |
| GFP | Chicken | Aves GFP-1020 | 1:500 |
| BMPR1A (ALK3) | Mouse | Life Span Biosciences (LS-C191759/58348) | 1:50 |
| SOX9 | Rabbit | Millipore (AB5535) | 1:100 |

METHODS AND COMPOSITIONS FOR CONVERTING NON-ENDOCRINE PANCREATIC TISSUE INTO INSULIN-PRODUCING CELLS

CROSS-REFERENCE TO RELATED APPLICATIONS

The present application is the U.S. National Phase of PCT/US2016/030442, filed May 2, 2016, which claims the benefit of priority to U.S. Provisional Application No. 62/155,665, filed May 1, 2015, the disclosures of which are incorporated herein by reference in their entireties.

FIELD OF THE INVENTION

The invention relates generally to compositions and methods for the conversion of human non-endocrine pancreatic tissue (NEPT) into insulin-producing cells by exposure of primary exocrine tissue to a molecule having bone morphogenetic protein activity.

INCORPORATION BY REFERENCE OF SEQUENCE LISTING

The official copy of the sequence listing is submitted electronically via EFS-Web as an ASCII formatted sequence listing with a file named 49955A_Seqlisting.txt, created on May 2, 2016, and having a size of 6,663 bytes and is filed concurrently with the specification. The sequence listing contained in this ASCII formatted document is part of the specification and is herein incorporated by reference in its entirety.

BACKGROUND OF THE INVENTION

The endocrine cells of the pancreas are organized in clusters termed islets of Langerhans, which are interspersed throughout the exocrine compartment. The main cellular component of the islet is the βcell (50-80%, depending on the species), which regulates blood glucose levels by secreting insulin. These cells are targeted by auto-reactive T cells in the autoimmune disorder known as type 1 diabetes. Chronic insulin administration is a life-saving intervention, but one that fails to prevent long-term complications that include blindness, vascular disease and kidney failure. Islet transplantation is a successful cell therapy for type 1 diabetes, especially since the development of steroid-free immunosuppression protocols (Shapiro et al. (2000) *N Engl J Med* 343, 230-8) and, more recently, T cell-depleting interventions that ensure long-term graft function (Bellin et al. (2008) *Am J Transplant* 8: 2463-70). However, its clinical application is limited by the shortage of donors (Ricordi et al. (2004) *Nat Rev Immunol* 4, 259-68). Thus, methods and compositions are needed to improve the state of the art as it relates to islet translation and for the treatment of type 1 diabetes.

SUMMARY OF THE INVENTION

Various compositions and methods are provided for generating islet-like cell clusters. The methods provided herein include culturing a whole non-islet pancreatic cell discard with an effective amount of a molecule having Bone Morphogenetic Polypeptide (BMP) activity or an active variant or fragment thereof. The effective amount of the molecule having BMP activity is sufficient to induce the formation of islet-like cell clusters. The methods further include treating or attenuating a variety of insulin-deficiency disorders, including type 1 diabetes and type 2 diabetes. In one non-limiting embodiment, an insulin-deficiency disorder in a subject is treated or attenuated by culturing a whole non-islet pancreatic cell discard with an effective amount of a molecule having BMP activity or an active variant or fragment thereof, such that the formation of islet-like cell clusters occurs. A therapeutically effective amount of the islet-like cell clusters are then transplanted into a subject in need thereof to thereby alleviate or treat the insulin-deficiency disorder. In another embodiment, an insulin-deficiency disorder in a subject is treated or attenuated by administering an effective amount of a molecule having BMP activity or an active variant or fragment thereof to the subject.

In some embodiments, the molecule having BMP activity comprises a Bone Morphogenetic Polypeptide (BMP) or an active variant or fragment thereof. Exemplary BMPs include, but are not limited to, BMP-1, BMP-2, BMP-3, BMP-4, BMP-5, BMP-6, BMP-7, BMP-8, BMP-9, BMP-10, BMP-11 and BMP-12. In some embodiments, the BMP is BMP-7. In some embodiments, the molecule having BMP activity activates a BMP receptor. In some embodiments, the molecule having BMP activity is THR-123.

DESCRIPTION OF THE FIGURES

The present invention will be better understood and features, aspects and advantages other than those set forth herein will become apparent when consideration is given to the following detailed description thereof. Such detailed description makes reference to the following drawings, wherein:

FIG. 4 provides functional in vivo characterization of BMP-7-treated hNEPT. (A) Human C-peptide determinations in nu/nu, stz-treated mice transplanted with BMP-7-treated, untreated hNEPT or saline (sham) following IPGTT. Left column: hNEPT/mouse recipient identifiers. 2nd/5th columns: post-operative day (POD) of serum human C-peptide determination. 3rd/4th columns: human C-peptide concentrations (pM) obtained prior to (0 min) and 60 minutes after glucose bolus injection (2.0 g/kg body weight) at POD 25-39. 6th/7th columns: human C-peptide values obtained at POD 108-122. (B, C) Average glucose-stimulated human C-peptide release (0 and 60 minutes, represented by light grey and black columns, respectively) at POD 25-39 (B) and POD 108-122 (C). X-axis: C (saline), sham controls; C (untreated), control mice transplanted with untreated hNEPT; BMP-7, mice transplanted with BMP-7-treated NEPT. Y-axis: C-peptide (pM). Data are presented as mean +/− standard deviation (n=12). *P<0.05.

FIG. 13 illustrates the antibodies used for the studies presented herein. Secondary antibodies: Alexa Fluor 488 (706-545-148), 594 (706-515-148) and 647 (706-605-148) Conjugate AffinityPure Donkey Anti-Guinea Pig and Flourescein (FITC)—conjugated Donkey anti-chicken (703-096-156), all from Jackson ImmunoResearch laboratories, Inc. Donkey anti-goat 568, donkey anti rabbit 488, donkey anti-mouse 594, donkey anti-mouse 647, goat anti-chicken 488, goat anti-rabbit 488, goat anti-mouse 488 and goat anti-rabbit 568, all from Life technologies: Nucleus was counter-stained with 4', 6-diamidino-2-phenylindole (DAPI, Life Technologies D1306).

DETAILED DESCRIPTION OF THE INVENTION

Figure 1:
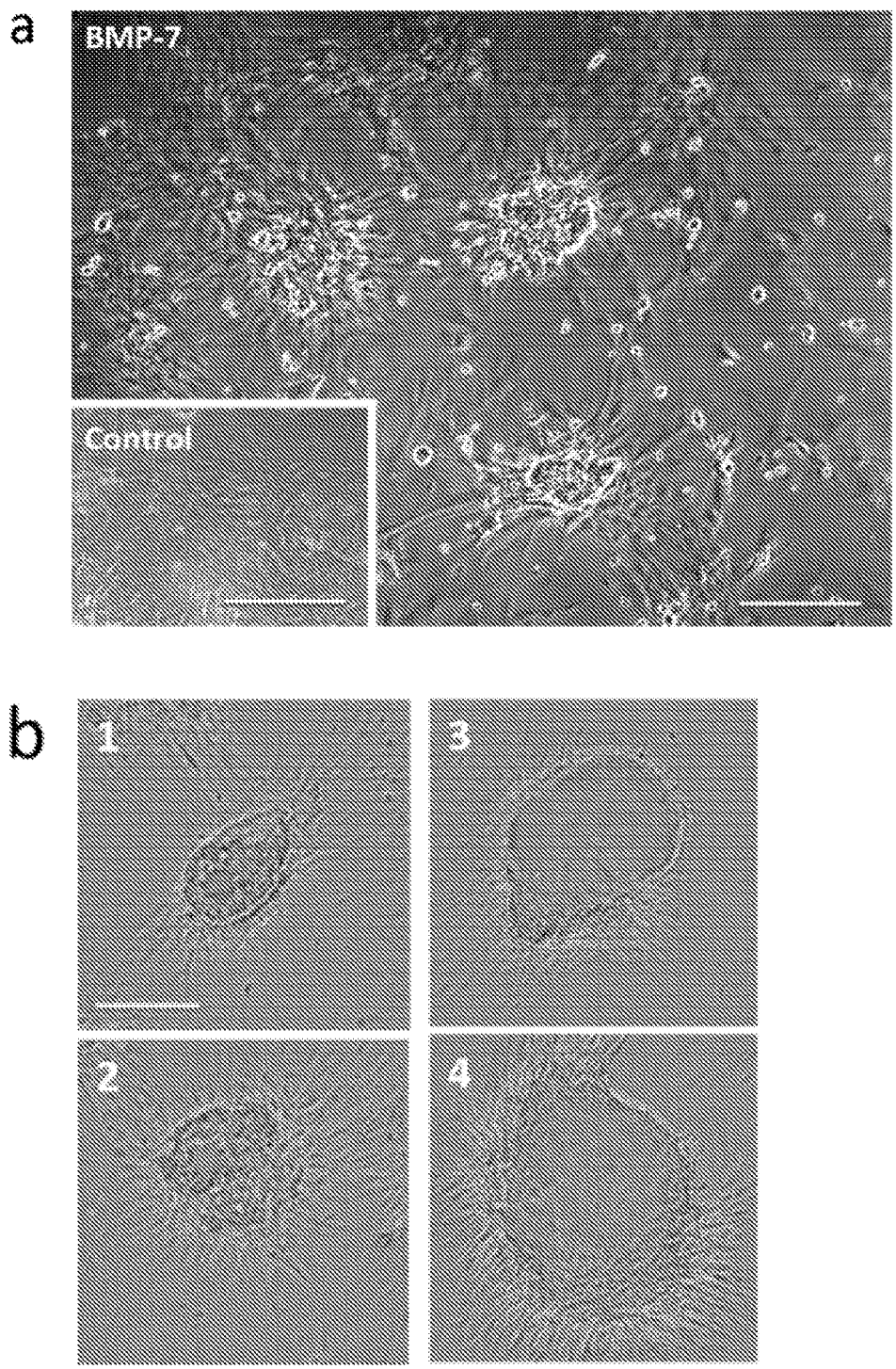
FIG. 1 demonstrates BMP-7 induces endocrine-like colonies in hNEPT cultures. (A) Administration of BMP-7 to hNEPT results in the formation of cellular clusters, in contrast to the monolayer pattern that is mainly observed in untreated controls (inset) at the same time point (10 days from the beginning of culture). Size bars: 100 µm. (B) An Incucyte Zoom® instrument was used to capture still images of the same colony at four time points throughout the 10 days after BMP-7 addition. Size bar: 50 µm. (C, D). Representative markers of adult pancreatic cells (C, top), pancreatic development (C, bottom) and EMT (D) were analyzed by TLDA qRT-PCR in BMP-7-treated and untreated hNEPT at the same time point after completion of the protocol. Values represent fold change (RQ ratios) vs. the untreated control. Following the Shapiro-Wilk normality test, statistical differences between RQs were calculated by two-tailed paired t test or Wilcoxon signed rank test. *P<0.005; P<0.01; *P<0.05; n.s., no significance (P>0.05).
Figure 1:
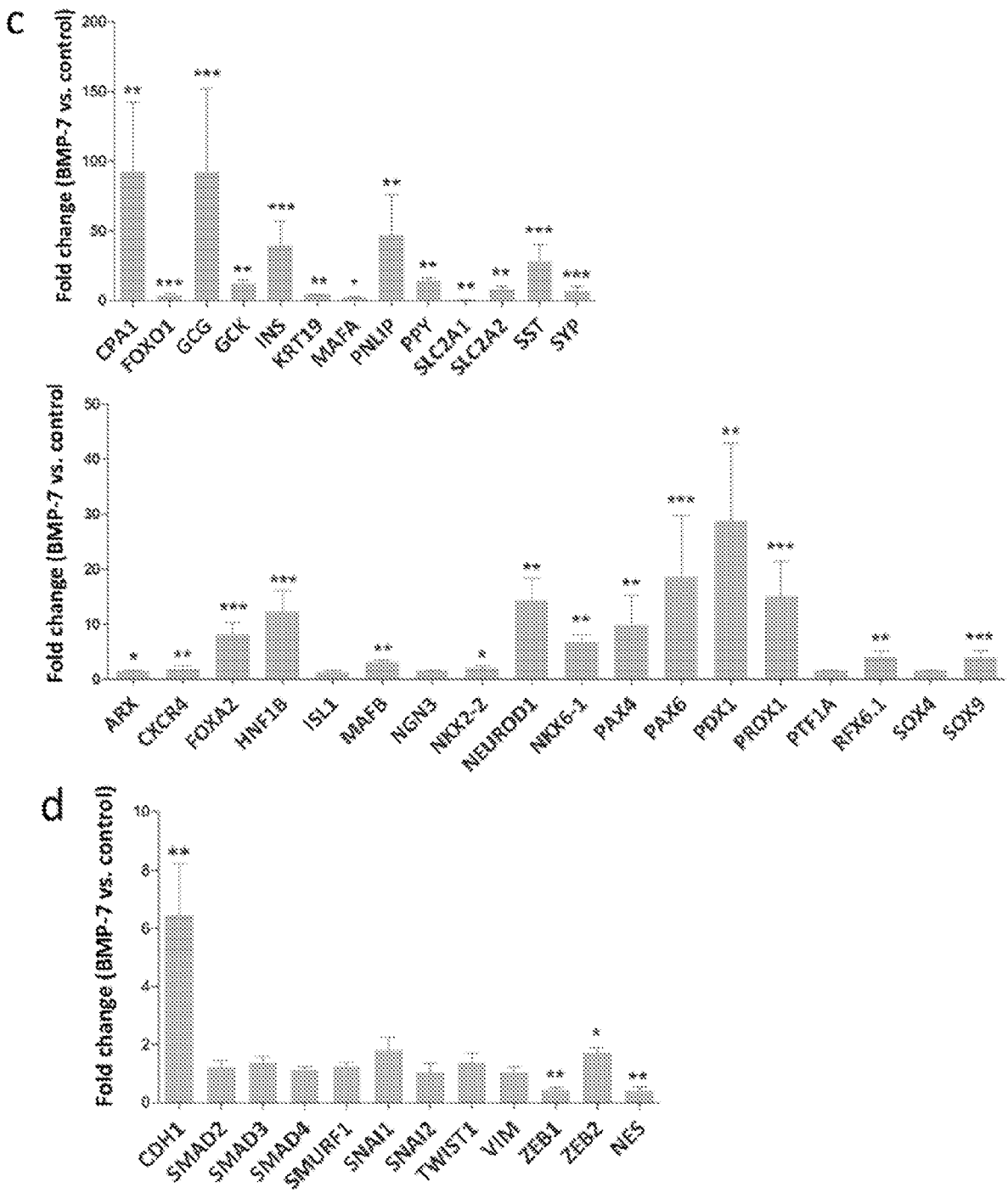

Unless defined otherwise, all technical and scientific terms used herein have the same meaning as commonly understood by one of ordinary skill in the art to which the invention pertains. Many modifications and other embodiments of the invention set forth herein will come to mind of one of ordinary skill in the art having the benefit of the teachings presented in the foregoing description and the associated drawings. Therefore, it is to be understood that the invention is not to be limited to the specific embodiments described herein and that other embodiments are intended to be included within the scope of the appended claims. Although specific terms are employed herein, they are used in a generic and descriptive sense only and not for purposes of limitation.

The exocrine pancreas can give rise to insulin-producing cells upon ectopic expression of specific transcription factors. However, the need for genetic manipulation remains a hurdle for diabetes therapy. Here we report the non-genetic conversion of adult human non-endocrine pancreatic tissue (hNEPT) into functional endocrine cells by bone morphogenetic protein 7 (BMP-7). The use of this FDA-approved agent results in the generation of cell clusters with high insulin content and glucose responsiveness in vitro and in vivo. These effects were partially inhibited by dorsomorphin, a canonical BMP signaling inhibitor that acts through the SMAD pathway. BMP-7 was hypothesized to stimulate heretofore-unreported cells within the exocrine compartment characterized by the co-expression of PDX1 and the BMP-7 receptor ALK3. Cells with these characteristics were absent from islets. In vitro lineage tracing confirmed that insulin-expressing cells arise mainly from extrainsular PDX1$^+$ sub-populations. Our findings point to a human β-cell regeneration mechanism with distinct translational potential.

Several approaches are presently under study to restore β-cell mass after the onset of type 1 diabetes (T1D). Islet transplantation has proven successful[1,2], but the scarcity of donor pancreata limits its clinical implementation. Converting the non-endocrine cells of the pancreas (which represent ~98% of the organ) into (β-cells is one of the proposed alternatives. Proof of concept has been generated using reprogramming approaches, which normally require the ectopic expression of (β-cell 'master' genes[3,4,5,6,7] and, in the case of human exocrine cells, also chromatin-modifying agents[7]. The clinical translation of these strategies is difficult owing to regulatory hurdles related to genetic manipulation, non-specific genome-wide chromatin rearrangements and the use of viral vehicles.

On the other hand, the exocrine (acinar, ductal) compartment of the pancreas has been hypothesized to harbor progenitor cells with the ability to give rise to new (β-cells through differentiation, rather than reprogramming. While their existence—let alone their phenotype—remains the subject of debate, the widespread consensus is that any such putative progenitors should express the pancreatic-duodenal homeobox protein 1 (PDX1)[8,9,10,11]. During the embryonic development of the pancreas, PDX1 is expressed in pancreatic progenitors at different stages[12], and it remains a major regulator of insulin transcription in adult β-cells[13]. While PDX1 has been reported to be mainly restricted to islet β-cells in the adult mouse[14], the human extrainsular tissue teems with PDX1+/insulin- cells. Adult PDX1-expressing progenitor-like cells mature into insulin-producing cells following in vitro induction with specific growth factors and extracellular matrix components [11].

Here we describe the BMP-7-induced conversion of adult human non-endocrine pancreatic tissue (hNEPT) into clusters that express high insulin levels and exhibit glucose responsiveness in vitro and in vivo. These effects were abrogated to a large extent by dorsomorphin, a SMAD/BMP signaling inhibitor. In vitro lineage-tracing experiments confirmed that newly formed β-like cells arise preferentially from PDX1+/insulin- cells rather than from acinar, pre-existing β-cells or cells expressing the pan-ductal marker carbonic anhydrase II (CAII). Taken together, the results are consistent with the BMP-7-mediated activation of a progenitor-like sub-population of cells within the human pancreatic exocrine compartment characterized by the co-expression of PDX1 and the BMP receptor ALK3. Cells with these characteristics are widely distributed throughout the ductal tree, but those with highest ALK3 expression reside in the major pancreatic duct epithelium and are also characterized by the lack of CAII expression—a result that is in line with lineage-tracing data. These findings thus suggest for the first time an exact anatomical location for putative progenitor-like cells within the pancreas. From a translational perspective, the demonstration that such cells can be activated through a non-genetic intervention with a single, FDA-approved compound may open the door to the design of potentially transformative therapies for diabetes.

Methods and compositions are provided for the reprogramming of human non-endocrine pancreatic tissue (NEPT) along the β cell lineage by exposure of primary exocrine tissue to a molecule having bone morphogenetic protein (BMP) activity. In some methods, the molecule having BMP activity is a bone morphogenetic protein (BMP). Such methods and compositions allow for the formation of islet-like cell clusters, which in some embodiments secrete total insulin levels in response to glucose comparable to those of native islets. The use of a molecule having BMP activity for pancreatic non-endocrine to endocrine conversion represents a safer, simpler and more effective alternative to transcription factor (TF)-mediated reprogramming. In fact, most attempts at reprogramming NEPT so far have been made using genetic approaches that entail the transfection of the recipient cells with 3-4 gene cassettes, upon whose expression some degree of reprograming is achieved. However, genetic manipulation approaches typically require the use of viruses and are generally deemed dangerous for clinical applications.

Thus, in one embodiment, a method for producing insulin-producing tissue is provided and comprises (a) providing a whole non-islet pancreatic cell discard or cells sorted therefrom; and (b) culturing the whole non-islet pancreatic cell discard or cells sorted therefrom with an effective amount of a molecule having BMP activity or an active variant or fragment thereof, wherein the effective amount of the molecule having BMP activity is sufficient to induce the formation of islet-like cell clusters. Further provided are compositions comprising an islet-like cell cluster produced by the various methods disclosed herein. In some embodiments, the molecule having BMP activity is a BMP.

Methods of treating or preventing an insulin-deficiency disorder in a mammal in need thereof are also provided. In one embodiment, the method comprises culturing a whole non-islet pancreatic cell discard or cells sorted therefrom with an effective amount of a molecule having BMP activity or an active variant or fragment thereof, wherein said effective amount of said molecule having BMP activity is sufficient to induce the formation of an islet-like cell clusters; and administering to the mammal a therapeutically effective amount of the islet-like cell clusters to allow for an increase in insulin production from said mammal. In another embodiment, the method comprises administering to a mammal an effective amount of a molecule having BMP activity, wherein the effective amount of the molecule having BMP activity is sufficient to induce the formation of an islet-like cell clusters to allow for an increase in insulin production from said mammal.

As used herein, the terms "non-islet pancreatic cell discard" or "non-islet pancreatic cells" or "pancreatic discard" are used interchangeably and refer to all cell populations derived from pancreatic tissue which remains after the isolation of pancreatic islets. The non-islet pancreatic cell discard comprises substantially insignificant amounts of islet cells, and thus represents a population of substantially exocrine cells. The non-islet pancreatic cell discard can be obtained from a variety of sources. In one embodiment, the pancreatic discard is from a human; however, it is recognized that the pancreatic discard can come from any mammal including, agricultural mammals or domesticated mammals. In one embodiment, the pancreatic discard is from pig. The discard can be from any developmental time period including, for example, from an adult or from a fetal tissue. The non-endocrine portion (NEPT) of the pancreas represents in excess of 95% the overall mass of the organ. This tissue is routinely discarded after the isolation of islets (1-2%) for clinical applications. The method and compositions disclosed herein provide a novel means to use this non-endocrine part of the pancreas to create new islets.

As used herein, a "whole" non-islet pancreatic cell discard comprising a non-islet pancreatic discard has not been further processed to remove any additional cell types. For example, a "whole non-islet pancreatic discard" has not been further processed to remove vascular endothelia cells (VECs) or pancreas-derived non-endocrinal epithelial cells (NEECs). Methods of obtaining a whole non-islet fraction of pancreata are known. See, for example, Noguchi and Matsumoto (2008) J. Hepatobiliary Pancreat Surg. 15(3):278-83; Ricordi et al. (1988) Diabetes 37(4): 413-20; Brandhorst et al (1998) Cell Transplantation 7(5):489-95 (1998).

Alternatively, the non-islet pancreatic cell discard can be further processed to separate or sort out cells from the tissue. For example, cells that are responsive to a molecule having BMP activity can be sorted as described in detail elsewhere herein. The cells sorted from the non-islet pancreatic cell discard may include, for example, progenitor cells that express the cell surface markers activin-like kinase receptor (ALK3) and Purinergic Receptor P2Y1 (P2RY1).

Culturing a whole non-islet pancreatic cell discard or cells sorted therefrom, as described herein, results in the formation of "islet-like cell clusters", which in some embodiments, comprise glucose-responsive cell clusters which secrete insulin. As used herein, an "islet-like cell cluster" comprises a cell cluster that resembles pancreatic islets both histologically and/or functionally. An islet-like cell cluster resembles pancreatic islets histologically if one or more of the molecular markers which characterize the pancreatic islet is present in the islet-like cell cluster. Various molecular markers that can be followed to monitor the histology of the islet-like cell clusters are known and include, but are not limited to, any one or more of the following: increased insulin expression and/or an increased expression of other islet hormones such as SST, PPY and Glucagon (GCG) and/or increased expression of key islet development markers such as PDX1, HNF1B and/or NeuroD1 and/or increased expression of one or more consensus markers of beta-cell maturity such as GLUT1, GLUT2, GCK and Nkx6.1. Various methods to assay for these markers are known. See, for example, the experimental section herein.

In specific embodiments, the islet-like cell clusters may further display other histological markers including the upregulation of the epithelial marker CDH1 and the down-regulation of mesenchymal genes such as VIM, NES, as well as the EMT core transcription factors ZEB1, SNAI2 and additionally SNAI1 TWIST1 and ZEB2. SMAD4 can also be down-regulated, which would be consistent with an attenuation of the TGF-β pathway. In addition, the islet-like cell cluster may further up-regulate pancreatic extra-insular genes such as KRT-19, CPA1 and PNLIP thereby impacting ductal and acinar growth. Various methods to assay for these markers are known. See, for example, the experimental section herein.

Moreover, in specific embodiments, the islet-like cell clusters may further have a minority number of polyhormonal cells within the cluster. In such instances, the majority of cells within the islet-like cell cluster stain independently for each of the endocrine hormones.

An islet-like cell cluster resembles pancreatic islets functionally if the cell cluster produces insulin in response to glucose. Any statistically significant amount of insulin produced by the islet-like cluster when compared to an appropriate control (e.g., whole non-islet pancreatic discard) is sufficient to qualify the cell cluster functionally as an islet-like cluster. In specific embodiments, the insulin produced can be at least 5%, 10%, 20%, 30%, 40%, 50%, 60%, 70%, 80%, 90%, 100%, 110%, 120%, 130%, 140% 105% or greater than the level of total insulin produced by native islets.

In specific embodiments, the islet-like cell cluster can have an insulin content range from about 500 to about 3000 ng of insulin/ug of DNA, from about 50 to about 1600 ng of insulin/ug of DNA, or from about 5 ng to about 50 ng/ug of insulin/ug of DNA. In further embodiments, the islet-like cell cluster can have an insulin content range from about 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 700, 800, 900, 1000, 1500, 2000, 2500, 3000, 3500 ng of insulin/ug of DNA or greater. Such insulin levels could occur in vitro (prior to transplantation) or such levels could be achieved following transplantation into a relevant host. In specific embodiments, islet-like cell clusters produce total insulin levels within one order of magnitude of those of native islets. Various methods can be used to determine if the islet-like cell cluster is producing insulin. For example, the cluster can be assayed for the ability to secrete in vitro insulin in response to glucose. Such methods, including for example, the glucose stimulated insulin secretion (GSIS) assays and the average stimulation index (SI) which are described in detail herein in the experimental section. In specific embodiments, an islet-like cell cluster produces a total insulin level "comparable" to that of a native islets. This occurs if the total insulin level of the islet-like cell cluster is within one order of magnitude as that of the native islets.

I. Molecules Having Bone Morphogenetic Protein (BMP) Activity

The various methods of producing an islet-like cell cluster employ the use of at least one molecule having Bone Morphogenetic Protein (BMP) activity. "Molecules having BMP activity" includes any molecule that can activate a BMP receptor. By "BMP activity" is meant the activation of a BMP receptor. Various methods to measure BMP receptor activation are known in the art and examples of such methods are provided elsewhere herein. Specifically, the whole non-islet pancreatic cell discard or cells sorted therefrom is cultured in vitro in an effective amount of at least one molecule having BMP activity. In one embodiment, the molecule having BMP activity is a BMP.

Bone morphogenetic proteins (BMPs) are multi-functional growth factors belonging to the transforming growth factor-β (TGF-β) superfamily. Family members are expressed during limb development, endochondral ossification, early fracture, and cartilage repair. More than 15 BMP family members have been identified and characterized. The signal triggered by BMPs is transduced through serine/threonine kinase receptors, type I and II subtypes. Three type I receptors have been shown to bind BMP ligands, namely: type IA and IB BMP receptors and type IA activin receptors, such as the activin-like kinase receptors ALK1, ALK2, ALK3, ALK4 and ALK5. BMPs seem to be involved in the regulation of cell proliferation, survival, differentiation and apoptosis, but their hallmark is their ability to induce bone, cartilage, ligament, and tendon formation at both heterotopic and orthotopic sites. See, for example, Granjeiro JM (2005) Braz J Med Biol Res. 2005 Oct; 38(10):1463-73; Elima K (1993) Osteoinductive proteins. Ann Med 25:395 402; Hoffmann et al. (2001) Appl Microbiol Biotechnol 57: 294 308; Vukicevic et al. (1995) Eur J Clin Chem Clin Biochem 33:661 671; Wozney J M (1992) Mol Reprod Dev 32:160 167; and, Wozney J M (1998) Eur J Oral Sci 106 (Suppl 1):160 166, each of which is herein incorporated by reference. Non-limiting examples of BMPs include BMP-2, BMP-3 (osteogenin), BMP-3B (GDF-10), BMP-4 (BMP-2B), BMP-5, BMP-6 (VGR-1), BMP-7 (OP-1), BMP-8 (OP-2), BMP-9, BMP-10, BMP-11)(GDF-8 or myostatin), BMP-12 (GDF-7), BMP-13 (GDF-6), BMP-14 (GDF-5) and BMP-15. The term BMP also encompasses naturally occurring variants (e.g., splice variants, allelic variants and other known isoforms), as well as fragments or variants of BMPs that are active. BMP polypeptides are known from a variety of different sources.

Any molecule having BMP activity (e.g., BMP-7 activity) can be used in the methods and compositions provided herein. In one embodiment, the molecules having BMP activity can be any of the various BMPs described herein. In another embodiment, the molecules having BMP activity can be any molecule that activates a BMP receptor, including, for example, a peptide agonist THR-123 and variants thereof, which has been shown to activate ALK3, which is disclosed in Sugimoto, H., et al., 2012, Nature Medicine 18(3):396-404 and U.S. Patent Publication NO. 2014/0057831, the disclosure of which are herein incorporated by reference in their entireties.

In one embodiment, the molecule having BMP activity comprises Bone Morphogenetic Protein-7 (BMP-7). As used herein, "Bone Morphogenetic Protein 7" or "BMP-7" is a 35 kDa homodimeric protein, involved in many biological functions in systems as diverse as the renal or skeletal. BMP-7 is a strong antagonist of TGF-β. It has been shown that BMP-7 and TGF-β have opposing actions, e.g., BMP-7 re-inducing the epithelial cell adhesion protein E-cadherin. See, for example, Zeisberg et al. (2003) Nat Med 9: 964-8 (2003). In one non-limiting embodiment, the BMP-7 polypeptide comprises human mature chain of BMP-7 (NCBI Reference Sequence: NM 001719.2) comprising peptide from 293-431. The sequence of which is herein incorporated by reference. The human mature chain of BMP-7 is set forth in SEQ ID NO:1, and the fragment comprising amino acids 293-431 is set forth in SEQ ID NO:2.

The term BMP-7 also encompasses naturally occurring variants (e.g., splice variants, allelic variants and other known isoforms), as well as fragments or variants of BMP-7 that are active. BMP-7 polypeptides are known from a variety of different sources including H.sapiens (Accession No. NP_001710.1), P.troglodytes (Acession No. XP_001170064.1), M.mulatta (Accession No. XP_001089245.1), C.lupus (accession No. NP_001183981.1), B.taurus (NP_001192944.1), M.musculus (accession No. NP_031583.2), R.norvegicu (Accession No. XP_342592.3), G.gallus (XP_417496.3), and D.rerio (NP_001070614.1), each of which is herein incorporated by reference. In addition, various BMP-7 sequences are further disclosed in U.S. Pat. No. 5,141,905, also incorporated by reference. Active variants and fragment of BMP-7 are also known. See for example, U.S. Pat. No. 7,459,527.

In other embodiments, BMP-4 (also known as ZYME; BMP2B; OFC11; BMP2B1; MCOPS6) is employed in the methods and compositions disclosed herein. A non-limiting example of BMP-4 is found as GenBank Accession No. NP_00193 (human BMP-4) or as GenBank Accession no NP_031580 (mouse BMP-4), both of which are herein incorporate by reference. A non-limiting example of a BMP-4 sequence is set forth in SEQ ID NO: 3.

Fragments and variants of the polynucleotides encoding the various molecules having BMP activity, for example, a BMP polypeptide (i.e, BMP-7 or BMP-4) can be employed in the various methods and compositions disclosed herein. By "fragment" is intended a portion of the polynucleotide and hence the protein encoded thereby or a portion of the polypeptide. Fragments of a polynucleotide may encode protein fragments that retain the biological activity of the native protein and hence have BMP activity. Thus, fragments of a polynucleotide may range from at least about 20 nucleotides, about 50 nucleotides, about 100 nucleotides, about 150, about 200, about 250, about 300, about 350, about 400, about 450, about 500, about 550, about 600 and up to the full-length polynucleotide encoding the molecule having BMP activity, for example, a BMP polypeptide (e.g., BMP-7, BMP-4, and/or SEQ ID NO: 1 or 2 or 3).

A fragment of a polynucleotide that encodes a biologically active portion of an molecule having BMP activity, for example, a BMP polypeptide will encode at least 15, 25, 30, 50, 100, 150, 200, 250, 300, 350, 400, 450 contiguous amino acids, or up to the total number of amino acids present in a full-length molecule having BMP activity, for example, a BMP polypeptide (e.g., BMP-7, BMP-4, and/or SEQ ID NO: 1 or 2 or 3).

A biologically active portion of a molecule having BMP activity, for example, a BMP polypeptide, can be prepared by isolating a portion of one of the polynucleotides encoding the portion of the molecule having BMP activity, for example, a BMP polypeptide, and expressing the encoded portion of the polypeptide (e.g., by recombinant expression in vitro), and assessing the activity of the portion of the molecule having BMP activity (e.g., BMP polypeptide). Polynucleotides that encode fragments of a molecule having BMP activity, for example, a BMP polypeptide, can comprise nucleotide sequence comprising at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length molecule having BMP activity(e.g., BMP) nucleotide sequence disclosed herein (e.g., BMP-7, BMP-4, and/or SEQ ID NO: 1 or 2 or 3).

"Variant" sequences have a high degree of sequence similarity. For polynucleotides, conservative variants include those sequences that, because of the degeneracy of the genetic code, encode the amino acid sequence of one of the molecule having BMP activity, for example, BMP polypeptides. Variants such as these can be identified with the use of well-known molecular biology techniques, as, for example, polymerase chain reaction (PCR) and hybridization techniques. Variant polynucleotides also include synthetically derived nucleotide sequences, such as those generated, for example, by using site-directed mutagenesis but which still encode molecule having BMP activity, for example, a BMP polypeptide. Generally, variants of a particular polynucleotide (such as a BMP-7 polypeptide, BMP-4 polypeptide, or the sequence set forth in SEQ ID NO: 1 or 2 or 3) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the molecule having BMP activity (e.g., BMP polypeptides) set forth herein (e.g., BMP-7, BMP-4, and/or SEQ ID NO: 1 or 2 or 3). Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins are biologically active, that is they continue to possess the desired biological activity of the native protein, that is, BMP activity. Such variants may result from, for example, genetic polymorphism or from human manipulation. Biologically active variants of a molecule having BMP activity, for example, a BMP polypeptide, will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein may differ from that protein by as few as 1-15 amino acid residues, as few as 1-10, such as 6-10, as few as 5, as few as 4, 3, 2, or even 1 amino acid residue.

Proteins may be altered in various ways including amino acid substitutions, deletions, truncations, and insertions. Methods for such manipulations are generally known in the art. For example, amino acid sequence variants of the molecules having BMP activity, for example, BMP proteins, can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferable.

Thus, the polynucleotides used in the invention can include the naturally occurring sequences, the "native" sequences, as well as mutant forms. Likewise, the proteins used in the methods of the invention encompass naturally occurring proteins as well as variations and modified forms thereof. Such variants will continue to possess the ability to implement a recombination event. Generally, the mutations made in the polynucleotide encoding the variant polypeptide should not place the sequence out of reading frame, and/or create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

II. Methods of Culturing a Whole Non-Islet Pancreatic Cell Discard

In the methods disclosed herein, the whole non-islet pancreatic cell discard or cells sorted therefrom is cultured with an effective amount of a molecule having BMP activity, for example, BMP (e.g., BMP-7, BMP-4, and/or SEQ ID NO: 1 or 2 or 3).

Various forms of molecules having BMP activity (e.g., BMP) can be used in the methods. In one embodiment, the molecule having BMP activity (e.g., BMP polypeptide) or active fragment or variant thereof comprises a purified molecule having BMP activity, for example, a BMP protein. Such a "purified" protein is substantially free of other cellular material or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein or culture medium, or non-protein-of-interest chemicals. The molecule having BMP activity (e.g., BMP polypeptide) or active fragment or variant thereof employed in the methods of the invention can be from any source. Alternatively, a molecule having BMP activity (e.g., BMP) can be made by recombinant methods well known in the art.

Other forms of molecules having BMP activity (e.g., BMPs) that can be used comprise that secreted by cells (other than the starting population of whole non-islet pancreatic cell discard) that produce molecules having BMP activity (e.g., BMPs) or active variants or fragments thereof. Such cells secreting molecules having BMP activity (e.g., BMP) could be either naturally occurring (such as kidney epithelium; see Wetzel et al. (2006) Kidney Int. Aug; 70(4): 717-23 for example) or generated by overexpression of a BMP-7 cassette (as, for example, in Odabas et al. (2012) J Tissue Eng Regen Med. Dec 26. doi: 10.1002/term.1634 or Yang et al. (2005) Cytotherapy 7(3):273-81)

As used herein, an "effective amount" of a molecule having BMP activity, for example, BMP (e.g., BMP-7, BMP-4, and/or SEQ ID NO: 1 or 2 or 3) or active variant or fragment thereof is the amount of a molecule having BMP activity (e.g., BMP) that is sufficient to induce the formation of islet-like cell clusters. Methods to assay for this production of these cells types are discussed elsewhere herein.

In specific embodiments, the effective amount of a molecule having BMP activity (e.g., BMP) comprises an amount of a molecule having BMP activity (e.g., BMP) that is sufficient to induce the formation of islet-like cell clusters in the absence of transcription factor (TF)-mediated reprogramming. As used herein, "transcription factor (TF)-mediated reprogramming" comprises the addition of exogenous transcription factors to the cells of the pancreatic discard culture to induce the reprograming of the cells. In one embodiment, an "exogenous" transcription factor comprises a transcription factor that is not expressed in cells (or a subpopulation of cells) of the whole non-islet pancreatic discard. In another embodiment, an "exogenous" transcription factor comprises a transcription factor that is expressed at a different level (e.g., an increased or a decreased level) than what is found in the cells (or a subpopulation of cells) of the whole non-islet pancreatic discard. Various methods are known for supplying cells with exogenous forms of transcription factors including genetic approaches that entail the transfection of the recipient cells with expression cassettes encoding the transcription factor, upon whose expression some degree of reprograming is achieved. Such genetic manipulation approaches typically require the use of viruses which are generally deemed dangerous for clinical applications.

An effective amount of a molecule having BMP activity (e.g., BMP) can comprise a final culture concentration of at least 75 ng/ml to at least 150 ng/ml, at least 50 ng/ml to at least 150 ng/ml, at least 50 ng/ml to at least 500 ng/ml, at least about 75 to about 400 ng/ml, at least about 75 ng/ml to about 300 ng/ml, at least about 75 ng/ml to at least about 200 ng/ml, at least about 75 ng/ml to about 250 ng/m. In other embodiments, the amount of a molecule having BMP activity (e.g., BMP) can comprise a final culture concentration of at least 10 ng/ml, 20 ng/ml, 30 ng/ml, 40 ng/ml, 50 ng/ml, 60 ng/ml, 70 ng/ml, 75 ng/ml, 80 ng/ml, 90 ng/ml, 100 ng/ml, 110 ng/ml, 120 ng/ml, 130 ng/ml, 140 ng/ml, 150 ng/ml, 160 ng/ml, 170 ng/ml, 180 ng/ml, or more. In specific embodiments, the amount of a molecule having BMP activity (e.g., BMP) comprises a final culture concentration of at least about 100 ng/ml.

An effective amount of BMP-7 can comprise a final culture concentration of at least 75 ng/ml to at least 150 ng/ml, at least 50 ng/ml to at least 150 ng/ml, at least 50 ng/ml to at least 500 ng/ml, at least about 75 ng/ml to about 400 ng/ml, at least about 75 ng/ml to about 300 ng/ml, at least about 75 ng/ml to at least about 200 ng/ml, at least about 75 ng/ml to about 250 ng/m. In other embodiments, the amount of BMP-7 can comprise a final culture concentration of at least 40 ng/ml, 50 ng/ml, 60 ng/ml, 70 ng/ml, 75 ng/ml, 80 ng/ml, 90 ng/ml, 100 ng/ml, 110 ng/ml, 120 ng/ml, 130 ng/ml, 140 ng/ml, 150 ng/ml, 160 ng/ml, 170 ng/ml, 180 ng/ml, or more. In specific embodiments, the amount of BMP-7 comprises a final culture concentration of at least about 100 ng/ml.

It is recognized that the parameters of the culture conditions can vary, so long as the islet-like cell cluster is formed.

The duration of the culturing of the whole non-islet pancreatic cell discard or the cells sorted therefrom will be the length of time required to form a sufficient number of islet-like cell clusters in the presence of an effective amount of a molecule having BMP activity (e.g., BMP) or an active variant or fragment thereof (e.g., BMP-7, BMP-4, and/or SEQ ID NO: 1 or 2 or 3). Methods to make such a determination are disclosed in further detail elsewhere herein. In specific embodiments, the duration of the culturing will be at least 1, 2, 3, 4, 5, 6, 7, 8, 9, 10, 11, 12, 13, 14, or 15 days or longer. In still further embodiments, the duration of culture will be from about 10 to about 11 days.

In one embodiment, the effective amount of a molecule having BMP activity (e.g., BMP) is cultured with the whole non-islet pancreatic cell discard or cells sorted therefrom in a serum-containing medium. In other embodiments, the effective amount of a molecule having BMP activity (e.g., BMP) is cultured with the whole non-islet pancreatic cell discard or cells sorted therefrom initially in a serum-containing medium, followed by a period of culture in a serum-free medium comprising an effective amount of a molecule having BMP activity (e.g., BMP). Such stages of culture can occur for a variety of different time periods, including, for example, 1, 2, 3, 4, 5, 6 or more days. In specific embodiments, the culturing in the serum-containing medium occurs for about 4 to about 5 days and the culturing in the non-serum containing medium occurs for about 4 to about 5 days.

In one non-limiting embodiment, culturing the whole non-islet pancreatic cell discard or cells sorted therefrom comprises a first culturing stage comprising culturing in the absence of a molecule having BMP activity (e.g., BMP) or a variant or fragment thereof (e.g., BMP-7, BMP-4, and/or SEQ ID NO: 1 or 2 or 3). Various forms of media can be employed in the first culturing stage including, but not limited to RPMI 1640 plus 10% serum. The first stage of culturing can occur for at least 1, 2, 3, 4, or more days and in specific embodiments, the first stage of culturing occurs for 2 days.

In further embodiments, culturing the whole non-islet pancreatic cell discard comprises a second culturing stage comprising culturing in the effective amount of a molecule having BMP activity (e.g., BMP) in a serum-containing medium. Various forms of media can be employed at this stage including, but not limited to Advanced RPMI 1640. The second stage of culturing can occur for at least 1, 2, 3, 4, 5, 6, 7 or more days, and in specific embodiments, the second stage of culturing occurs for 4 to 5 days.

In further embodiments, culturing the whole non-islet pancreatic cell discard or cells sorted therefrom comprises a third culturing stage comprising culturing in a non-serum containing media with or without the effective amount of a molecule having BMP activity (e.g., BMP). Various forms of non-serum containing media can be employed at this third culturing stage including, but not limited to Advanced RPMI 1640. The third stage of culturing can occur for at least 1, 2, 3, 4, 5, 6, 7 or more days and in specific embodiments, the third stage of culturing occurs for 4 days.

III. Methods of Isolating a Pancreatic Cell Population and Compositions Thereof

Provided herein are compositions comprising (β-cell progenitor cells and methods of isolating β-cell progenitor cells from whole non-islet pancreatic cell discard. Demonstrated herein in the Example section, is a population of (β-cell progenitor cells that comprise the markers Pancreatic-duodenal homeobox protein 1(PDX1) and activin-like kinase receptor 3 (ALK3). PDX1 is a marker located in the nucleus of the cell. The present invention demonstrates that the cell surface protein Purinergic Receptor P2Y1 (P2RY1) can serve as a surrogate marker for PDX1 expression. In some of the methods and compositions provided herein, the β-cell progenitor cells are positive for the cell surface markers ALK3 and P2RY1, but do not comprise carbonic anhydrase II (CAII).

In one embodiment, the non-islet pancreatic cell discard is exposed to a molecule having BMP activity prior to β-cell progenitor cell isolation. In another embodiment, the non-islet pancreatic cell discard is not exposed to a molecule having BMP activity prior to isolation of the β-cell progenitor cells.

In one embodiment, a method of isolating a β-cell progenitor cell is provided. Such a method comprises providing a single cell suspension of a whole non-islet pancreatic cell discard; sorting the cells using a combination of at least two cell surface markers, wherein the surface markers comprise surrogate surface markers for pancreatic-duodenal homeobox protein 1(PDX1) (e.g., Purinergic Receptor P2Y1 (P2RY1)), and activin-like kinase receptor 3 (ALK3); and (c) isolating the cells that are PDX1 (e.g., P2RY1$^+$) and ALK3 positive. In a specific embodiment, the surrogate surface marker for PDX1 is P2RY1.

In various embodiments, the sorting does not comprise assaying the cell suspension for ALK3-positive cells. In various embodiments, the sorting does not comprise assaying the cell suspension for cell surface markers other than P2RY1.

In another embodiment, additional sorting using surrogate surface markers for CAII would allow for selection of PDX1$^+$/ALK3$^+$/CAII$^-$ subpopulations (e.g., those responsive to a molecule having BMP activity).

Methods of isolating cells based on expression of cell surface markers are well known in the art and examples are described in the Example section provided herein. Non-limiting examples of methods for isolating cells include, fluorescence activated cell sorting and cell separation utilizing magnetic beads.

IV. Pharmaceutical Compositions

In some instances, islet-like cell clusters produced from the methods described above can be in a pharmaceutical composition having a therapeutically effective amount of the islet-like cell clusters in a pharmaceutically acceptable carrier. The pharmaceutical composition can be used to treat a subject having or susceptible to an insulin deficiency disorder, including for example, subjects having autoimmune type I diabetes. The compositions also find use in in vitro models for the study of beta cell physiology, or for preclinical transplantation models.

The molecules having BMP activity disclosed herein can also be incorporated into pharmaceutical compositions suitable for administration. Such compositions typically comprise one or more molecules having BMP activity and a pharmaceutically acceptable carrier. In specific embodiments, the pharmaceutical composition comprises a BMP or an active derivative thereof.

As used herein, a "pharmaceutically acceptable carrier" means a material that is not biologically, physiologically or otherwise undesirable, e.g., the material can be administered to a subject in a formulation or composition without causing any undesirable biological or physiological effects or interacting in a deleterious manner with any of the components of the composition in which it is contained.

A pharmaceutically acceptable carrier is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions may be conveniently presented in unit dosage form and prepared by any method well known in the art of pharmacy. Compositions of the present invention are preferably formulated for transplantation in the liver, pancreas, muscle, omentum, intraperitoneally, or subcutaneously. The islet-like cell clusters produced from the methods describe above may be carried, stored, or transported in any pharmaceutically or medically acceptable container, for example, an immunoisolation barrier (e.g., encapsulation) or device, a biocompatible scaffold, a blood bag, transfer bag, plastic tube or vial.

As used herein, a "therapeutically effective amount" (e.g., dosage) means an amount of islet-like cell clusters and/or an amount of a molecule having BMP activity (e.g. BMP) that are sufficient to treat or attenuate the disorder of interest (e.g., an insulin deficient disorder such as type 1 diabetes or type 2 diabetes). The therapeutically effective amount of islet-like cell clusters and/or of a molecule having BMP activity (e.g. BMP) to be administered will vary depending on the subject being treated, the severity of the disorder and the manner of administration.

The pharmaceutical compositions of the invention may contain, for example, more than one agent which may act independently of the other on a different target molecule. In some examples, a pharmaceutical composition of the invention, containing one or more compounds of the invention, is administered in combination with another useful composition such as an anti-inflammatory agent, an immunomodulator, a chemotherapeutic agent, an antibacterial agent, or the like. Furthermore, the compositions of the invention may be administered in combination with a cytotoxic, cytostatic, or chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Combination therapy (or "co-therapy") includes the administration of a therapeutic composition and at least a second agent as part of a specific treatment regimen intended to provide the beneficial effect from the co-action of these therapeutic agents. The beneficial effect of the combination includes, but is not limited to, pharmacokinetic or pharmacodynamic coactions resulting from the combination of therapeutic agents. Administration of these therapeutic agents in combination typically is carried out over a defined time period (usually minutes, hours, days or weeks depending upon the combination selected).

Combination therapy may, but generally is not, intended to encompass the administration of two or more of these therapeutic agents as part of separate monotherapy regimens that incidentally and arbitrarily result in the combinations of the present invention. Combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal. In addition, it may be desirable to administer a therapeutically effective amount of the pharmaceutical composition locally to an area in need of treatment. This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In one embodiment, administration can be by direct injection at the site that is to be treated. In another embodiment, the therapeutically effective amount of the pharmaceutical composition is delivered in a vesicle, such as liposomes (see, e.g., Langer, Science 249:1527-33, 1990 and Treat et al., in Liposomes in the Therapy of Infectious Disease and Cancer, Lopez Berestein and Fidler (eds.), Liss, N.Y., pp. 353-65, 1989).

A subject in whom administration of an active component as set forth above is an effective therapeutic regimen for an insulin deficiency disorder is preferably a human, but can be any animal. Thus, as can be readily appreciated by one of ordinary skill in the art, the methods and pharmaceutical compositions provided herein are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., e.g., for veterinary medical use.

In yet another embodiment, the therapeutically effective amount of the pharmaceutical composition can be delivered in a controlled release system. In one example, a pump can be used (see, e.g., Langer, Science 249:1527-33, 1990; Sefton, Crit. Rev. Biomed. Eng. 14:201-40, 1987; Buchwald et al., Surgery 88:507-16, 1980; Saudek et al., N. Engl. J. Med. 321:574-79, 1989). In another example, polymeric materials can be used (see, e.g., Levy et al., Science 228: 190-92, 1985; During et al., Ann. Neurol. 25:351-56, 1989;

Howard et al., J. Neurosurg. 71:105-12, 1989). Other controlled release systems, such as those discussed by Langer (Science 249:1527-33, 1990), can also be used.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL® (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In one embodiment, the method comprises the use of viruses for administering any of the various molecules having BMP activity provided herein to a subject. Administration can be by the use of viruses that express any of the molecules having BMP activity provided herein, such as recombinant retroviruses, recombinant adeno-associated viruses, recombinant adenoviruses, and recombinant Herpes simplex viruses (see, for example, Mulligan, Science 260: 926 (1993), Rosenberg et al., Science 242:1575 (1988), LaSalle et al., Science 259:988 (1993), Wolff et al., Science 247:1465 (1990), Breakfield and Deluca, The New Biologist 3:203 (1991)).

A gene encoding any of the various molecules having BMP activity provided herein can be delivered using recombinant viral vectors, including for example, adenoviral vectors (e.g., Kass-Eisler et al., Proc. Nat'l Acad. Sci. USA 90:11498 (1993), Kolls et al., Proc. Nat'l Acad. Sci. USA 91:215 (1994), Li et al., Hum. Gene Ther. 4:403 (1993), Vincent et al., Nat. Genet. 5:130 (1993), and Zabner et al., Cell 75:207 (1993)), adenovirus-associated viral vectors (Flotte et al., Proc. Nat'l Acad. Sci. USA 90:10613 (1993)), alphaviruses such as Semliki Forest Virus and Sindbis Virus (Hertz and Huang, J. Vir. 66:857 (1992), Raju and Huang, J. Vir. 65:2501 (1991), and Xiong et al., Science 243:1188 (1989)), herpes viral vectors (e.g., U.S. Pat. Nos. 4,769,331, 4,859,587, 5,288,641 and 5,328,688), parvovirus vectors (Koering et al., Hum. Gene Therap. 5:457 (1994)), pox virus vectors (Ozaki et al., Biochem. Biophys. Res. Comm. 193: 653 (1993), Panicali and Paoletti, Proc. Nat'l Acad. Sci. USA 79:4927 (1982)), pox viruses, such as canary pox virus or vaccinia virus (Fisher-Hoch et al., Proc. Nat'l Acad. Sci. USA 86:317 (1989), and Flexner et al., Ann. N.Y. Acad. Sci. 569:86 (1989)), and retroviruses (e.g., Baba et al., J. Neurosurg 79:729 (1993), Ram et al., Cancer Res. 53:83 (1993), Takamiya et al., J. Neurosci. Res 33:493 (1992), Vile and Hart, Cancer Res. 53:962 (1993), Vile and Hart, Cancer Res. 53:3860 (1993), and Anderson et al., U.S. Pat. No. 5,399,346). Within various embodiments, either the viral vector itself, or a viral particle, which contains the viral vector may be utilized in the methods provided herein.

When the subject treated with a recombinant virus is a human, then the therapy is preferably somatic cell gene therapy. That is, the preferred treatment of a human with a recombinant virus does not entail introducing into cells a nucleic acid molecule that can form part of a human germ line and be passed onto successive generations (e.g., human germ line gene therapy).

The pharmaceutical compositions can be included in a container, pack, or dispenser together with instructions for administration.

V. Methods of Use

The islet-like cell clusters and/or molecules having BMP activity (e.g., BMP) disclosed herein find particular use in treating or attenuating a variety of disorders which arise from a decreased level of insulin, including, for example, insulin-deficiency disorders such as type 2 diabetes, or autoimmune insulin-dependent diabetes, also known as type 1 diabetes. As used herein, "treatment" is an approach for obtaining beneficial or desired clinical results (e.g., "therapeutic response"). For purposes of this invention, beneficial or desired clinical results include, but are not limited to, alleviation or reduction of symptoms, diminishment of extent of disease, stabilization (e.g., not worsening) of disease, delay or slowing of disease progression, amelioration or palliation of the disease state, and remission (whether partial or total), whether detectable or undetectable. "Treatment" can also mean prolonging survival as compared to expected survival if not receiving treatment or receiving different treatment. "Treatment" refers to both therapeutic treatment and prophylactic or preventative measures. Those in need of treatment include those already with the disorder as well as those in which the disorder is to be prevented. "Alleviating" a disease means that the extent and/or undesirable clinical manifestations of a disease state are lessened and/or the time course of the progression is slowed or shortened, as compared to a situation without treatment or a different treatment Such improvement may be shown by a number of indicators. Measurable indicators include, for example, detectable changes in a physiological condition or set of physiological conditions associated with a particular disease, disorder or condition. Treatment of an individual with the islet-like cell clusters disclosed herein would be considered effective if any one of such indicators responds to such treatment by changing to a value that is within, or closer to, the normal value. The normal value may be established by normal ranges that are known in the art for various indicators, or by comparison to such values in a control. In medical science, the efficacy of a treatment is also often characterized in terms of an individual's impressions and subjective feeling of the individual's state of health. Improvement therefore may also be characterized by subjective indicators, such as the individual's subjective feeling of improvement, increased well-being, increased state of health, improved level of energy, or the like, after administration of the cell populations of the invention.

In one embodiment, the method of treatment comprises allogeneic transplantation of host (or "subject") cells. Allogeneic cell therapy involves the transplantation of cells to a subject, whereby the transplanted cells are derived from a donor other than the subject. Thus, methods of treating individuals having or suspected of having an insulin-deficiency disorder, such as type I diabetes, are provided which comprise administering to the subject allogeneic islet-like cell clusters. In such methods, the whole non-islet pancreatic cell discard (or cells sorted therefrom) is derived from a donor subject and culturing the cell population in the presence of an effective concentration of exogenous a molecule having BMP activity, for example, BMP (e.g., BMP-7, BMP-4, and/or SEQ ID NO: 1 or 2 or 3), as described herein, to produce islet-like cell clusters. The islet-like cell clusters can then be administered to the subject to treat the disorder.

It is recognized that the islet-like cell clusters being transplanted into the subject can be from the same species (e.g., human to human) or the islet-like cell clusters being transplanted into the subject can be from a species different than that of the subject (e.g., a xenotransplantation). For example, islet-like cell clusters from pigs could be transplanted into a human.

In still other embodiments, the method of treatment comprises autologous transplantation of host (or "subject") cells. Thus, methods of treating individuals having or suspected of having an insulin-deficiency disorder are provided which comprise administering to the subject autologous islet-like cell clusters. In such methods, the whole non-islet pancreatic cell discard (or cells sorted therefrom) is derived from a subject and the cell population is cultured in the presence of an effective concentration of exogenous molecules having BMP activity, for example, BMP (e.g., BMP-7, BMP-4, and/or SEQ ID NO: 1 or 2 or 3), as described herein, to produce islet-like cell clusters. The islet-like cell clusters can then be transplanted back into the subject to treat the disorder.

By "subject" is intended mammals, e.g., primates, humans, agricultural and domesticated animals such as, but not limited to, dogs, cats, cattle, horses, pigs, sheep, and the like. Preferably, the subject undergoing treatment is a human.

Transplantation of the islet-like cell clusters to a subject can be carried out using any method that allows for the successful transplantation of the islet-like cell clusters, including, for example, through the portal vein. See, for example, Shapiro et al. (2000) N Engl J Med 343(4):230-8; Ricordi (2003) Diabetes 52(7):1595-603; Ricordi and Strom (2004) Nat. Rev. Immunol 4(4):259-68; Pileggi et al. (2006), Minerva endocrinol 31(3):219-32. Alternatively, the islet-like cell clusters can be transplanted through the use of the omental pouch, the muscle, the venous sac, bioimplantable devices, etc., with or without the concomitant use of scaffolds, encapsulation, immunomodulatory cells, etc.

The islet-like cell cluster composition of the present invention should be introduced into a subject, preferably a human, in an amount sufficient to treat a desired disease or condition (e.g., an insulin deficiency disorder such as type I diabetes). For example, a therapeutically effective amount of islet-like cells can comprise an amount such that at least 5,000, 5,500, 6,000, 6,500, 7,000, 7,500, 8,000, 8,5000, 9,000, 9,500, 10,000, 10,500, 11,000, 11,500 or greater of islet equivalents (IEQ)/kg of body weight of the recipient is reached. In one embodiment, at least 10,000 islet equivalents (IEQ)/kg of body weight of the recipient is employed In this example, for a 50 kg patient, this would be half a million islets, at ~2,000 cells/islets=$1 \times 10^9$ cells.

In one embodiment, the method of treatment comprises administration of at least one molecule having BMP activity (e.g., BMP) or active variant or fragment thereof. When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a molecule having BMP activity (e.g., BMP) can include a single treatment or, preferably, can include a series of treatments. It will also be appreciated that the effective dosage of a molecule having BMP activity used for treatment may increase or decrease over the course of a particular treatment.

It is understood that appropriate doses of such active compounds depends upon a number of factors within the knowledge of the ordinarily skilled physician, veterinarian, or researcher. The dose(s) of the active compounds will vary, for example, depending upon the identity, size, and condition of the subject or sample being treated, further depending upon the route by which the composition is to be administered, if applicable, and the effect which the practitioner desires the active compound to have. Exemplary doses include milligram or microgram amounts of the a molecule having BMP activity per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of an active agent depend upon the potency of the active agent with respect to the expression or activity to be modulated. Such appropriate doses may be determined using the assays described herein. When one or more of these molecules having BMP activity is to be administered to an animal (e.g., a human) in order to treat or prevent insulin-deficiency disorders, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Therapeutically effective amounts of a molecules having BMP activity (e.g., BMP) can be determined by animal studies. When animal assays are used, a dosage is administered to provide a target tissue concentration similar to that which has been shown to be effective in the animal assays. It is recognized that the method of treatment may comprise a single administration of a therapeutically effective amount or multiple administrations of a therapeutically effective amount of the molecule having BMP activity.

In specific embodiments, the therapeutically effective amount of the molecule having BMP activity is between 50 μg/kg and 100 mg/kg. For example, the daily dosage amount can be for example about 50, about 100, about 150, about 200, about 250, about 300, about 350, about 400, about 450, about 500, about 600, about 700, about 800, or about 900 μg/kg. Additionally, the daily dosage amount can be for example about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, or about 100 mg/kg.

As used herein, "about" means within a statistically meaningful range of a value such as a stated concentration range, time frame, molecular weight, temperature or pH. Such a range can be within an order of magnitude, typically within 20%, more typically still within 10%, and even more typically within 5% of a given value or range. The allowable variation encompassed by the term "about" will depend upon the particular system under study, and can be readily appreciated by one of ordinary skill in the art.

V. Sequence Identity

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (e.g., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

As used herein, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

Non-limiting examples of the methods and compositions provided herein are as follows:

1. A method for producing insulin-producing tissue comprising: (a) providing a whole non-islet pancreatic cell discard or cells sorted therefrom; and, (b) culturing said whole non-islet pancreatic cell discard or cells sorted therefrom with an effective amount of a molecule having BMP activity or an active variant or fragment thereof, wherein said effective amount of said molecule having BMP activity is sufficient to induce the formation of an islet-like cell cluster.

2. The method of embodiment 1, wherein the molecule having BMP activity comprises a Bone Morphogenetic Polypeptide (BMP) or an active variant or fragment thereof.

3. The method of embodiment 2, wherein said BMP comprises a Bone Morphogenetic Polypeptide-7 (BMP-7), an active variant or fragment thereof.

4. The method of embodiment 1, 2, or 3, wherein said islet-like cell cluster comprises a glucose-responsive cell cluster that secretes insulin.

5. The method of embodiment 1, 2, 3 or 4, wherein the effective amount of the molecule having BMP activity or active variant or fragment thereof comprises at least about 75 ng/ml.

6. The method of any one embodiments 1-5, wherein culturing said whole non-islet pancreatic cell discard or cells sorted therefrom comprises a first culturing stag comprising culturing in the absence of the molecule having BMP activity or a variant or fragment thereof.

7. The method of embodiment 6, wherein said first culturing stage lasts at least 2 days.

8. The method of any one of embodiments 6 or 7, wherein culturing said whole non-islet pancreatic cell discard or cells sorted therefrom comprises a second culturing stage comprising culturing in the effective amount of a molecule having BMP activity in a serum containing medium.

9. The method of embodiment 8, wherein said second culturing stage lasts at least 4 days.

10. The method of any one of embodiments 8 or 9, wherein culturing said whole non-islet pancreatic cell discard or cells sorted therefrom comprises a third culturing stage comprising culturing in a non-serum containing medium with or without an effective amount of a molecule having BMP activity.

11. The method of embodiment 10, wherein said third culturing stage lasts at least 4 days.

12. The method of any one of embodiments 1-11, wherein said culturing occurs in the absence of transcription factor (TF)-mediated reprogramming.

13. An islet-like cell cluster produced by the method of any one of embodiments 1-12.

14. A method to increase insulin production in a mammal in need thereof comprising: (a) culturing a whole non-islet pancreatic cell discard or cells sorted therefrom with an effective amount of a molecule having BMP activity or an active variant or fragment thereof, wherein said effective amount of said molecule having BMP activity is sufficient to induce the formation of an islet-like cell cluster; and, (b) administering to the mammal a therapeutically effective amount of the islet-like cell clusters to allow for an increase in insulin production from said mammal.

15. A method to treat or prevent an insulin-deficiency disorder in a mammal in need thereof comprising: (a) culturing a whole non-islet pancreatic cell discard or cells sorted therefrom with an effective amount of a molecule having BMP activity or an active variant or fragment thereof, wherein said effective amount of said a molecule having BMP activity is sufficient to induce the formation of an islet-like cell clusters; and, (b) administering to the mammal a therapeutically effective amount of the islet-like cell clusters to allow for an increase in insulin production from said mammal.

16. The method of embodiment 14 or 15, wherein said molecule having BMP activity comprises a Bone Morphogenetic Polypeptide (BMP) or an active variant or fragment thereof.

17. The method of embodiment 16, wherein said BMP comprises a Bone Morphogenetic Polypeptide-7 (BMP-7), or an active variant or fragment thereof.

18. The method of embodiment 15, 16 or 17, wherein said insulin-deficiency disorder comprises type 1 diabetes.

19. The method of any one of embodiments 14-18, wherein said islet-like cell clusters comprise a glucose-responsive cell cluster that secrete insulin.

20. The method of any one of embodiments 14-19, wherein the effective amount of the molecule having BMP activity or active variant or fragment thereof comprises at least about 75 ng/ml.

21. The method of any one embodiments 14-20, wherein culturing said whole non-islet pancreatic cell discard or cells sorted therefrom comprises a first culturing stage comprising culturing in the absence of a molecule having BMP activity or a variant or fragment thereof.

22. The method of embodiment 21, wherein said first culturing stage lasts at least 2 days.

23. The method of any one of embodiments 21 or 22, wherein culturing said whole non-islet pancreatic cell discard or cells sorted therefrom comprises a second culturing stage comprising culturing in the effective amount of a molecule having BMP activity in a serum containing medium.

24. The method of embodiment 23, wherein said second culturing stage lasts at least 4 days.

25. The method of any one of embodiments 23 or 24, wherein culturing said whole non-islet pancreatic cell discard or cells sorted therefrom comprises a third culturing stage comprising culturing in a non-serum containing medium with or without the effective amount of a molecule having BMP activity.

26. The method of embodiment 25, wherein said third culturing stage lasts at least 4 days.

27. The method of any one of embodiments 14-26, wherein said culturing occurs in the absence of transcription factor (TF)-mediated reprogramming.

28. A method of isolating a (β-cell progenitor cell, said method comprising (a) providing a single cell suspension of a whole non-islet pancreatic cell discard; (b) sorting the cells using a combination of at least two cell surface markers, wherein the surface markers comprise Purinergic Receptor P2Y1 (P2RY1), and activin-like kinase receptor 3 (ALK3); and (c) isolating the cells that are P2RY1 positive and ALK3 positive.

29. A method to treat or prevent an insulin-deficiency disorder in a mammal in need thereof comprising: administering to said mammal an effective amount of a molecule having BMP activity or an active variant or fragment thereof, wherein said effective amount of said molecule having BMP activity is sufficient to allow for an increase in insulin production from said mammal.

30. The method of embodiment 29, wherein said molecule having BMP activity comprises a Bone Morphogenetic Polypeptide (BMP) or an active variant or fragment thereof.

31. The method of embodiment 30, wherein said BMP comprises a Bone Morphogenetic Polypeptide-7 (BMP-7), or an active variant or fragment thereof.

32. The method of embodiment 29-31, wherein said insulin-deficiency disorder comprises type 1 diabetes.

The subject matter of the present disclosure is further illustrated by the following non-limiting examples.

EXAMPLES

Example 1

BMP-7 Induces Phenotypic Changes Consistent With The Formation of New Endocrine Cells hNEPT preparations were obtained from as a byproduct of human pancreatic islet isolation. While there is substantial variation based on donor variables, the analysis of 5 independent fresh hNEPT preparations yielded an average of 68.96±25.8% PDX1+ cells, 50.82 ±24.6% CA19.9+ (ductal) cells, 35.88±28.9% amylase+ (acinar) cells, 6.32±2.9% CD105+ (mesenchymal) cells and 1.72±1.32% insulin+ cells, as determined by flow cytometry. The percentage of cells expressing ALK3 was prospectively analyzed, as this is one of the main receptors through which BMP-7 exerts its biological action in several models of regeneration[22-24]. 9.18±4.4% of the cells were ALK3+, and 8.2±5.1% were PDX1+/ALK3+ double positive. Of note, due to the rigors of isolation, the cell composition of the fresh hNEPT as determined by FACS does not fully correlate with that observed by immunofluorescence analysis of pancreatic sections.

Figure 8:
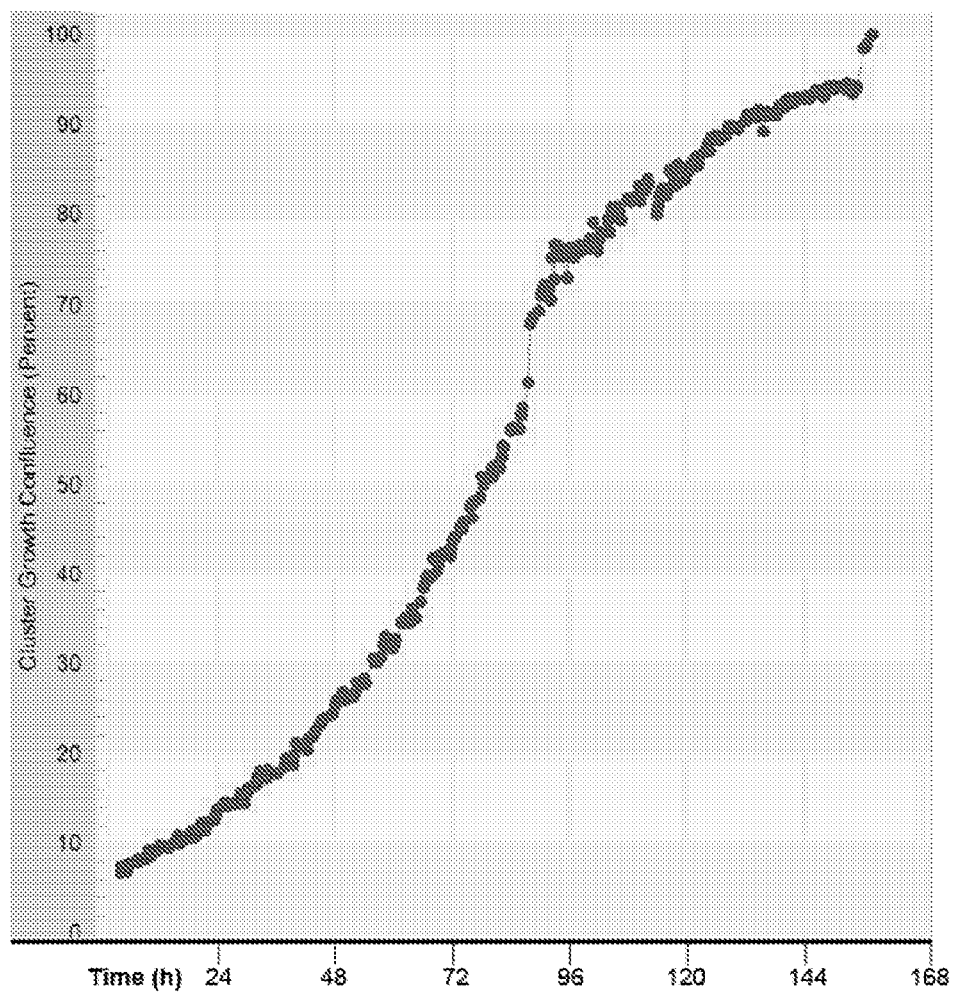
FIG. 8 provides Incucyte-assisted analysis of hNEPT colony growth upon BMP-7 exposure. X-axis: Time (hours). Y axis: Confluence percentage of a selected field.

Fresh hNEPT preparations were allowed to attach to tissue culture-treated plates for 48 h and subsequently exposed to BMP-7. The rationale behind the use of BMP-7 was that it may help reduce the incidence of EMT in cultured pancreatic exocrine tissue, as EMT has proven an obstacle for the formation of endocrine cells from exocrine cells in a similar setting[7]. Control aliquots were cultured in the same conditions but without BMP-7. Throughout the course of 12 days, BMP-7 induced the formation of abundant cellular clusters, whereas controls became mainly mesenchymal-like monolayers (FIG. 1a). The growth of the colonies in the BMP-7 group was followed by in situ live cell imaging (Incucyte Zoom) (FIG. 1b and FIG. 8). This increase in size was paralleled by an average increase of 4.8-fold in DNA content from the time of attachment to day 12 (n=2), which further evidenced active cell proliferation. In contrast, pure islet preparations (n=3) treated with BMP-7 failed to give rise to colonies.

The expression of 43 genes (including epithelial, acinar, islet and mesenchymal cell markers) was studied in hNEPT preparations (n=8) treated with BMP-7 and untreated controls at the same time point. As shown in FIG. 1c, BMP-7 induced gene expression changes consistent with robust endocrine cell conversion, evidenced by average increases of 40-fold in insulin, 92-fold in glucagon, 14-fold in pancreatic polypeptide (PPY), 28-fold in somatostatin (SST) and 29-fold in PDX1. GCK, MAFA and NKX6.1, as well as islet development markers HNF1B and NEUROD1 were also elevated. The up-regulation of extra-insular genes such as cytokeratin-19 (KRT-19), carboxypeptidase A (CPA1) and pancreatic lipase (PNLIP) suggests that BMP-7 impacts also ductal and acinar growth.

Such a result was unexpected. That BMP-7 by itself would induce reprogramming towards endocrine cell types was unexpected. Based on these unexpected results, we subsequently hypothesized that BMP-7 may activate progenitor cells that reside within the exocrine compartment of the pancreas. Activation of progenitor pools has been shown to be dependent on the simultaneous inhibition of TGF-β signaling (which generally acts as a brake upon progenitor cell stimulation[15, 16, 17]) and the activation of the BMP pathway[7, 18, 19, 20]. Bone morphogenetic protein 7 (BMP-7) is a homodimeric protein from the TGF-β superfamily with dual TGF-β inhibition/BMP activation abilities[15,20]. This led us to further hypothesize that PDX1-expressing putative β-cell progenitors may respond to BMP-7 stimulation.

Figure 9:
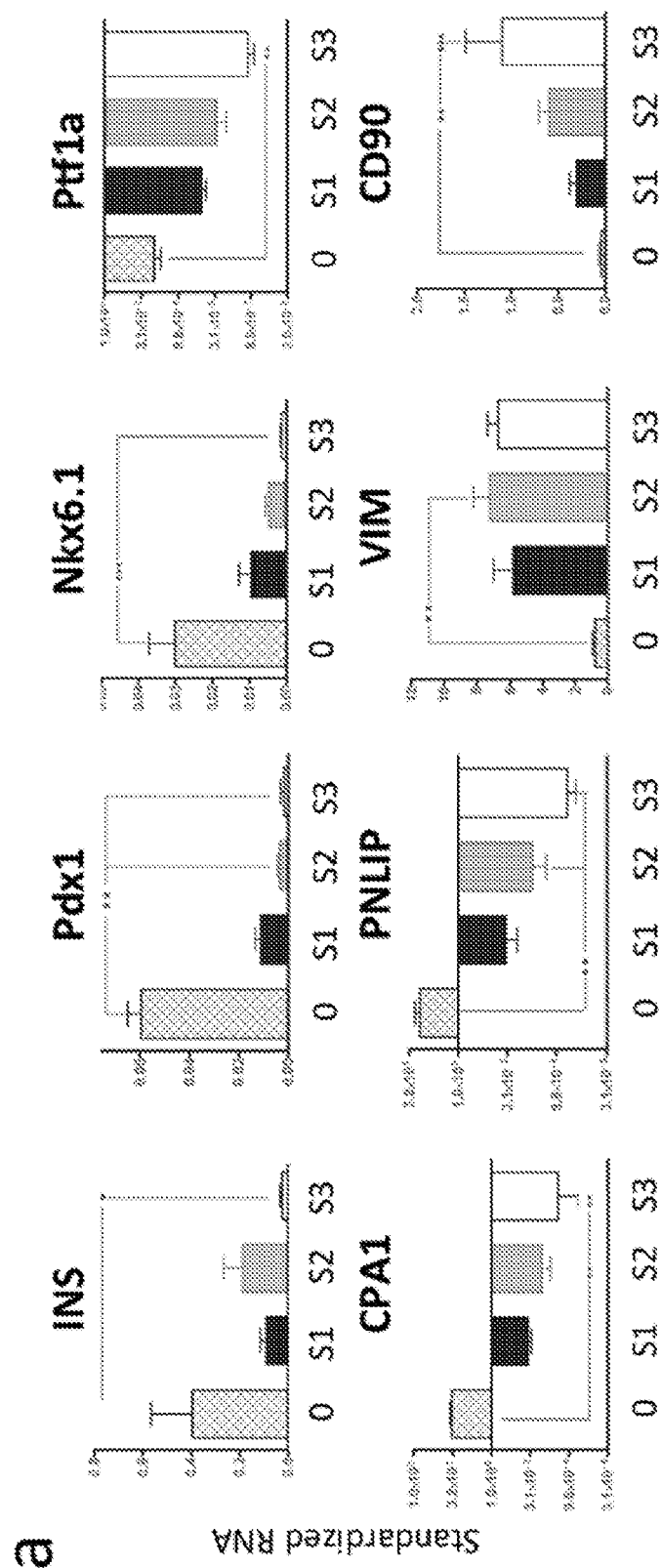
FIG. 9 demonstrates hNEPT cultures undergo phenotypic changes consistent with EMT. (A) TLDA qRT-PCR stage-wise analysis of gene expression of hNEPT as a function of time. Markers: INS (insulin), PDX1, Nkx6.1, Ptfl a, CPA1 (carboxypeptidase A), PNLIP (pancreatic lipase), VIM (vimentin) and CD90. X-axis, stages of culture: 0, after isolation; S1, stage 1 (days 6-8); S2, stage 2 (days 10-12); S3, stage 3 (days 15-17). Y axis: relative quantification. Data are presented as mean +/− standard deviation (n=8). Following the Shapiro-Wilk normality test, the statistical differences were calculated by two-tailed paired t test or Wilcoxon signed rank test (*). P<0.05; () P<0.01; (*) P<0.005. (B) Sequential immunofluorescence analysis of hNEPT cultures as a function of time. Stages 0, 1, 2 and 3 are as above. Top row: CA19.9 (ductal, green), amylase (acinar, red) and DAPI (nuclear, blue). Middle row: PDX1 (13 cells and ductal/putative 13 cell progenitors, green; in panel 2, arrows indicate regions rich in these cells), vimentin (mesenchymal, red) and DAPI (nuclear, blue). Bottom row: PDX1 (green), insulin (red) and DAPI (blue). Size bar: 50 µm.

Interestingly, despite its well-documented role at preventing epithelial-to-mesenchymal transition (EMT)[16], BMP-7 seemed to have only a marginal effect at reducing the mesenchymalization of hNEPT cultures, as only the EMT marker ZEB1 was significantly down-regulated (0.4-fold, p<0.01) and ZEB2 was even slightly up-regulated (1.6-fold, P<0.05). The epithelial marker E-cadherin (CDH1) was up-regulated (6-fold, p<0.01), but there were no significant changes in other EMT genes (FIG. 1d). This is significant because EMT has been reported to occur in human pancreatic exocrine cultures (and confirmed by our team; see FIG. 9), and its prevention has been posited to be critical for their reprogramming towards β-cells upon viral transfection with PDX1, MAFA, NGN3 and PAX47.

Figure 2:
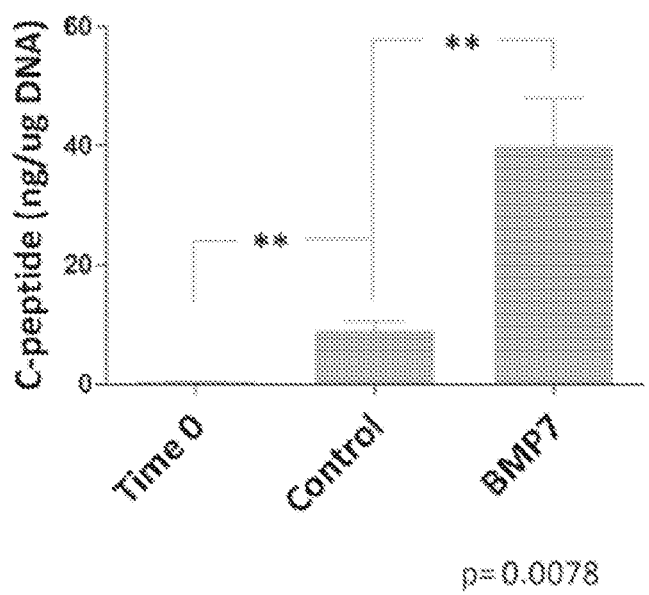
FIG. 2 provides C-peptide production upon BMP-7 treatment. (A, B) C-peptide content (ng/µg of DNA) of 8 independent hNEPT preps at day 0 and after 12 days (untreated and with BMP-7). Preparations 7 and 8 received BMP-7+5 µM dorsomorphin (a BMP signaling inhibitor). n.d., not determined. **P=0.0078. (C) C-peptide production (ng/µg DNA) following hNEPT treatment with BMP-4. P<0.05. (D) C-peptide production (ng/µg DNA) following hNEPT treatment with 100 ng/mL THR-12, an ALK3 agonist. (E) C-peptide production (mg/µg DNA) following hNEPT treatment with BMP-7 and BMP-7 plus dorsmorphin, a BMP-SMAD phosphorylation inhibitor. P=0.13. Ctrl=control.
Figure 2:
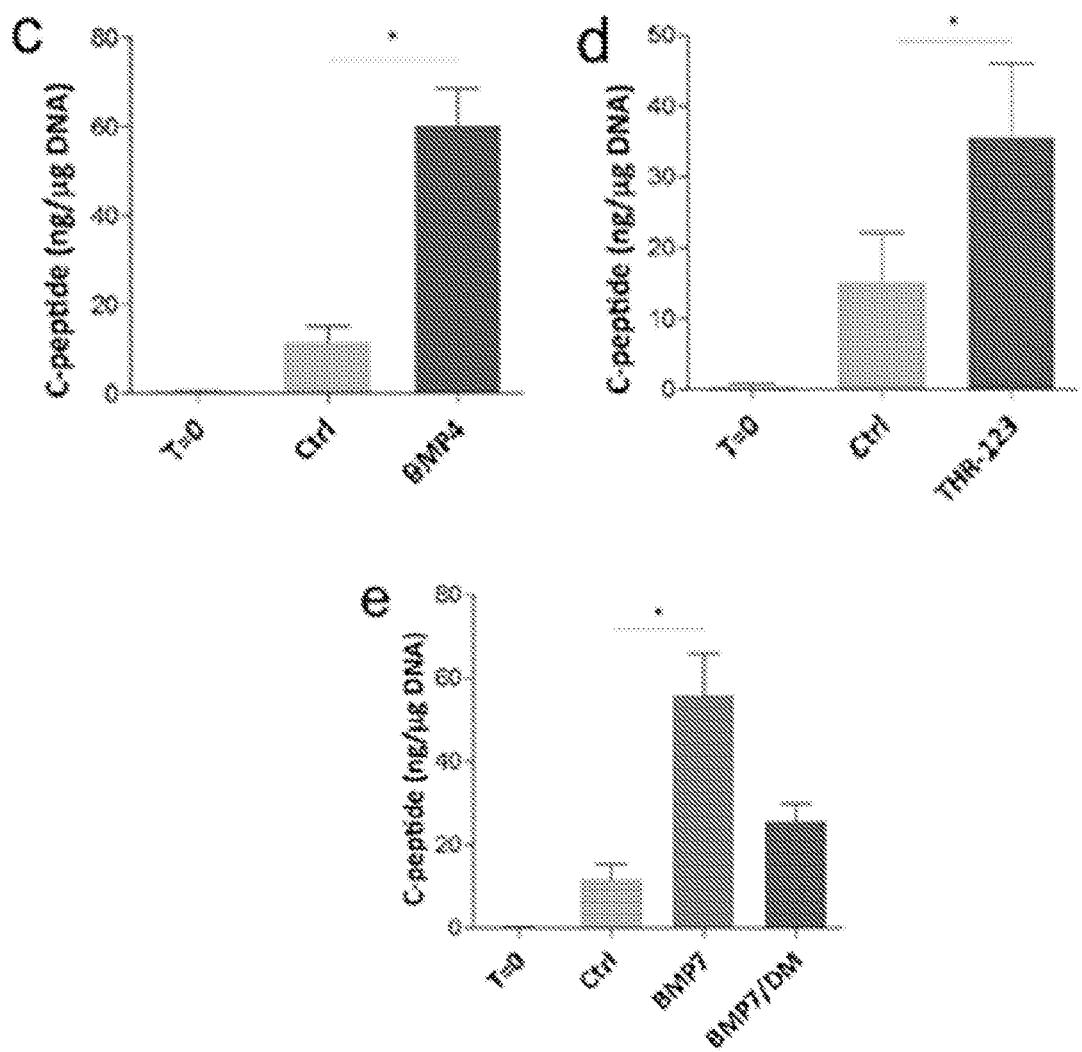

FIG. 2 shows the average total C-peptide (ng/μg DNA) of 8 independent hNEPT preparations (BMP-7-treated and untreated) at the initiation of culture (day 0) and at day 12.

As shown therein, BMP-7 treatment yielded an average increase in C-peptide of two orders of magnitude vs. the initial material.

Example 2

Yield of C-peptide+ Cells and Glucose-Responsive Insulin Secretion

Figure 3:
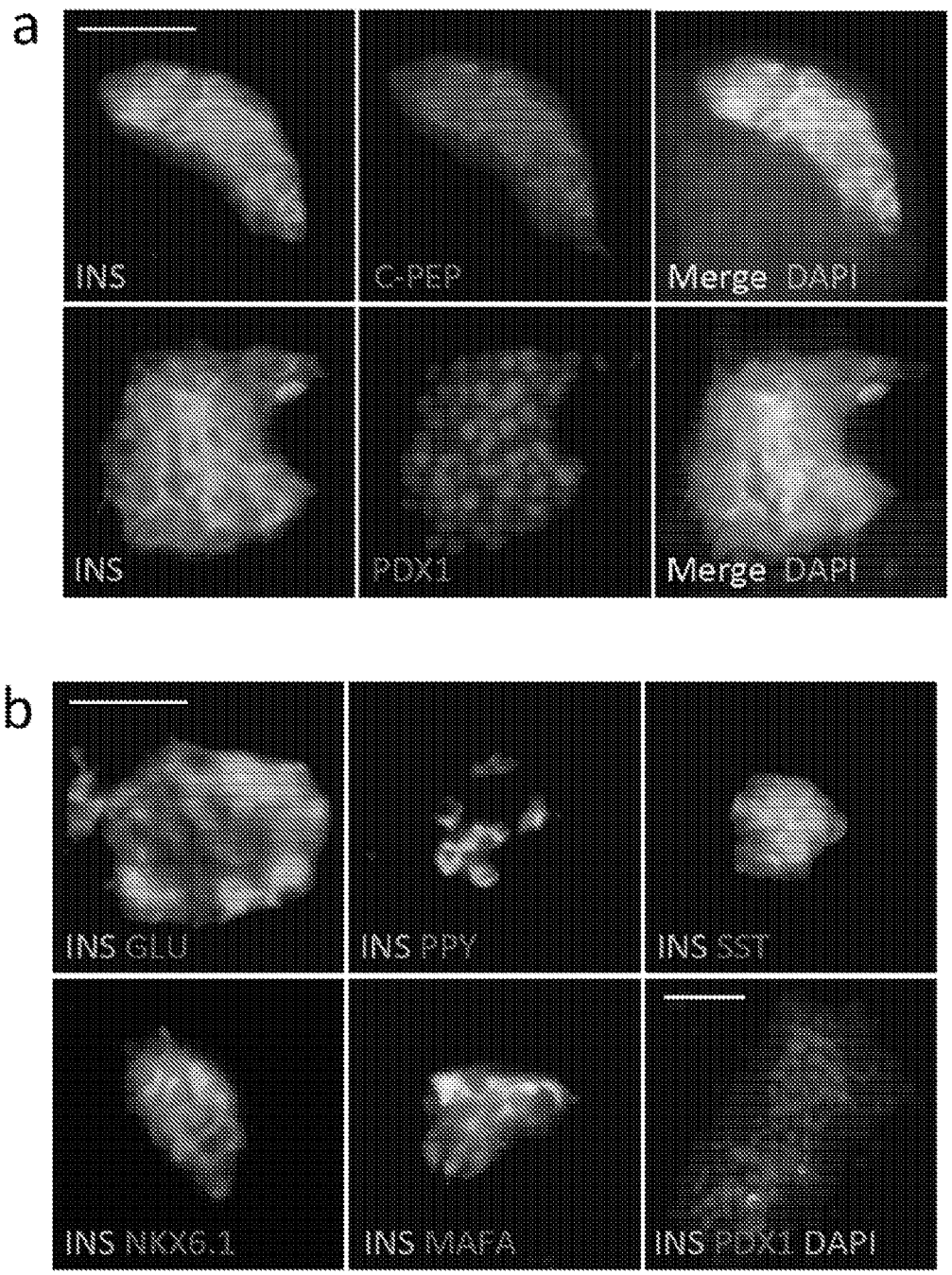
FIG. 3 provides immunofluorescence and functional in vitro analysis of BMP-7-treated hNEPT. (A) Top row: BMP-7-induced cell aggregates co-express insulin (green) and C-peptide (red). Channel merge and DAPI nuclear staining DAPI (blue) are shown at the right. Bottom row: Nuclear PDX1 (red)/cytoplasmic insulin (green). Channel merge and nuclear staining (blue) are shown at the right. Size bar: 50 µm. (B) Top row, from left to right: INS (insulin, green)/GLU (glucagon, red); INS (insulin, green)/pancreatic polypeptide (PPY, red); INS (insulin, green)/SST (somatostatin, red). Bottom row, from left to right: INS (insulin, green)/NKX6.1 (red); INS (insulin, green)/MAFA (red); and INS (insulin, green)/PDX1 (red)/DAPI (blue) in a representative insulin-/PDX1+cluster. Size bars: 50 µm for top row and pictures 1-2 of bottom row. Picture 3 of bottom row: 100 µm. (C) GSIR of control (CTRL) and treated (BMP-7) hNEPT (n=8 preparations). X-axis: L1: low glucose 1 (2.5 mM); H: high glucose (20 mM); L2: low glucose 2 (2.5 mM). Y-axis: human C-peptide (ng/µg of DNA). Data presented as mean +/− standard deviation (n=8). n.s., no significance (P>0.05) (two-tailed paired t-test). Asterisk: statistical significance (P<0.05). (D) Perifusion of untreated (blue line, triangle data points) and treated hNEPT (green line, diamond data points). X-axis: glucose concentration/time (one measurement/4½ minutes): 2.5 G (low, 2.5 mM glucose); 20 G (high: 20 mM glucose). Y-axis: insulin (ng/ml).
Figure 3:
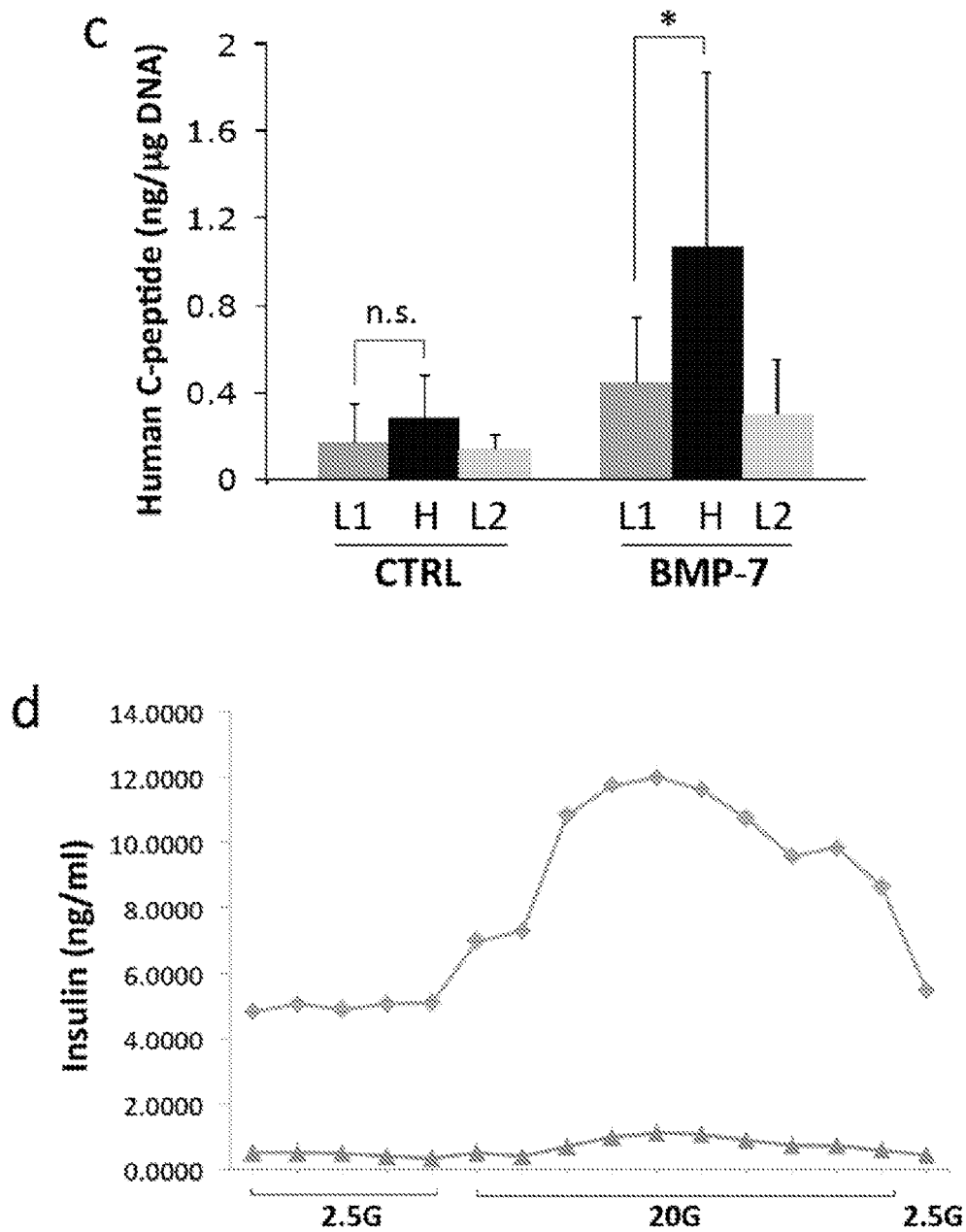

Immunofluorescence characterization of the insulin-expressing clusters was conducted. To rule out potential false-positives derived from the presence of residual insulin in the culture medium, we stained for C-peptide, which is present in pro-insulin and therefore indicates de novo synthesis of insulin. As shown in FIG. 3, most of the cell aggregates presented cytoplasmic insulin/C-peptide and nuclear PDX1. In order to quantify the number of C-peptide+ cells after BMP-7 treatment ImageJ and the FIJI Analyze particles feature was used. Using this software on an average of 12 fields/sample (n=3), the percentage of C-peptide+cells in hNEPT populations after BMP-7 treatment was determined to be 30.43±4.07% vs. 8.15±0.92% in controls (P<0.0001).

Glucagon, somatostatin (SST) and pancreatic polypeptide (PPY) were also observed (FIG. 3b), but none of the four major islet hormones co-localized within the same cell. NKX6.1 and MAFA, two β-cell markers, were also widely observed in insulin+cells. Many other colonies were largely devoid of insulin but most cells exhibited nuclear PDX1 signal (FIG. 3b).

Figure 10:
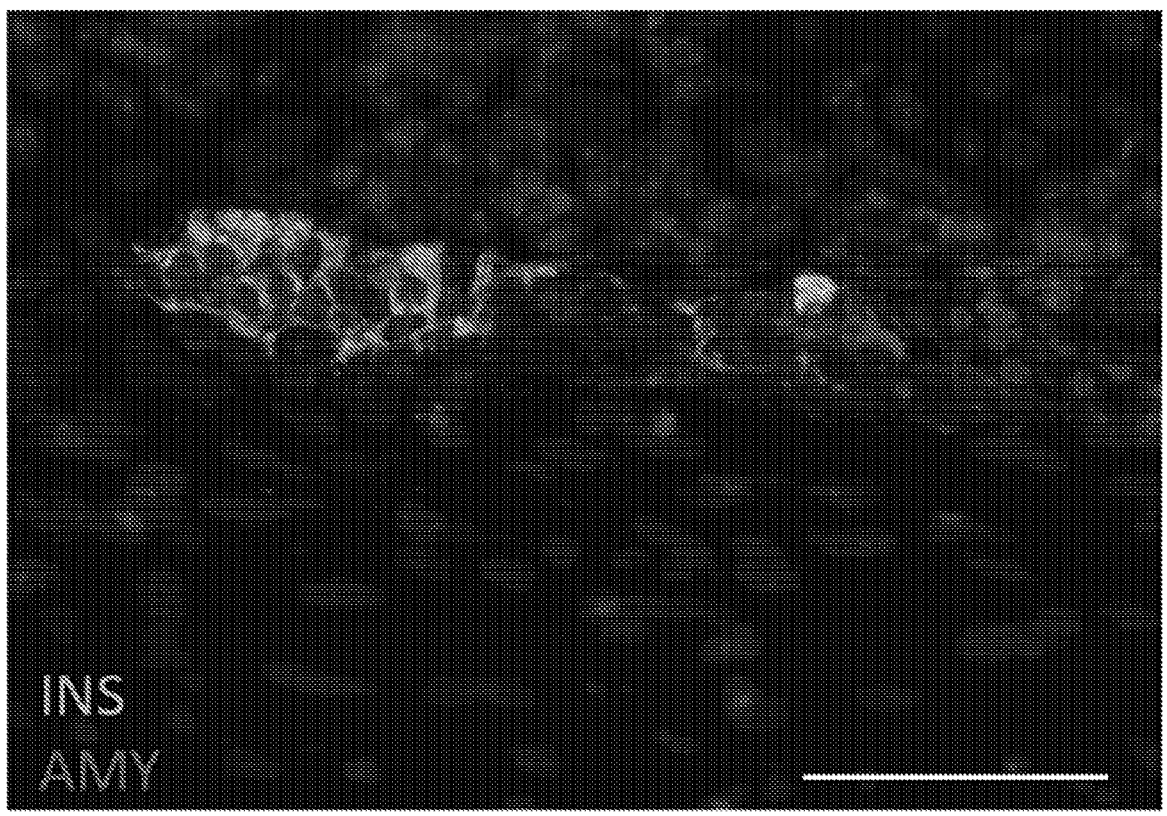
FIG. 10 provides IF analysis of grafts. Insulin (green) and amylase (red) expression in engrafted BMP-7-treated hNEPT (POD 130). Size bar: 50 µm.

Glucose-stimulated insulin secretion (GSIS) and perifusion assays conducted at day 12 showed that BMP-7-induced clusters were glucose responsive (FIG. 3c and FIG. 3d). In order to assess in vivo function, BMP-7-treated and control hNEPT cells were transplanted under the kidney capsule of nu/nu stz-diabetic mice. 3 hNEPT preparations were used (n=5 animals/preparation). 5 additional mice received saline (sham). For each experiment, 4 animals were transplanted with BMP-7-treated cells and 1 with control (untreated, same time point) hNEPT. Intraperitoneal glucose tolerance tests (IPGTT) were performed between post-operative days (POD) 25-39 and subsequently at POD 108-122. No human C-peptide could be detected in the plasma of sham-operated mice or those receiving untreated hNEPTs, either prior or after glucose stimulation. In contrast, mice transplanted with BMP-7-treated hNEPT had up to 230 pM (700 pg/mL) of C-peptide upon glucose stimulation (FIG. 4a). The average glucose stimulation index (SI) was 15.6 (P=0.0064) (FIG. 4b) at POD 25-39 and 43.4 (P=0.034) at POD 108-122. Although no human C-peptide could be detected in 2 out the 12 mice transplanted with BMP-7-treated hNEPT between POD 25 and 39 (#9 and #10), another IPGTT conducted between POD 108 and 122 showed C-peptide for these animals, suggesting that additional maturation may have taken place in vivo. Although the average glucose stimulation index (SI) remained very high (43.43, P=0.034), in most cases human C-peptide values were lower than those between (POD) 25 and 39 (FIG. 4c). Several mice died of causes associated with their genetic background, and the remaining ones were euthanized thereafter. Immunofluorescence analysis of the grafts showed insulin+ cells in close proximity to the exocrine marker amylase (FIG. 10).

Example 3

BMP-7 Induced the Formation of C-peptide+ Cells Through the ALK3/SMAD Pathway In order to study the mechanism behind the effects of BMP-7 on hNEPT preparations, the potential receptors engaged by BMP-7 were studied. BMP-7 binds with high affinity to heteromeric complexes formed by BMPR2 (Bone Morphogenetic Receptor Type II) and the activin-like kinase (ALK) ALK3, ALK6 or ALK2 type I serine/threonine kinase receptors[25]. It was observed that BMP-4, a member of the BMPs family of proteins that signals through ALK3 and ALK6, but not ALK226, induced C-peptide production on hNEPT in a manner comparable to that of BMP-7 (198±62.8–fold vs. 156±32-fold vs. t=0, respectively; n=6, P=0.43), thus suggesting the involvement of ALK3, ALK6 or both in the induction of β-like cell formation. Furthermore, it was observed that THR-123, an ALK3-specific agonist peptide that does not recognize ALK622, also exhibited C-peptide induction potential vs. t=0 within the same range as that of BMP-7 (318±116-fold with THR-123 vs. 261±102-fold with BMP-7; n=4, P=0.25). The results of these experiments suggest that BMP-7 acts through ALK3 in this setting. These findings are consistent with numerous reports that identify ALK3 as the receptor that mediates BMP-7 function in several biological models of regeneration, including adult liver regrowth[23], differentiation of epidermal Langerhans cells[24] and kidney regeneration and fibrosis reversal[22]. The activation of the canonical BMP signaling pathway entails the phosphorylation of SMAD1/5/8 upon ALK3 engagement. As determined by immunofluorescence, ALK3-expressing cells presented SMAD1/5/8 phosphorylation 2 h after the addition of BMP-7 to hNEPT. To further confirm these findings, the use of dorsomorphin (DM), an inhibitor of SMAD1/5/8 phosphorylation, reduced nearly 3-fold the BMP-7-mediated induction of C-peptide compared to t=0 [314.1±152-fold with BMP-7 alone vs. 107.8±34.3-fold in the presence of DM (n=4, P=0.06)]. Taken together, our results indicate that the effect of BMP-7 on hNEPT is chiefly mediated through the ALK3-SMAD1/5/8 BMP canonical signaling pathway.

Example 4

Newly Formed β-Like Cells Arise Mostly from Extrainsular PDX1+ Cells

Figure 5:
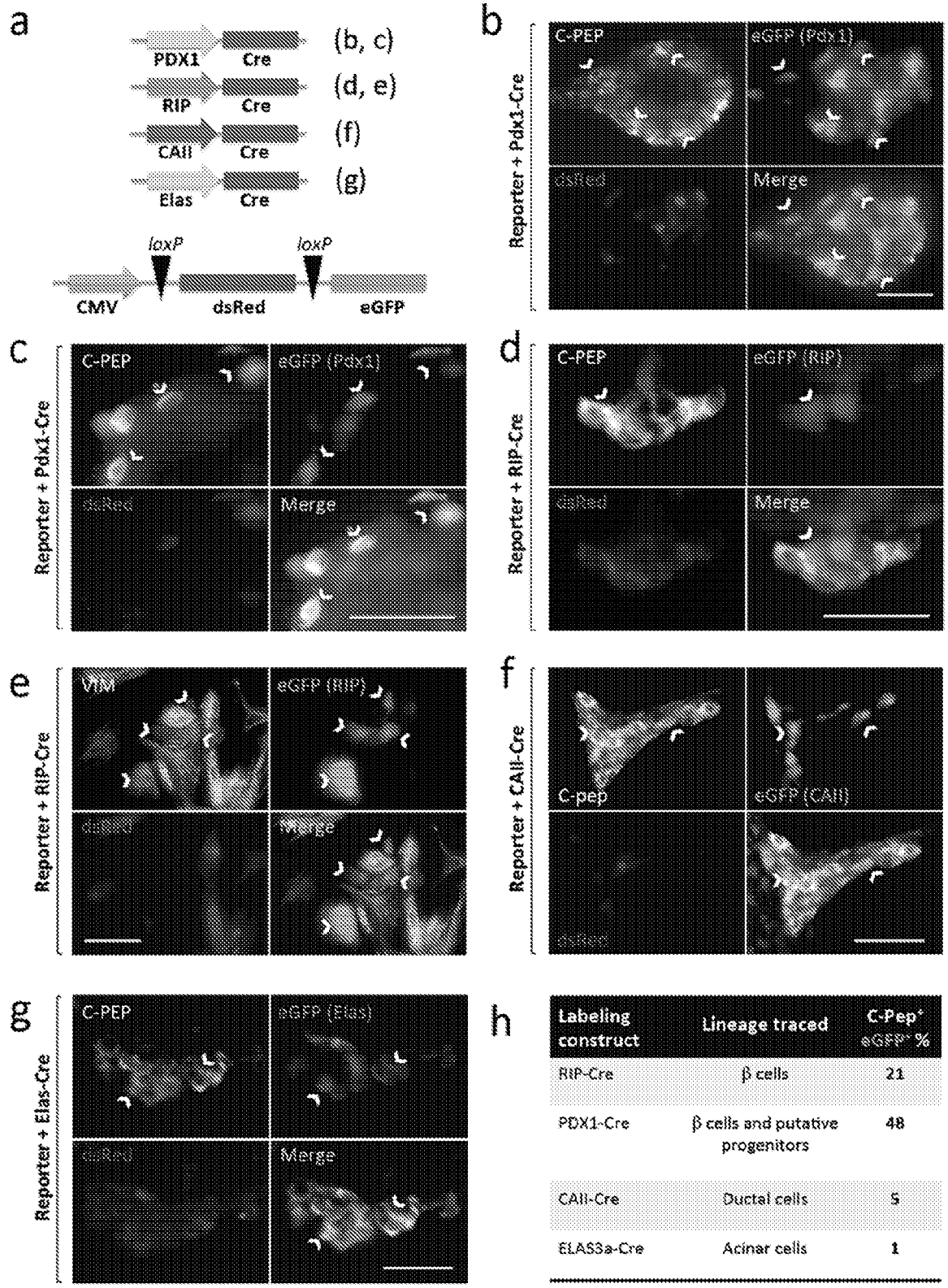
FIG. 5 provides lineage-tracing studies. (A) Tissue-specific promoters (PDX1:β-cells and putative progenitors; RIP: rat insulin promoter, β cells; CAII: carbonic anhydrase II, ductal; ELAS: elastase 3a, acinar) drive Cre expression. The reporter expresses dsRed (red) or eGFP (green) upon Cre-mediated loxP excision. Panels corresponding to each experiment are in parentheses. C-PEP, C-peptide (white); eGFP (green); dsRed (red); and channel merge (DAPI, blue) are shown for all experiments. (B) PDX1-Cre + reporter. Abundant C-peptide+ cells expressed eGFP (white arrows), suggesting a significant participation of PDX1+ cells in BMP-7-induced C-peptide+ cells. Another representative field is shown in higher magnification in (C). (D) RIP-Cre + reporter. A small percentage of RIP-expressing cells contributed to the C-peptide+ population. One such eGFP+/C-peptide+ cell (white arrow) is shown among several other dsRed+/eGFP+/C-peptide+ cells (red arrows). (E) RIP-Cre + reporter. VIM, vimentin (white). Most green cells (white arrows) expressed vimentin, suggesting that residual β cells typically undergo EMT. (F) CAII-Cre + reporter. No C-peptide expression could be detected in any eGFP-tagged (ductal) cells. The red arrow indicates a red, C-peptide+ cell with no eGFP tag. (G) ELAS-Cre + reporter. Several dsRed+/eGFP−/C-peptide+ cells (red arrows) and two eGFP+/C-peptide+ cells (white arrows) are shown. ImageJ-aided quantification of double positives indicated only a marginal acinar contribution to C-peptide+ clusters. (H) Table showing the relative estimated contribution (in %) of each population. Size bars for all panels: 50 µm.

In order to determine the origin of new β-like cells arising upon BMP-7 stimulation, lineage-tracing in fresh hNEPT cultures was performed using viral constructs that impart lineage-specific expression of Cre recombinase. A second (reporter) construct yielded a green fluorescent tag following Cre-mediated excising of a STOP sequence (FIG. 5a). Before excision, transduced hNEPT cell express dsRed. If the relevant lineage-specific promoter is active, Cre excises dsRed out and eGFP is expressed. Constructs with promoters for rat insulin (RIP), carbonic anhydrase II, elastase 3a and PDX1 were generated to tag pre-existing β-cells, ductal cells, acinar cells and putative progenitors/β-cells, respectively. The reasoning behind the use of the latter is that PDX1 expression in non-β-cells has been proposed to be a hallmark of pancreatic β-cell progenitors that may persist after birth in several pancreatic locations in humans[27-29].

The reporter was transduced using a lentivirus for permanent, inheritable expression. However, the lineage-specific constructs PDX1-Cre and RIP-Cre were transduced using adenoviral vehicles for transient expression. This was done because, if constitutively expressed throughout the experiment, the PDX1 and insulin promoters could be re-activated in any de novo-generated β-like cell (thus engaging the reporter and tagging them at that time regardless of their origin). Three independent experiments (n=3) were conducted for these determinations.

The reporter lentiviral construct CMV-LoxP-dsRED-STOP-LoxP-eGFP with adeno PDX1-Cre was used first. At the end of the experiment (day 12), 47.72±5.1% of C-peptide+cells were eGFP-tagged, thus confirming that a large proportion of newly-formed C-peptide+cells derived from cells that were PDX1+ at the beginning of culture (FIG. 5b, c).

If new insulin+ cells arose from pre-existing β-cells (which also express PDX1), the prediction would be that the co-transduction of reporter + RIP-Cre should yield a percentage of tagged C-peptide+ cells similar to that obtained with PDX1-Cre. However, when we conducted this experiment, only 21.05±9.2% of C-peptide+ cells were tagged (FIG. 5d). This observation suggests that there is a smaller percentage of insulin-expressing cells that derive from cells with active RIP at the time of transfection (which may or may not be pre-existing β-cells). 78.62±23.6% of the eGFP+ tagged cells (which expressed insulin at the beginning of the experiment) had become vimentin+ at the end (ImageJ quantification and FIG. 5e), suggesting the occurrence of EMT.

In order to further determine whether BMP-7-responsive cells with the capacity to turn into insulin-producing cells also reside in the ductal tree, lineage tracing with carbonic anhydrase II (CAII)-driven Cre was conducted. CAII has been described as a human pancreatic pan-ductal marker[30]. As shown in FIG. 5f, only 5.4% of C-peptide+ cells had the green tag at the conclusion of the experiment. This result confirms that CAII+ cells have the potential to mature into C-peptide+ cells, but the occurrence of such conversion is rare in this experimental setting.

Finally, as acinar cells have also been linked to endocrine fate reassignment in reprogramming studies[3, 6, 31], an acinar-specific reporter driving Cre was tested. The rat elastase 1 promoter has been used to express genes in pancreatic acinar tissues[32]. However, human elastase 1 is evolutionary silent in the pancreas owing to mutations in the promoter[33]. We thus decided to use the elastase 3a promoter, which is one of the most expressed elastases in human acinar tissues[34]. When the cells were co-transduced with the reporter with an Elas3a-Cre cassette (FIG. 5g), only 1.37% of eGFP+ cells turned out to be C-peptide+, as determined by ImageJ analysis (FIG. 5h).

In summary, results suggest a process in which most BMP-7-induced β-like cells arise from PDX1+ cells that reside in the exocrine compartment. There was a small (CAII) to negligible (Elas3a) contribution of cells that expressed ductal or acinar markers to β-like cells. A significant percentage of C-peptide+ cells derived from cells that expressed insulin at the beginning of the experiment, even though such contribution was still nearly 2.5 fold lower than that observed when tagging PDX1+ cells in general.

Example 5

Figure 6:
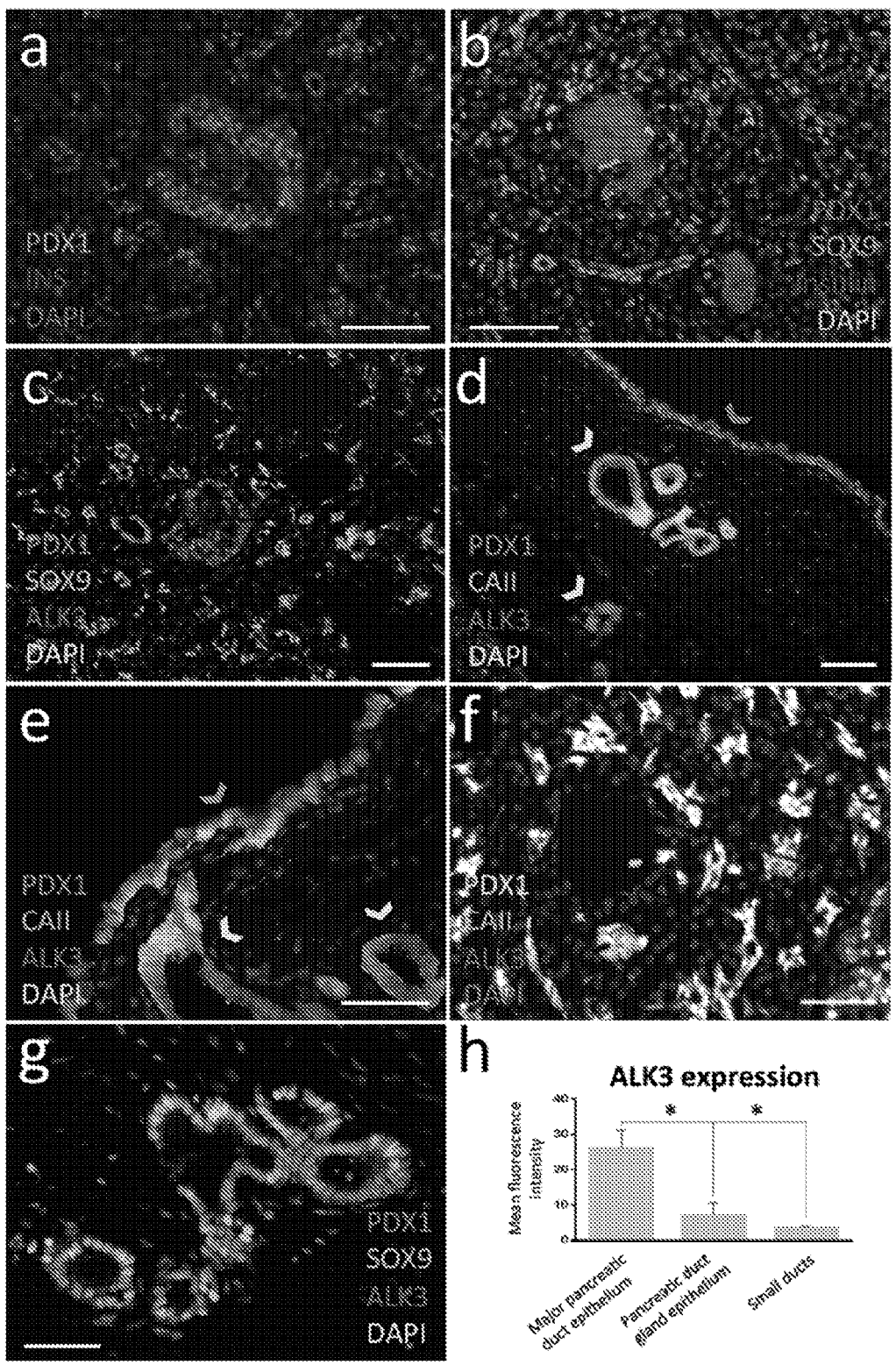
FIG. 6 provides PDX1 patterns of expression in the human pancreas. (A) PDX1 (green) is expressed in insulin-producing β-cells (red) and in exocrine cells. (B) Extrainsular PDX1+ cells are organized in ductal structures. In most, PDX1 (blue) co-localizes with the ductal marker SOX9 (green), yielding a cyan color. (C) Many extrainsular PDX1+ cells co-express SOX9 (green) and the BMP-7 receptor ALK3 (red). Islets (blue PDX1+ nuclei) are ALK3$^-$. (D) The epithelium of the major pancreatic duct (blue arrow) has the largest population of PDX1+/ALK3bright+/CAII$^-$ cells across the organ. Differentially stained PDX1+/ALK3$^-$/CAII+ cells are also present. Pancreatic duct glands (PDGs) within the fibromuscular wall of the major pancreatic duct (yellow arrows) contain comparatively less ALK3bright+ and more CAII+ cells. (E) Higher magnification of the pattern observed in (D). (F) Extrainsular PDX1+/ALK3+ cells within small ducts co-express CAII, unlike those in PDGs and the major pancreatic duct. (G) PDX1/SOX9 staining in ALK3+ epithelial cells within PDGs is heterogeneous, in contrast with the homogeneous pattern observed in small pancreatic ducts, shown in (C). The major pancreatic duct and its PDGs contain ALK3$^+$ cells that are PDX1$^+$ and SOX9dim$^+$ or negative. (H) Quantification of ALK3 expression in the epithelium of the major pancreatic duct, PDGs and intercalated ducts. The Mean Fluorescence Intensity (MFI) is reported as mean±s.d. Differences were significant among all groups (P<0.05). Cells in the epithelial lining of the main pancreatic duct express ALK3 at the highest level detected in the pancreas. Nuclear counterstaining for all panels: DAPI (blue in A; white in B-G). Size bars: 100 µM (A-D); 50 µM (E-G).
Figure 7:
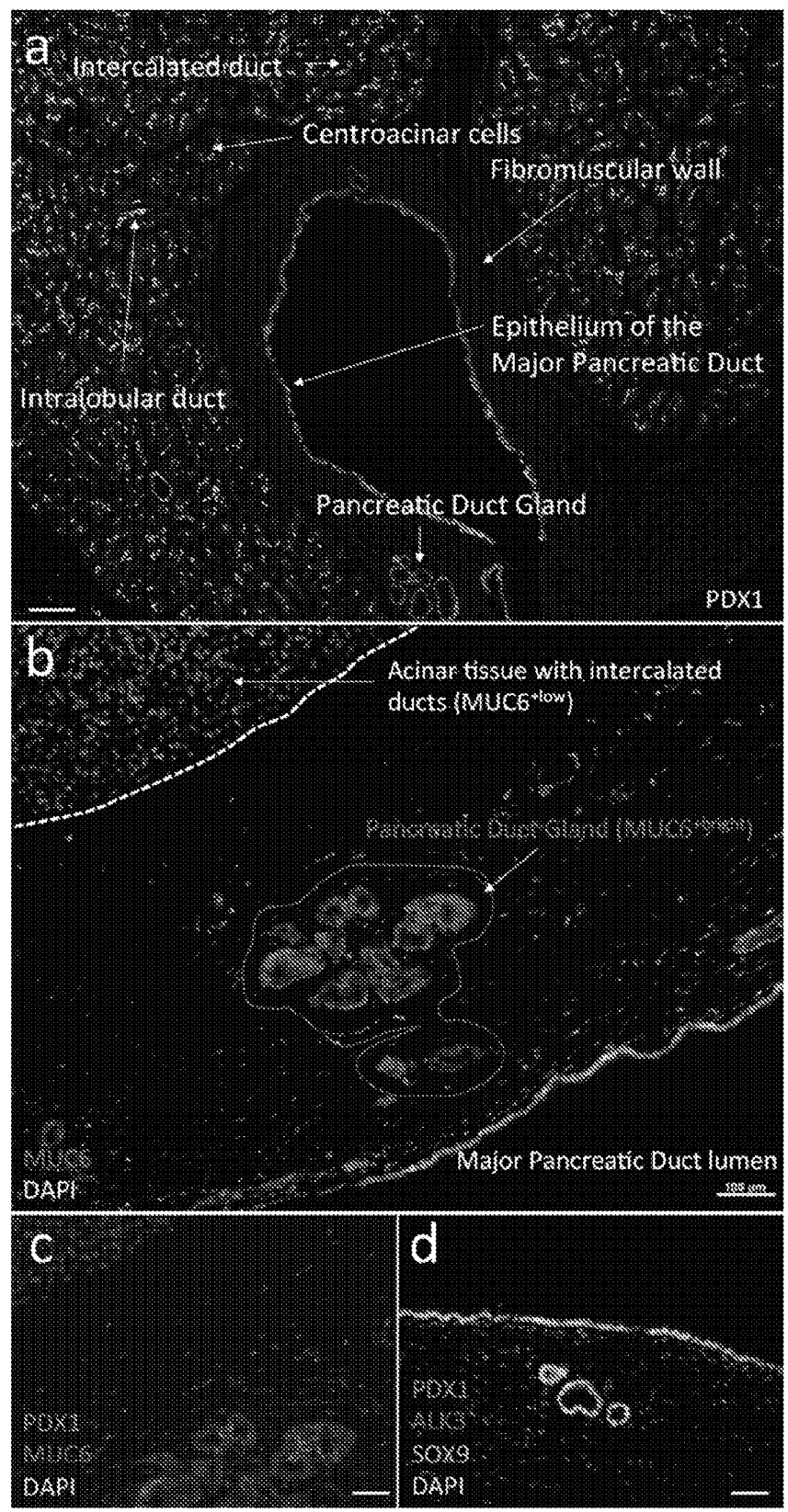
FIG. 7 provides extrainsular PDX/expression patterns. (A) PDX1 expression (white) is shown in a tiled cross-section of the human pancreas. Nuclear PDX1 can be readily detected within the epithelium of the major pancreatic duct, as well as in pancreatic duct glands, intralobular/intercalated ducts and centroacinar cells. (B, C) MUC6 (red) can be used to distinguish between PDX1$^-$ expressing cells (blue in panel C) in intralobular/intercalated ducts/centroacinar cells (MUC6$^{+low}$) and those in pancreatic duct glands (MUC6$^+_{bright}$). Nuclear counterstaining in (B, C): DAPI (white). (D) While SOX9 (green) is co-expressed in virtually all PDX1$^+$ cells within intralobular/intercalated ducts and centroacinar cells (small ducts), both pancreatic duct glands and the lining of the major pancreatic duct contain cells that are PDX1$^+$ and SOX9$^{low}$ or negative. Size bars for all panels: 100 µm.

PDX1+/ALK3+ Cell Distribution in the Non-Endocrine Compartment of the Human Pancreas Our results suggest that BMP-7 induces the conversion of PDX1+ cells that are, for the most part, insulin−. In addition to the PDX1+/hormone+ cells within the islet, PDX1+/hormone−cells are abundant in the non-endocrine compartment of healthy human pancreatic tissues (FIGS. 6a and 7). Two distinct populations of PDX1+ cells could be identified: in ducts of all types (major pancreatic duct, interlobular ducts and small ducts, which in turn comprise intralobular/intercalated ducts and centroacinar cells) and in pancreatic duct glands (PDGs) (FIG. 7). MUCIN 6 (MUC6), a secretable glycoprotein previously associated to non-endocrine PDX1+ cells[12], is highly expressed in PDGs and can thus be used to distinguish the two populations (FIG. 7b, c). In an attempt to further characterize extrainsular PDX1+ populations, SOX9 expression was also. SOX9 is a transcription factor expressed by multipotent PDX1+ pancreatic progenitors at the earliest stages of pancreatic development and by adult pancreatic ductal cells in the mouse[35-37]. Lineage-tracing studies suggest that adult murine Sox9+ cells do not contribute to the pancreatic endocrine lineages[36]. In human pancreatic samples, nuclear SOX9 was detected in the majority of ductal cells (FIG. 6b, c) and some PDG cells (FIG. 6g). However, while nuclear SOX9 and PDX1 co-localized regularly in the cells of small ducts (FIG. 6b, c), their expression was often segregated in PDGs (FIG. 6g) and the major pancreatic duct (FIG. 12).

Results demonstrated that ALK3 co-localized with many extrainsular PDX1+ cells (FIG. 6c-g). In contrast, PDX1-expressing cells within the islets were ALK3− (FIG. 6c).

Figure 11:
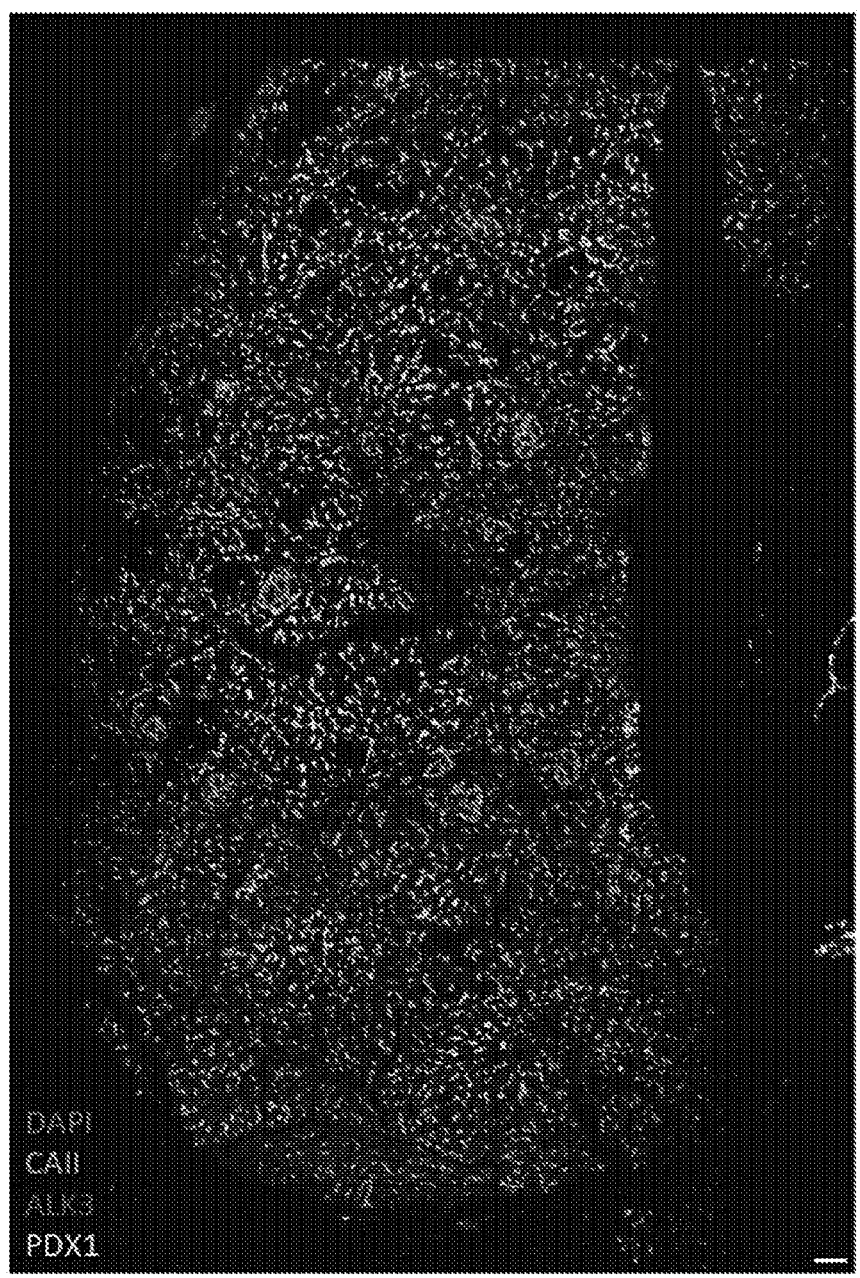
FIG. 11 demonstrates ALK3 co-localizes with CAII in most of the PDX1+ cells of the small ducts. (A) Tiled section of the human pancreas without the major pancreatic duct and associated pancreatic duct glands. Most ductal structures shown in the image are therefore small ducts (intralobular/intercalated ducts and centroacinar cells). Nuclear counterstaining: DAPI (blue). Carbonic anhydrase II (CAII, green), ALK3 (red) and PDX1 (white) are shown. Size bar: 100 µm. (B) ImageJ-assisted quantification of co-localization patterns. Out of 48,189 counted nuclei in this tiled section, 23% were PDX1+. Around 80% of the PDX1-expressing cells were CAII+. Co-localization of PDX1, CAII and ALK3 was observed in approximately 18% of all PDX1+cells. 98% of ALK3+/PDX1+ cells (2,094) were CAII+. Only 2% of the PDX1+/ALK3+ cells (46 in this tile) were CAII−. The PDX1+/ALK3+/CAII− phenotype is rare in small ducts, but it is much more frequently observed in the main pancreatic duct (see FIG. 12).
Figure 12:
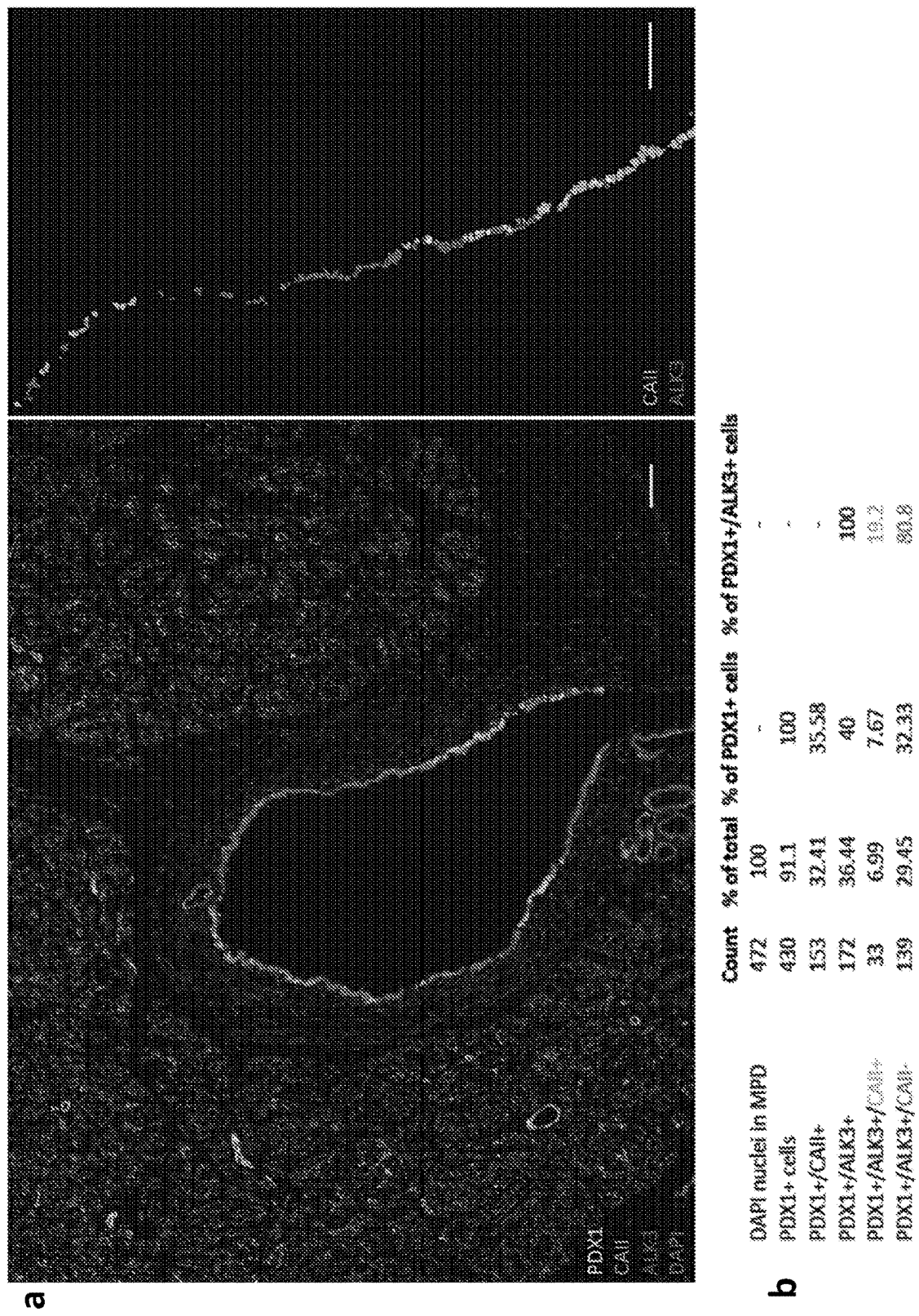
FIG. 12 demonstrates ALK3 and CAII do not co-localize in the majority of PDX1+ cells of the major pancreatic duct. (A) A tiled cross-section of the human pancreas including the major pancreatic duct shows that, unlike the pattern observed in small ducts, the epithelium of the former harbors cells where ALK3 (red) and CAII (green) signals are mutually exclusive. PDX1$^+$ (white)/ALK3$^+$ cells within the major pancreatic duct have the strongest ALK3 signal across the organ (a guide for the identification of the different PDX1$^+$ histological structures is given in FIG. 7a). The right panel shows ImageJ-processed nuclei of PDX1$^+$ cells in the major pancreatic duct epithelium at a higher magnification. The nuclei appear artificially colored in red when corresponding to PDX1$^+$/ALK3$^+$/CAII$^−$ cells, in green when corresponding to PDX1$^+$/ALK3$^−$/CAII$^+$ cells, and in yellow when corresponding to PDX1$^+$/ALK3$^+$/CAII$^+$ cells. (B) ImageJ-assisted quantification of marker co-localization in the major pancreatic duct (MPD) epithelium. Following a pattern opposite to that observed in small ducts (FIG. 11), PDX1$^+$/ALK3$^+$ cells were predominantly (80%) CAII−. Scale bars: 100 µm.
Figure 14:
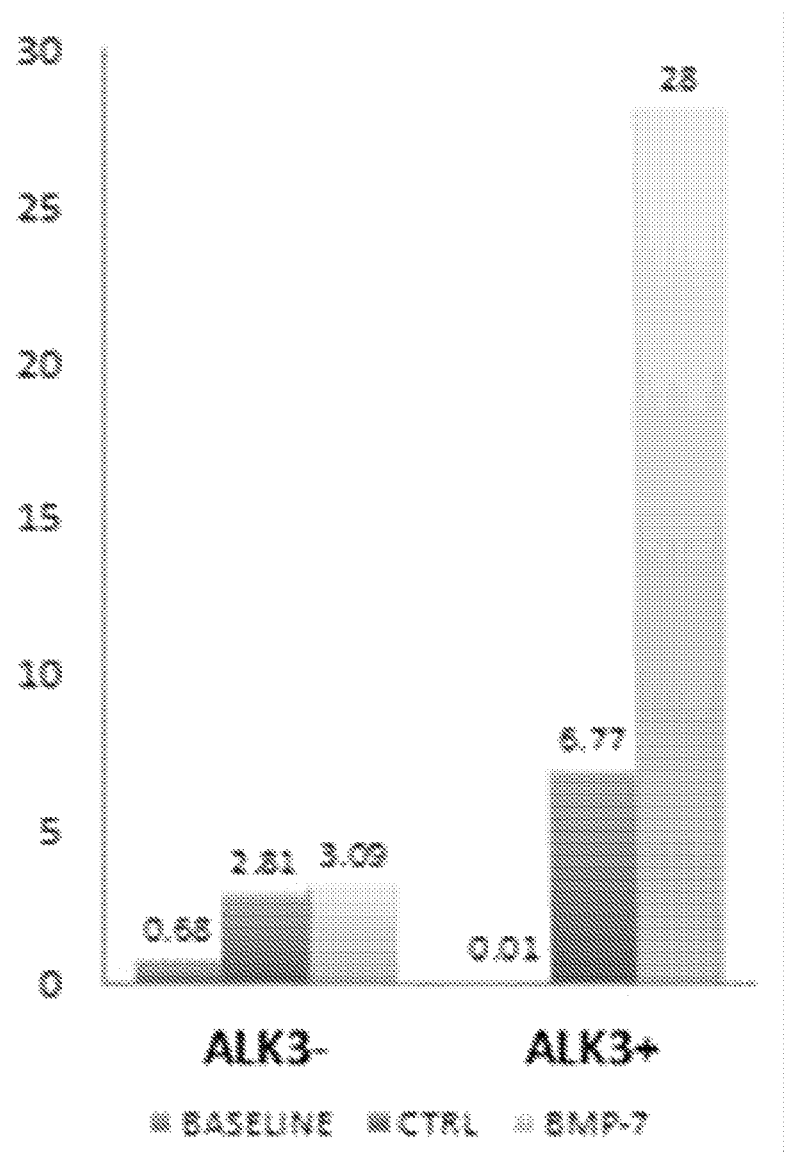
FIG. 14 shows that the ALK3-enriched fraction from hNEPT is BMP-7-responsive in terms of C-peptide production.

Extrainsular PDX1+/ALK3+ cells were abundant both in ducts and within PDGs, with the strongest ALK3 expression found in the major pancreatic duct (FIG. 6d, e, h and FIG. 12). Interestingly, PDX1+/ALK3bright+ cells within the major pancreatic duct and some PDGs were largely negative for the human panductal marker carbonic anhydrase II (CAII)30 (FIG. 6d, e, g and FIG. 12). This is in stark contrast with the pattern observed in small ducts, where almost 100% of the PDX1+/ALK3dim+ cells were CAII+ (FIG. 6f and FIG. 11).

In summary, the histological analysis of the co-expression of PDX1 and ALK3 strongly suggests that BMP-7-responsive putative β-cell progenitors may reside in ductal structures and in pancreatic duct glands. Of note, not all ductal cells were found to express CAII. The observation that populations of PDX1+/ALK3+ cells in the epithelium of the major pancreatic duct (as well as in some PDGs) in which CAII and ALK3 are mutually exclusive. PDX1+/ALK3+/CAII− cells within the major pancreatic duct are also characterized by the strongest ALK3 signal detected across the organ. These observations are aligned with the lineage tracing data, which exclude CAII-expressing cells as a major source of β-like cells upon BMP-7 stimulation.

Discussion

The results shown in Examples 1-5 demonstrate efficient conversion of primary human pancreatic exocrine tissue into functional islet endocrine cells using a simple non-genetic method. Exposure to BMP-7 was sufficient to elicit this conversion, yielding abundant clusters that secreted insulin at higher levels than any exocrine (ductal or acinar) conversion method reported thus far[7,40] and exhibited glucose-responsiveness in vitro and in vivo. The data provided herein suggests that these effects were mediated through the ALK3 receptor, and that the human pancreatic exocrine (but not the endocrine) compartment is rich in PDX1+/ALK3+ cells, lent support to our hypothesis. Indeed, BMP-7 is involved in many biological processes that include stem cell activation and differentiation[43] due to its dual ability to inhibit TGF-β signaling and stimulate the BMP pathway[6, 21].

Indeed, lineage-tracing experiments additionally suggested that new insulin-producing cells arose from a PDX1-expressing sub-population within hNEPT (48% of C-peptide+ cells after BMP-7 treatment were also eGFP+). Parallel experiments in which we tagged cells that expressed insulin at the beginning of culture (such as residual β-cells that may persist in hNEPT after islet isolation, which also express PDX1) yielded nearly 2.5-fold less co-localization of C-peptide and eGFP. These results are therefore consistent with the hypothesis that extrainsular progenitor-like cells are major contributors to newly formed insulin-producing cells in response to BMP-7. The histological distribution of non-endocrine PDX1-expressing cells in the human pancreas, as shown in FIG. 6, strongly suggests a ductal residence. Interestingly, we found that the PDX1+/ALK3+ cells within ductal structures do not always express the ductal marker CAII30. In fact, the cells with strongest ALK3 expression of the pancreas (those of the major pancreatic duct) were shown to be largely CAII- by immunofluorescence. The observation that CAII tagging in the resulting C-peptide+ cells was rather infrequent additionally suggests that PDX1+/ALK3+ CAII- may be the cells that respond to BMP-7 stimulation. Taken together, the results thus suggest that cells with the ability to respond to BMP-7 stimulation may reside chiefly within the epithelium of the major pancreatic duct, and, to a lesser extent, within some PDGs.

Even the relatively lower degree of RIP-Cre labeling in the resulting C-peptide-expressing cells needs to be explained in this context. Rare PDX1+ putative progenitor cells have been previously described within the islet, and their most salient feature was that they expressed low levels of insulin[28, 46]. If the PDX1+ cells described herein also expressed insulin (albeit at levels that rendered it undetectable by immunofluorescence), the observed RIP tagging could be explained not just as persisting β-cells, but also as the result of Cre activity in PDX1+ progenitors where insulin expression goes above a certain threshold. Regarding the small participation (1.37%) of elastase+ cells, the acinar tissue has proven developmentally labile in other settings[3, 5-7, 31, 47].

Transplantation experiments demonstrate long-term engraftment and β-cell function, even if diabetes was not reversed in this animal model. Two hypotheses could explain this observation. First, owing to the limitations of in vitro settings, BMP-7 may have induced an impaired state of maturation that is insufficient to maintain glucose homeostasis in vivo. Similar limitations were found in the hESc field, where earlier attempts at generating β-cells in vitro also yielded cells with high insulin levels but unable to reverse diabetes in vivo[48]. These results led to the current approach in which hESc are transplanted at the pancreatic progenitor stage for in vivo maturation[49]. Even with the most recent refinements (which have been erroneously interpreted as the end of the quest for functional β-cells in vitro[50, 51]) these cells may still require a significant degree of maturation to happen in the host: in one of such studies, it took 40 days for the cells to achieve competence upon transplantation in diabetic mice[50]. In the other, the reversal of already established diabetes was not even attempted[51]. The second hypothesis is exocrine contamination. Graft analysis revealed exocrine cells in close proximity to endocrine ones (FIG. 10). Proteases from acinar tissue contamination impair islet viability both in vivo and in vitro, and anti-proteases were shown to rescue function[52]. Transplantation outcomes might therefore be improved by purification of the endocrine fraction prior to transplantation.

It must be noted that a high degree of variability was observed in the ability of individual hNEPT preparations to give rise to colonies and the extent to which they produced insulin. This is hardly surprising in view of the limitations that are intrinsic to the study of primary human pancreatic tissue, which include donor age, sex and weight, organ ischemia time, length of tissue digestion and yield. Additional experiments to establish quality control parameters prior to treatment are a current priority in our laboratory.

Methods for Examples 1-5 hNEPT culture: Human islets were isolated at the DRI's cGMP facility following methods already described54, and hNEPT samples (2-4 ml) were obtained as an isolation byproduct. The cells were washed and seeded on tissue culture-treated plates in FBS- and trypsin inhibitor-supplemented RPMI 1640 medium (Gibco-Life Technologies, Grand Island, N.Y.). After 48 h, floating cells were removed with fresh medium replacement. The following day, cultures were either treated with 100 ng/ml BMP-7 (ProSpec-Tany TechnoGene; Ness Ziona, Israel) or remained in the starting medium as controls. Cells were allowed to grow 4-5 days and then the serum-containing medium was replaced by serum-free Advanced RPMI 1640 (Gibco-Life Technologies, Grand Island, N.Y.). Four to five days later the cells were either subjected to static incubation to evaluate their ability to respond to changing glucose concentration or collected for further assessments (such as C-peptide content, immunohistochemistry or cellular composition) or transplantation.

Real-time colony growth assessment: In order to observe the formation and growth of the colonies we used an IncuCyteZOOM EssenBiosciences instrument (Ann Arbor, Michigan) within a Symphony Incubator purchased from VWR (Atlanta Ga.). The cells remain in their own culturing flask or plate, where growth can be observed and quantified over time. The information is gathered automatically either by phase contrast imaging or with green or red fluorescent filters. The objective size can be set at 4×, 10× or 20×. Our data was collected with a 10× objective over the entire flask every 6 hours for the duration of the 12 day culture. The frequency of data collection can be set up to 2000 images/hour.

IF analysis and confocal microscopy: The present study was conducted on human pancreatic samples from cadaveric organ donors. In addition to our own cGMP facility, the Network for Pancreatic Organ Donors with Diabetes (nPOD, www.jdrfnpod.org)55 also provided tissue sections. For IF staining, 5 µm-thick frozen sections or cultured cells were fixed with 4% paraformaldehyde (PFA) for 20 min at room temperature, rinsed with HBSS, washed (3 x 5 min each) with 1x Supersensitive Wash Buffer (Biogenex HK583-5K) and then incubated in permeabilization buffer PBSTr [0.2% Triton X-100 (Sigma-Aldrich) in PBS] for 30 min at room temperature. To prevent non-specific antibody binding, cells were incubated at room temperature in 1× Universal blocking buffer containing 0.1% Triton X-100 and 5% serum originating from the same species as the secondary antibody [mouse, goat, rabbit (Invitrogen), or donkey (Jackson ImmunoResearch Laboratories Inc., West Grove, Pa.)]. Double/triple IF staining was carried out by incubating cells simultaneously in the mixture of two or three primary antibodies diluted with blocking buffer in a humidified chamber overnight at 4° C. After decanting and washing (5×10 min each) in PBS containing 0.01% Triton X-100, the cells were incubated in the mixture of two or three secondary antibodies (raised in different species and labeled with different fluorophores) diluted with blocking buffer in a humidified chamber for 1 hour in the dark at room temperature. Decanting, PBS washing and counterstaining with 2-(4-amidinophenyl)-1H-indole-6-carboxamidine (DAPI) (1 µg/ml) (Santa Cruz Biotechnology, Santa Cruz, Calif.) were done protected from light. For all experiments, control reactions included: (1) the omission of the primary antibody; (2) the replacement of the primary antibody with the appropriate isotype-matched irrelevant antibody; and (3) the omission of the secondary antibody. The stained cells were covered with PBS and stored in the dark at 4° C. until the images were acquired. Slides were mounted in Vectashield (Vector Labs, Calif.). Antibodies used are listed in FIG. 13.

For fluorescence imaging, Leica DM IRB (Leica Microsystems, Bannockburn, Ill.), Zeiss ApoTome Axiovert 200M and Zeiss LSM510 confocal microscopes were used. Images were acquired digitally using a high-resolution B/W CCD digital camera ORCA-ER (Hamamatsu Corp., Bridgewater, N.J.).

Imaging analysis: For general quantification purposes (e.g., percentage of C-peptide+ cells) we used ImageJ and the FIJI Analyze particles feature. Background was subtracted from each channel, as autofluorescence is a common concern when working with pancreatic tissues. Images were then binarized for quantification. The Watershed function was used on the DAPI channel to separate touching nuclei, which were subsequently counted by the Analyze particle command. Subsequently, we detected nuclei that were overlapping with C-peptide+ areas using the AND operator under the Image calculator feature of FIJI. Finally, we quantified the number of nuclei in the overlap area and calculated the ratio of the overlapping nuclei against the total nuclei.

For co-localization studies (e.g., lineage tracing), after background subtraction and binarization the area overlap between the eGFP and C-peptide channels was calculated by the AND operator in FIJI ImageJ. We subsequently calculated the ratio of overlap over the eGFP area and expressed it as percent value.

Larger pancreatic section images were acquired on a Leica SP5 confocal microscope using a "tiling" technique. A whole pancreatic section of approximately 3×4.5 mm (corresponding to around 100 slides) was tiled using x40 1.25 NA oil immersion lens at a 378 nm pixel size sampling rate. Planes were acquired at approximately 1 µM z-step size from the 8 µM section, and subsequently merged utilizing the maximum intensity projection algorithm. For quantification of ALK3/PDX1/CAII co-expression, separate channels were converted to binary images, and the number of nuclei was estimated with the FIJI Analyse Particle plugin.

The expression of ALK3 protein was calculated by quantitative immunofluorescence microscopy on transverse sections of the human pancreas neck. The Main Pancreatic Duct, its Pancreatic Duct Glands (in its fibromuscular wall) and the Intercalated Ducts were mapped by histological presentation and by MUC6 staining in serial sections. Double immunofluorescence staining was performed to detect ALK3 and PDX1. Fluorescence signal was acquired with uniform settings and exposure time using a Zeiss AxioVert 200M ApoTome and the ActioVision application. Multiple fields per sample (n=12) at 20× magnification were acquired, and a uniform linear threshold applied. Data were exported as 8-bit RGB merged and single-channel files and processed with ImageJ. The areas corresponding to PDX1+ cells in the epithelium of the Major Pancreatic Duct, of the Pancreatic Duct Glands and of the Intercalated ducts were selected. The Mean Fluorescence Intensity (MFI) of the ALK3 staining was obtained in the areas selected, and expressed in Arbitrary Units on a scale from 0 (no signal in a pixel) to 255 (maximum signal in a pixel). The resulting dataset was analyzed with GraphPad Prism. Variance was determined with 1 way ANOVA with Tukey's multiple comparisons test to determine the differences among the MFIs of the three tissues.

Flow cytometry: After isolation, the acinar tissue is washed twice in RPMI medium containing 10% FBS (Life Technologies; Carlsbad Calif.) and 100 µg/ml trypsin inhibitor (Sigma/Aldrich St Louis Mo.) and once with PBS. In order to obtain single cell suspension the tissue is subjected to additional digestion for 15 min at 37° C. with Accutase (Innovative Cell Technologies, San Diego, Calif.). After two washes with PBS, the cells are incubated at 40 C for 30 min in PBS containing Live/Dead fixable stain (dilution 1:1000) (Molecular Probes/Life Technologies, Eugene, Oreg.). Cell surface antigens are detected after three additional PBS washes either by direct method of 30 min incubation with PE conjugated antibody CD105 (dilution 1:20) (StemCell Technologies, Vancouver, BC, Canada) or indirectly two times 30 min incubation and two washes in between with the ductal cell marker mouse monoclonal antibody CA19-9 dilution 1:100 (Leica Microsystems, UK) and ALK3 mouse monoclonal antibody recognizing BMPR1A/ALK3 receptor (dilution 1:50) (LifeSpan Biosciences, Seattle Wash.). The conjugated secondary antibodies Alexa Fluor 488 or 568 (Molecular Probes/Life Technologies, Eugene, Oreg.) were used at 1:500 dilution 30 min. After the final two washes, the cells were fixed and permeabilized with Fix/Perm buffer (BD Biosciences, San Jose, Calif.) following manufacturer's instructions. All staining incubations as well as fixation/permeabilization were carried out at 40C.

After fixation/permeabilization treatment, the cells were washed twice with Wash/Perm buffer and stained using FITC-conjugated anti-Amylase antibody (1:250) (Abcam, Cambridge, Mass.), Insulin APC (Allophycocyanin)-conjugated antibody (1:10) (R&D Systems; Minneapolis, Minn.) and PDX1 conjugated with eFluor660 (1:20) (eBiosciences, San Diego, Calif.). Two washes with Perm/Wash medium concluded the staining procedure. The stained cells were resuspended in FACS buffer (PBS + 1% BSA and 0.01% sodium azide) and evaluated on a BD LSRII instrument with FACSDiva 8.0.1 software.

Quantitative Real Time RT-PCR: Samples were washed in PBS and resuspended in RNA later (Life Technologies—Ambion, Grand Island, N.Y.). RNA was extracted with the mirVana kit (Life Technologies-Applied Biosystems, Grand Island, N.Y.). 2 ng/µl of RNA was used for cDNA synthesis using High-Capacity cDNA Kit (Life Technologies-Applied Biosystems, Grand Island, N.Y.). Quantitative RT-PCR was performed with TaqMan assays (Life technologies—Applied Biosystems, Grand Island, N.Y.) following manufacturer's instructions. RNA expression was calculated as Relative Quantification (RQ) by Applied Biosystems software using the formula RQ=2−ddCT (ddCT=dCT of the sample−dCT of the control). dCT is the number of cycles normalized by endogenous control. Individual reactions were performed with a 7500 Fast Real Time PCR system (Life Technologies). Some experiments were performed using custom-made Taqman® Low Density Microarray (TLDA) cards containing 43 target genes and 3 endogenous genes (ubiquitin C, 18S rRNA and beta actin) and ran in a 7900 Real time PCR cycler (Life Technologies). Cts >35 were considered undetermined.

Lineage-tracing: Lineage tracing was performed in fresh cultures utilizing the reporter lentiviral construct CMV-LoxP-dsRED-STOP-LoxP-eGFP (kindly provided by Dr. P. Ravassard, Hôp. Pitié-Salpétrière-Paris) with CAII-Cre lentivirus, Elas-Cre lentivirus, Adeno-RIP-Cre and Adeno PDX1-Cre to tag ductal, acinar, insulin and progenitor cells, respectively. Owing to the fact that PDX1 and RIP would be re-expressed in any de novo-generated β cell (thus tagging them regardless of their origin), adenoviral vectors for transient expression were used for PDX1-Cre and RIP-Cre. For acinar and ductal tagging, this was not a concern, and therefore CAII-Cre and Elas-Cre were cloned into the second-generation vector pLenti-MP2. The CAII and ELA3A promoters were amplified by PCR from the plasmid pLightSwitch 5709333 and 5703278 (Switchgear Genomics), respectively. The 1614-4531 region of the mouse PDX1 promoter (AF192495), containing the regulatory sequences directing β cell expression[56] (which have been previously shown to be active in human β-cells[57]), was cloned by PCR from DNA isolated from liver tissue. The Cre domain was amplified by PCR from the plasmid pGD89 (Addgene). The recombinant lentivirus was produced by the University of Miami Viral Vector Core Facility. Adeno RIP-Cre and Adeno PDX1 Cre were produced in an adenovirus serotype 5 with E1/E3 deletion (Vector Biolabs). hNEPT cultures were transduced with equal amounts of reporter and Cre constructs. At the end of stage 3, the cells were first examined microscopically for expression of red and green fluorescence and then evaluated by immunofluorescence (chiefly C-peptide expression co-localizing with dsRed or eGFP).

Animal procedures: All animal procedures were conducted following protocols approved by the University of Miami's IACUC at the Preclinical Cell Processing & Translational Models Core of the Diabetes Research Institute. Male nu/nu mice (Taconic) were rendered diabetic with a single injection of streptozotocin (STZ) (200 mg/kg) and considered diabetic when 3 consecutive glucose readings were above 250 mg/dl. An insulin pellet (Linplant, LinShin Canada Inc., Toronto, ON) was placed subcutaneously for glucose homeostasis support. No general anesthesia was required for this procedure.

Mice with sustained hyperglycemia (>300 mg/dl) received human NEPT (control or BMP-7 treated) under the kidney capsule. Under general anesthesia, a small lateral incision was made through the skin and fascia of the peritoneal cavity. The left kidney was externalized and a small puncture made in its capsule. NEPT (1-2×107 cells) were gently injected under the kidney capsule in a minimal volume of saline. The muscle/fascia was sutured and the skin closed with surgical staples. Mice were placed on a warm pad and buprenorphine was administered subcutaneously for pain management twice a day for 3 days. Blood glucose was checked daily for 10 days and then twice a week afterwards.

For the detection of human C-peptide, animals were fasted (~2-4 h), and at the end of the fasting period an IP bolus of glucose (2.0 g per kg body weight) administered. Blood samples from the retro-orbital plexus were obtained first after the fasting period and then one hour after the glucose bolus, under general anesthesia. Human C-peptide levels in plasma were measured with the Ultrasensitive Human C-peptide ELISA kit (Mercodia, Uppsala, Sweden) according to manufacturer's instructions.

Glucose-stimulated insulin release (GSIR) and total insulin determination: GSIR was performed in six-well plate cultures. BMP-7-treated samples and untreated controls were washed twice with DMEM medium containing 2.5 mM glucose (Low glucose medium or L-medium). Upon addition of 2 ml of the same medium, the cells were cultured for 1 h at 37° C. to bring their insulin secretion to baseline. After 2 more washes, 1 ml of L-medium was added and the cells were returned to the incubator for 1 h. At the end of incubation period, the medium was collected and the cells exposed for 1 h to 1 ml of 20 mM glucose DMEM medium (high glucose medium or H-medium). After the collection of the H-medium supernatant, the cells were washed three times with L-medium and cultured again in low glucose conditions for 1 h. As before, supernatant was collected at the end of the incubation period. The second low glucose incubation is necessary to confirm that the cells are responding to glucose concentration changes in a physiological manner and not dumping insulin. After the last incubation, the cells were collected, washed in PBS and lysed with 1 ml of T-Per (Thermo Scientific, Rockford, Ill.). The lysates and the supernatants from GSIR test were evaluated with ELISA for C-peptide content (Mercodia, Uppsala, Sweden) following manufacturer's instructions. DNA content of the lysates was used to normalize the results (Pico-Green dsDNA Assay Kit, Life Technologies-Molecular Probes, Grand Island, N.Y.).

Perifusion studies: Perifusion was performed as described58. In short, a high-capacity automated perifusion system, originally developed to assess islet function, was used to dynamically measure insulin secretion of hNEPT. A low-pulsatility peristaltic pump pushed HEPES-buffered solution (125 mM NaCl, 5.9 mM KCl, 2.56 mM $CaCl_2$, 1 mM $MgCl_2$, 25 mM HEPES and 0.1% BSA, pH 7.4) at a perifusion rate of 100 µl through a column containing NEPT immobilized in Bio-Gel P-4 Gel (Bio-Rad, Hercules, Calif.). Glucose concentration was adjusted to 2.5 (L) or 20 (H) mM. Stimuli were applied along with the perifusion buffer. The eluate was collected in an automatic fraction collector designed for a 96-well plate format. The column containing the acinar cells and the perifusion solutions were kept at 370C, and the eluate in the collecting plate was kept at <40C. Eluates were collected every 4½ minutes. Insulin release was determined with the Human Insulin ELISA Mercodia Kit (Uppsala, Sweden) following the manufacturer's instructions.

Statistics: GraphPad Prism version 5 was used for statistical analysis. Following the Shapiro-Wilk normality test, statistical differences between groups were calculated by two-tailed paired t test or Wilcoxon signed rank test. $P \leq 0.05$ was considered to be significant. Results are expressed as mean±standard deviation.

Example 6

BMP-7 Responsive Cells are $ALK3^+$ Cells

Previous studies suggest that BMP-7 engages the ALK3 receptor in hNEPT, and lineage tracing determined newly created C-peptide$^+$ cells that rose from cells that expressed ALK3. An adenoviral ALK3-Cre construct is used to permanently tag ALK3-expressing cells, alongside the lentiviral reporter. The fidelity of the promoter was confirmed by ALK3 tagging and subsequent ALK3 staining of tagged cells. The results (n=4 independent hNEPT) show abundant (59±7%) GFP tagging in the C-peptide$^+$ cells that arise after BMP-7 treatment (data not shown). Taken along with the lineage tracing data[17] provided in Example 4, and these results suggest that most BMP-7-induced β-like cells arise from $PDX1^+/ALK3^+$ cells.

Example 7

Figure 17:
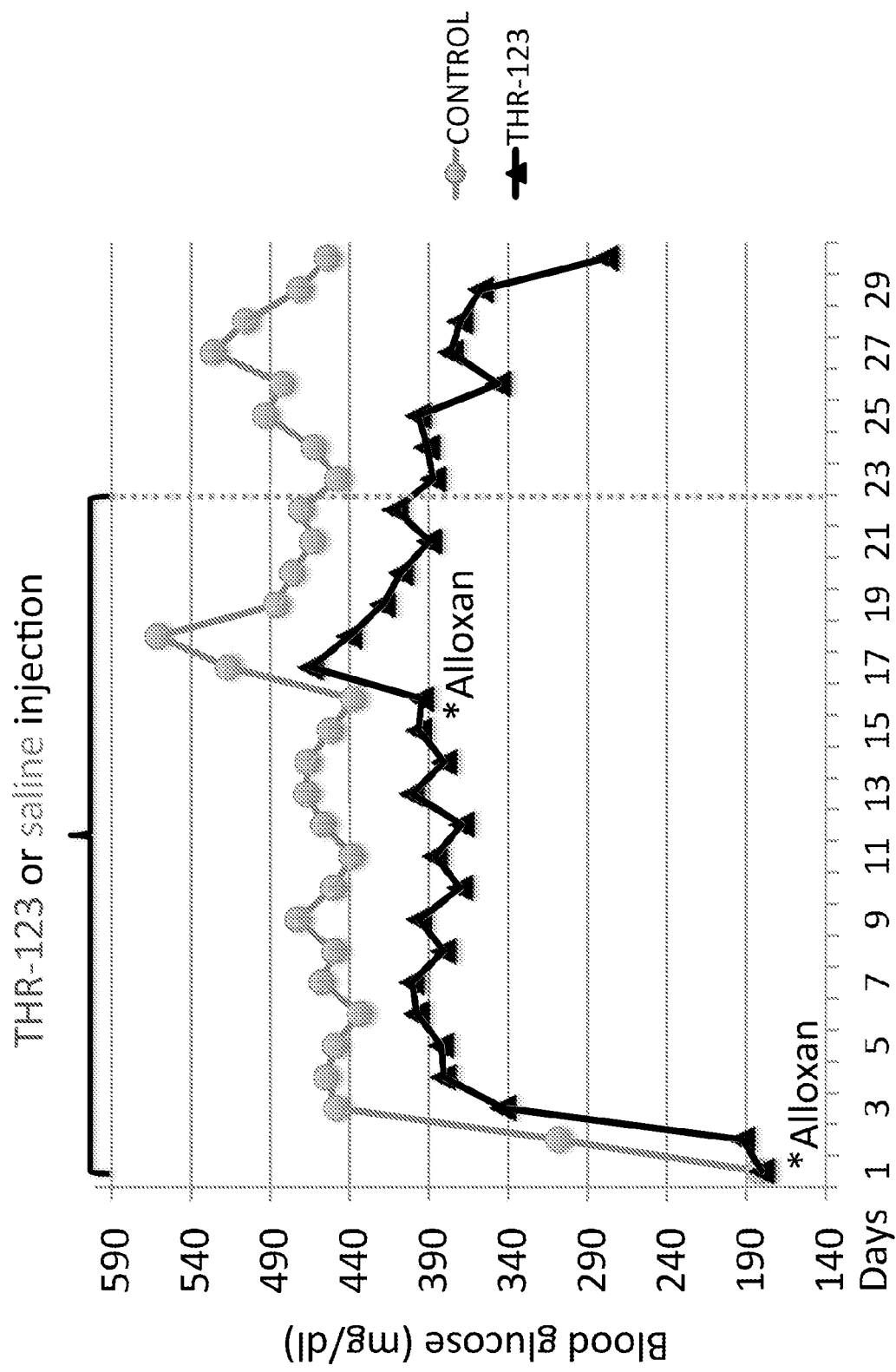
FIG. 17 shows the change in blood glucose concentration in alloxan-treated mice injected with either THR-123 or saline. X axis: Time (days) after first alloxan injection. Y axis: Blood glucose levels (mg/dl). Injection of THR-123 (a BMP-7 analog and ALK3 receptor agonist) into alloxan-treated diabetic mice was done for 23 days. Controls were injected with saline. At day 23, injections were stopped in both controls and experimental groups. Hyperglycemia was further reduced in the THR-123 group from that point on (see trend line).

Live BMP-7-Responsive Cells can be Sorted from hNEPT Using ALK3 and a Novel PDX1 Surrogate Marker Magnetic bead-based methods (Miltenyi) were used for the enrichment of ALK3+ cells from hNEPT. Both enriched and negative fractions are subsequently plated and treated with BMP-7 or left untreated (controls). As shown in FIG. 17, only the ALK3-enriched fraction is BMP-7-responsive in terms of C-peptide production. ALK3 antibody used for enrichment does not render the receptor ineffectual (at least not permanently) for subsequent BMP-7 engagement.

BMP-7-responsive progenitor-like populations are characterized by the expression not only of ALK3, but also PDX1. New surrogate surface markers for nuclear PDX1 are defined by bioinformatics analyses. A published dataset[42] was interrogated with the transcriptome of the major pancreatic populations. Gene Set Enrichment Analysis software was applied on a matrix of expression data obtained from the datasets E-MTAB-463 and -46542. The PDX1 expression profile was used as continuous phenotype labels and the Pearson's correlation as the metric to select which genes showed concordant or opposite expression patterns with PDX1. PDX1 was found to be associated with P2RY1, a purinergic receptor that mediates the action of extracellular nucleotides. Antibodies that recognize the external domain of P2RY1 are commercially available. Results indicated that P2RY1 is co-expressed with PDX1 (mostly associated with ducts) in the human exocrine pancreas (data not shown). These results represent a validation of a bioinformatics analyses.

Figure 15:
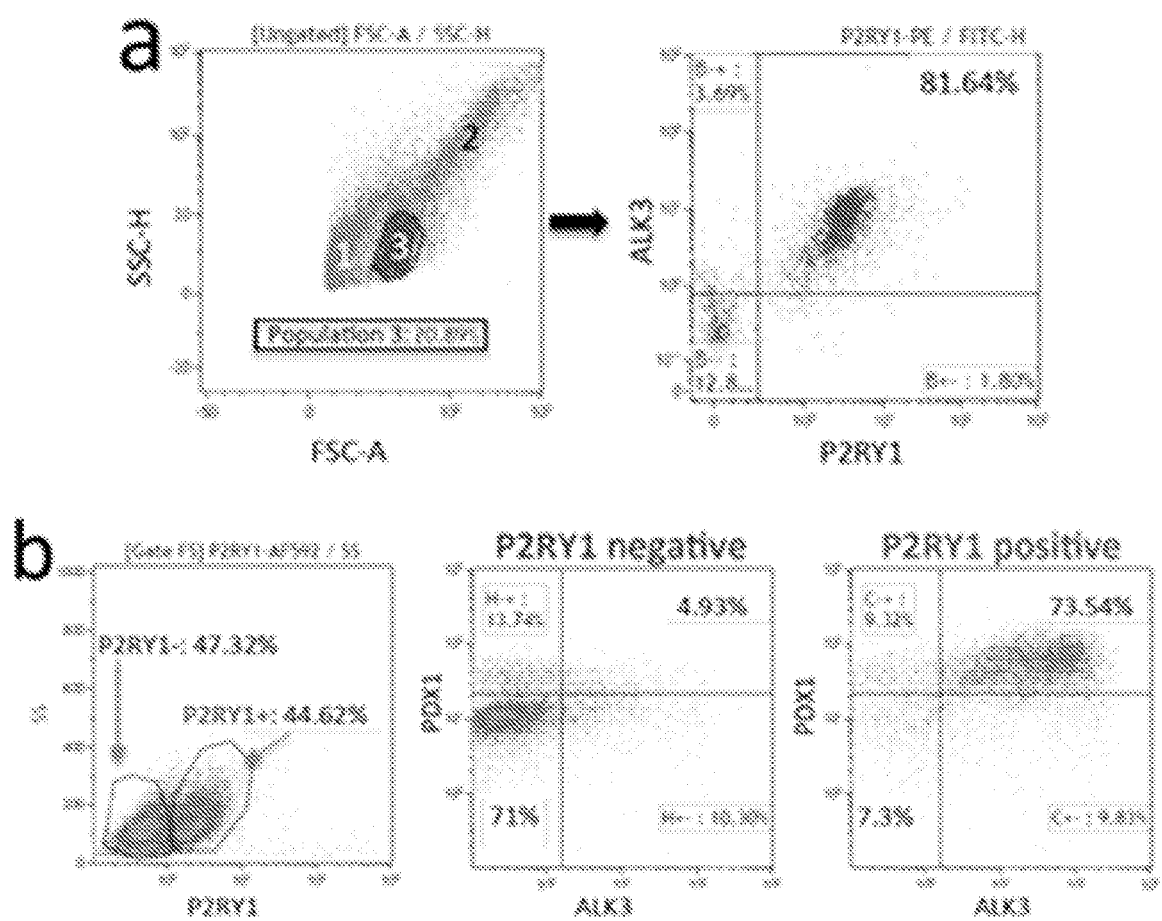
FIG. 15 depicts results of sorting P2RY1 alongside ALK3+ cells in fresh hNEPT preparations.

P2RY1 was tested alongside ALK3 in fresh hNEPT preparations. One of the three cell subpopulations is 81% enriched in ALK3+/P2RY1+ cells. Moreover, results of additional experiments showed that P2RY1 sorting alone results in a very significant enrichment (>73%) in cells that are both ALK3+ and PDX1+ (FIG. 15B). Therefore, sorting by ALK3+/P2YR1+ ensures the isolation of ALK3+/PDX1+ cells. However, as most ALK3+ cells within the exocrine pancreas have been shown to be PDX1+ by IF quantification, and P2RY1 is a PDX1 surrogate, we expect this approach to yield results comparable to those shown in FIG. 15.

Both RIP-Cre and PDX1-Cre are shuttled aboard adenoviruses, and exhibit similar transduction efficiencies. Adenoviruses still express the cassette when the GFP tagging of C-peptide+ cells is examined at day 12 confirming that tagging may occur after differentiation. Every new β-cell reactivates both PDX1 and RIP. If the vector is still present within the cell, it invariably tags the cell after differentiation, rendering the approach useless. However, the observation that the proportion of C-peptide+ cells tagged with PDX1-Cre is 3-fold higher than that observed with RIP-Cre[17] proves that tagging does occur prior to β-cell differentiation. Otherwise, similar tagging percentages are expected with both cassettes.

Results are consistent with the hypothesis that extrainsular progenitor-like cells are major contributors to newly formed insulin+ cells by BMP-7. The histological distribution of non-endocrine PDX1+ cells in the human pancreas strongly suggests a ductal residence. The PDX1+/ALK3+ cells within ductal structures do not always express the ductal marker CAII[19]. In fact, the cells with strongest ALK3 expression (those of the MPD) are shown to be largely CAII− by IF. This observation is aligned with the lineage tracing data, which do not indicate a significant contribution of CAII+ cells to new β-like cells after BMP-7 exposure, and additionally suggest that PDX1+/ALK3+/CAII− is the phenotype of the cells that respond to the treatment.

Example 8

Characterization of hNEPT Resident Progenitor-Like Cells

The data provided in Examples 1-7 suggests that C-peptide+ cells induced by BMP-7 arise predominantly from hNEPT-resident PDX1+/ALK3+ cells. These cells may be further characterized at the molecular level.

A 2-color FACS selection for dissociated hNEPT (as well as collagenase-digested MPDs) that are positive for the surface markers P2RY1 and ALK3 (Life Span Biosciences) is conducted. This approach has already been successfully tested, as is shown herein.

Before proceeding to the next step, demonstration that the sorted populations respond to BMP-7 is preferred. The identity of sorted cells is confirmed by IF, and aliquots are cultured in adherent conditions. Single sorted pancreatic cells are notoriously difficult to culture in plastic, which is addressed by using a combination of Matrigel®-coated plates and fully defined media [STEMPRO® (Thermofisher Scientific, Grand Island, N.Y.) or Kubota's Medium® (PhoenixSongs Biologicals Branford, Conn.)][8,29,48,49] Matrigel® is used to grow multipotent pancreatic cells[50,51]. Colonies from dissociated ALK3+ cells sorted from fresh hNEPT are readily grown in these conditions, and resemble those obtained from the MPD without sorting. The typical "ring" morphology described by others[50,51] is observed when plating ALK3+ cells in 3D conditions or fibroblast feeder cells. Preliminary qRT-PCR experiments conducted on ALK3+-sorted cells show that only the ALK3+ fraction is BMP-7-responsive ($10^3$-fold increase in insulin expression vs. non-BMP-7 treated controls), confirming the earlier results with magnetic bead enrichment. The ALK3− fraction did not show any response to BMP-7.

Aliquots are analyzed upon sorting (baseline measurement) by real-time qRT-PCR using custom-made Taqman®-based Low Density Array cards (TLDAs) for the analysis of >40 pancreatic/β-cell markers as well as by direct IF of a panel of 15 pancreatic/islet markers. The relative insulin expression by qRT-PCR in P2RY1+/ALK3+ cells obtained from hNEPT vs. insulin+ cells sorted from purified islets (positive control) and other exocrine (acinar & P2RY1+/ALK3− ductal cells) cell types as negative controls is analyzed. These analyses shed additional light on the question of whether putative progenitor cells may express low insulin levels Sorted cells are treated with 100 ng/μl of BMP-7 with or without dorsomorphin, which inhibits BMP signaling. Additional aliquots receive no treatment. BMP-7 induces the expression of endocrine differentiation genes vs. control (no treatment) or simultaneous BMP-7+dorsomorphin treatment. This is determined by qRT-PCR and IF as above, as well as ultrastructural analyses by TEM.

For proliferation studies, EdU (5-ethynyl-2'-deoxyuridine) is added to aliquots of every group to determine cell division rates before and during BMP-7 treatment (data points to be analyzed: days 2, 4, 6, 8, 10 and 12). Co-localization of EdU with ALK3, PDX1, CAII, C-peptide, glucagon and combinations thereof are studied by IF. Real-time proliferation within BMP-7-induced colonies using a lentiviral Ki67-GFP construct is also analyzed. Collectively, results of experiments described herein help determine whether sorted P2RY1+/ALK3+ cells recapitulate the BMP-7-induced β-cell differentiation observed from unfractionated hNEPT, while providing an experimental model in which differentiation and proliferation potential in the absence of other potentially confounding cell types (including residual β-cells) is observed.

Example 9

Determination of Multilineage Differentiation

More comprehensive lineage tracing studies are described herein to determine the full differentiation potential of BMP-7-responsive cells. PDX1-Cre and ALK-Cre tagging are also found in glucagon-expres sing cells after BMP-7 treatment of hNEPT. This is consistent with experiences with biliary tree progenitors (which become either pancreatic or hepatic cell types depending on specific extracellular matrix cues[8]), as well as with the reported multipotency of other putative pancreatic progenitor-like cells described in the literature[46,47,50]. The lineage-tracing design is based on the use of lentivirus for the reporter and adenovirus for PDX1-Cre, ALK3-Cre, Elas3a-Cre, CAII-Cre and RIP-Cre. This system is used to further ascertain the origin of the entire gamut of endocrine and exocrine cell types after BMP-7 treatment.

Live cells sorted according to the above criteria (P2RY1$^+$ and ALK3$^+$) may contain a mix of BMP-7-responsive and non-responsive cells. In particular, while devoid of β-cells (which are ALK3$^-$), these preps contain both CAII$^-$ and CAII$^+$ cells.

The P2RY1$^+$/ALK3$^+$/CAII$^-$ fraction is BMP-7-responsive based on our lineage tracing data that CAII$^+$ cells do not contribute to new β-like cell generation[17] and the observation that the cells with the highest ALK3 expression within the pancreas correspond to a newly described ductal population characterized by the absence of CAII expression. Negative results for CAII are obtained using two lentiviral vectors (for the reporter and the tracer). In contrast, positive results for PDX1-Cre and ALK3-Cre are observed using a lentivirus for the reporter and an adenovirus for the tracer. Further experiments may be desired to repeat CAII-Cre lineage tracing using the same conditions previously used for PDX1-Cre and ALK3-Cre, i.e., a lentivirus for the reporter and an adenovirus for CAII-Cre. RNA-seq of both P2RY1$^+$/ALK3$^+$/CAII$^+$ and P2EY1$^+$/ALK3$^+$/CAII$^-$ subpopulations is performed. Distinctive surface markers for each, are used to sort live cells and determine their β-cell generation potential after culture with BMP-7. Based on results described herein, P2RY1$^\pm$/ALK3$^{bright+}$ fractions are largely CAII, so similar experiments are designed to use P2RY1$^+$/ALK3$^{bright+}$ vs. P2RY1$^+$/ALK3$^{low}$.

Figure 16:
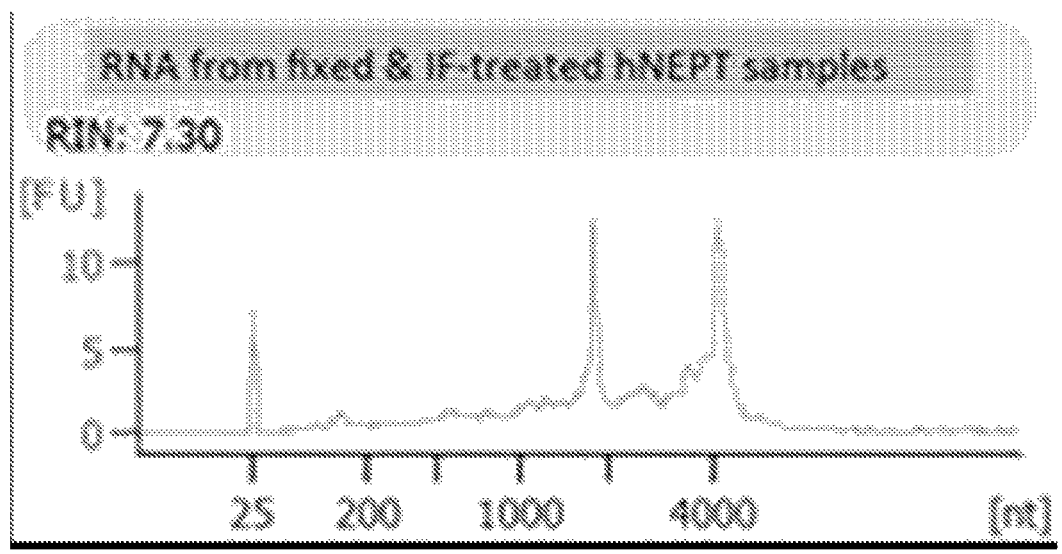
FIG. 16 depicts RNA obtained from fixed and IF treated hNEPT samples.

The generation of high-quality RNA for transcription profiling following fixation, intracellular IF staining and FACS is described[52] and termed MARIS (Method for Analyzing RNA following Intracellular Sorting). The RNA obtained from fixed samples is of high quality (RIN: 7.3, within the range reported in[52]; see FIG. 16). Further assessment of the level of expression of four genes (amylase, PDX1, ALK3 and CAII) in fresh hNEPT samples (control) or hNEPT that are subjected to the fixing conditions (for ALK3 and CAII) used in IF is performed. Hexa-random primers for the RT step of qRT-PCR, as in the Illumina protocol to be used for RNA-seq is employed. There are no statistically significant differences between fixed and control samples. MARIS allows the use of CAII (an intracellular marker) to separate P2RY1$^+$/ALK3$^+$/CAII from P2RY1$^+$/ALK3$^+$/CAII$^+$ populations for all the RNA-seq analyses above.

Example 10

Development of a Surgical Model for In Vivo generation of insulin$^+$ Cells from hNEPT or Sorted PR2Y1$^+$/ALK3$^+$ Cells by Local BMP-7 Delivery The nude rat (RNU, Crl:NIH-Foxn1$^{rnu}$) is chosen over mice due to the specific BMP-7 local delivery system designed for this purpose, requiring surgical procedures for which a larger animal size would be beneficial. As stated before, the demonstration that resident progenitor-like cells within the pancreas are activated in situ through a non-genetic intervention with a single, FDA-approved compound may open the door to innovative therapies. Although BMPs and BMP receptor agonists possess an excellent safety profile even when given systemically ([53,18,67-69] and Phase II trials with THR-184, clinicaltrials.gov identifier NCT01830920), this research design uses local delivery. The kidney sub-capsular space of rodents is a well-established ectopic site for pancreatic cell (and particularly islet) transplantation[54,55]. There are reports of success in the continuous delivery of compounds to pancreatic cells previously implanted under the kidney capsule of rats[38] using Alzet® osmotic pumps that release solution at a rate of 0.5 µl/h for 2 weeks.

While exocrine and endocrine cells coexist in the pancreas, cultured hNEPT lack native ECM for proper compartmentalization, and acinar secretions may be harmful for endocrine cells[37]. Acinar cells present in hNEPT after BMP-7 treatment persist in grafts[17]. This observation was hypothesized to be one reason behind the sub-optimal performance of BMP-7-treated hNEPT in vivo (see Example 2). However, diabetes reversal is not a condition to demonstrate that hNEPT can give rise to insulin$^+$ cells in vivo. The first phase of these studies transplants unfractionated hNEPT (0.5-1×10$^7$ cells) previously grown for 48h in attachment (prior to BMP-7 treatment) under the kidney capsule of nude rats. This process is known to give rise to C-peptide$^+$ cells upon BMP-7 exposure in vitro (as described in prvious Examples). BMP-7 is delivered for 14d through a catheter connected to a subcutaneous Alzet® pump. Since reconstituted BMP-7 is active for only 2-7 days[56], iPRECIO® osmotic pumps are used, which allow solutions inside to be exchanged or replenished via percutaneous access to a re-sealable septum in the live animal. This feature enables the pumps to be refilled with fresh BMP-7 solution every 2 days, which results in local BMP-7 concentrations similar to those observed in the in vitro experiments described herein. Controls are transplanted with the same amount of cells but their pumps will contain saline instead of BMP-7. A single hNEPT preparation and five animals/group is used. Rats are euthanized at POD +21 and their grafts analyzed by IF for C-peptide as well as the 15 pancreatic marker panel of Example 8. Substantial in vivo β-like cell formation compared to controls is detected.

The second phase entails the transplantation of PR2Y1$^+$/ALK3$^+$ cells sorted from fresh hNEPT. While the formation of neo-acinar tissue from these cells is a possibility (see Example 8), this setting (as opposed to full hNEPT) prevents the carry-over of pre-existing acinar cells into the graft. Sorting is done by PR2Y1$^+$/ALK3$^+$. The experimental design is as above, i.e., an iPRECIO® pump is used to deliver either BMP-7 or saline. Ten animals/group are used for each PR2Y1$^+$/ALK3$^+$ prep (n=3). Fresh solutions are used to refill every three days. Animals are followed up for up to 90 days. Human C-peptide measurements and intraperitoneal glucose tolerance tests (IPGTT) are done periodically to indirectly determine whether (3-cell conversion is taking place within the graft. The pro-insulin/insulin (PI/I) ratio during IPGTT is calculated, as this plasma measurement provides an estimate for the PI/I ratio within secretory granules after acute stimulation of insulin secretion[57], which can be used as an indirect measurement of β-cell potency[58, 59]. PI/I ratios of PR2Y1$^+$/ALK3$^+$ cell-transplanted animals (after in situ treatment with BMP-7) are compared with those of immunodeficient rats transplanted with human islets (as positive controls). Five animals within each group will receive BrdU in the water for the further analyses.

The five rats/group receiving BrdU are sacrificed at POD +21 for IF characterization of the graft. Markers that are examined by IF include BrdU (to assess cumulative proliferation) and TUNEL & activated caspase-3 (apoptosis). Co-localization experiments with C-peptide, PDX1, CAII/CA-19.9/CK-19 (for ductal cells) and amylase/CPA (for acinar cells) are conducted as well as a thorough analysis of graft composition, by looking at the abundance/relative proportion and histological distribution of hormone-producing cells as well as other acinar and ductal cell types by ImageJ analysis. Furthermore, the determination of whether insulin, PDX1, C-peptide, MAFA and UCN3 are simultaneously expressed (a sign of (γ-cell function) and whether hormones are co-expressed in the same cell (a sign of non-function) is done. The results are interpreted in light of knowledge of islet (β-cell biology. BMP-7-treated animals have abundant islet-like structures within the graft, exhibiting proliferation (anti-BrdU staining in C-peptide$^+$ cells). These structures are absent or near undetectable in controls that received no BMP-7.

The remaining animals are followed up for 90 days. Rats in which consistent human C-peptide production is established are treated with streptozotocin (stz) to induce selective destruction of their pancreatic β-cells. If stz-resistant human β-cells prevent diabetes induction, nephrectomy of the graft-bearing kidney result in hyperglycemia. Grafts and pancreata from such animals are retrieved for IF analysis. All remaining animals are humanely euthanized by POD +90 and analyzed as above.

Example 11

Determination of In Situ β-Cell Regeneration

Indirect data consistent with the hypothesis that BMP-7 may induce β-cell regeneration is reported in a model of cardiac regeneration. Mice rendered hyperglycemic with stz exhibited less adverse prediabetes-related cardiac remodeling when systemically treated with BMP-7[65]. While that study focused only on the heart, BMP-7 also corrected the hyperglycemia of stz-treated mice. BMP-7 may achieve that effect by mechanisms other than resident progenitor-like cell stimulation. These include (3-cell proliferation mediated by M2 macrophages[66] (as BMP-7 is a monocyte-M2 polarizing agent[67]) or even peripheral effects that are largely islet-independent (such as BMP-mediated improvement of glucose metabolism or brown adipogenesis[68]). The development of a mouse model allows for the study of all these possibilities. However, the primary objective is to test whether systemic administration of BMP-7 (or small molecule agonists of the ALK3 receptor, such as THR-123) results in new (3-cell formation in the pancreas of stz-treated diabetic mice.

Systemic BMP-7 (500 μg/kg) is administered to CD1 mice by means of intraperitoneal (IP) injection daily for 30 days. This dose is within the range reported for rodents in other BMP administration settings[18,67-69], and is refined in subsequent preclinical experiments. Acute diabetes is induced by a single injection of stz (200 mg/kg) prior to BMP-7 treatment. Controls receive saline by the same route. This generates evidence that accumulation of FITC-labeled THR-123 (at doses that are equimolar to those calculated for BMP-7 above) is detectable in the parenchyma and ductal structures of the pancreas 2 hours after IP injection (FIG. 22). Similar doses[18] are effective at reversing kidney fibrosis. Ten animals/group are used. Half of the animals in each group receive BrdU in the water. Mice are euthanized 30 days after initiation of treatment, or earlier if diabetes reversal is observed. Glycemia is monitored daily at the same time, right before injection. IPGTTs and determination of PI/I ratios is done at 14 and 30 days. Upon euthanasia, the pancreas and other organs are harvested and analyzed by a pathologist to establish if there are tumorigenic or otherwise toxic effects associated with the treatment. The pancreas is also studied by IF in search of potential β-cell/endocrine cell neogenesis and/or signs of β-cell/endocrine cell proliferation (BrdU-treated animals) when compared to saline-treated controls. Such signs, if present, are studied in their anatomical context, and in conjunction with other relevant markers of the pancreatic panel. Relative quantification of β-cell/endocrine cell neogenesis are done using normalized total insulin quantification and the imaging techniques described in Example 4 and[17]. Tissue/blood samples for the analysis of peripheral and pancreatic resident macrophage populations by IF are saved, as well as brown fat content/distribution. Based on preliminary data and those reported in[65], the glycemic improvements in the BMP-7 group vs. controls, potentially associated with a significant degree of reconstitution of the endocrine compartment is detected.

Example 12

Administration of THR-123 Decreased Hyperglycemia In Vivo

Next, THR-123 was injected daily for 23 d, followed by an additional 7 d without treatment. Controls received saline by the same route. Preliminary results show drastic decreases in hyperglycemia in THR-123-treated mice vs. controls, especially after the withdrawal of THR-123 (FIG. 17). The latter is consistent with the in vitro studies on hNEPT described herein, which show BMP-7-dependent expansion of progenitors followed by maturation after BMP-7 withdrawal.

REFERENCES OR EXAMPLES 1-5

1. Ricordi C, Strom T B. *Nat Rev Immunol.* 2004; 4:259-268.
2. Poggioli R, Faradji R N, Ponte G, et al. Am J Transplant. 2006; 6:371-378.
3. Zhou Q, Brown J, Kanarek A, et al. *Nature.* 2008; 455:627-632.
4. Lee J, Sugiyama T, Liu Y, et al. *eLife.* 2013; 2:e00940.
5. Li W, Cavelti-Weder C, Zhang Y, et al. *Nat Biotechnol.* 2014.
6. Li W, Nakanishi M, Zumsteg A, et al. *eLife.* 2014; 3:e01846.
7. Lima M J, Muir K R, Docherty H M, et al. *Diabetes.* 2013; 62:2821-2833.
8. Lemper M, Leuckx G, Heremans Y, et al. *Cell Death Differ.* 2014.
9. Bonner-Weir S, Baxter L A, Schuppin G T, et al. Diabetes. 1993; 42:1715-1720.
10. Bonner-Weir S, Inada A, Yatoh S, et al. *Biochem Soc Trans.* 2008; 36:353-356.
11. Bonner-Weir S, Toschi E, Inada A, et al. *Pediatr Diabetes.* 2004; 5 Suppl 2:16-22.
12. Wang Y, Lanzoni G, Carpino G, et al. *Stem Cells.* 2013; 31:1966-1979.
13. Edlund H. *Diabetes.* 1998; 47:1817-1823.
14. Ahlgren U, Jonsson J, Jonsson L, et al. *Genes Dev.* 1998; 12:1763-1768.
15. Edlund H. *Nat Rev Genet.* 2002; 3:524-532.

16. Zeisberg M, Hanai J, Sugimoto H, et al. *Nat Med.* 2003; 9:964-968.
17. Cheifetz S, Li I W, McCulloch CvA, et al. *Connect Tissue Res.* 1996; 35:71-78.
18. Jiang F X, Stanley E G, Gonez U, et al. *J Cell Sci.* 2002; 115:753-760.
19. Wandzioch E, Zaret K S. *Science.* 2009; 324:1707-1710.
20. Chung W S, et al. *Proc Natl Acad Sci USA.* 2010; 107:1142-1147.
21. Sui L, Geens M, Sermon K, et al. *Stem Cell Rev.* 2013.
22. Sugimoto H, LeBleu V S, Bosukonda D, et al. *Nat Med.* 2012; 18:396-404.
23. Sugimoto H, Yang C, LeBleu V S, et al. *FASEB J.* 2007; 21:256-264.
24. Yasmin N, Bauer T, Modak M, et al. *J Exp Med.* 2013; 210:2597-2610.
25. Miyazono K, et al. *Cytokine Growth Factor Rev.* 2005; 16:251-263.
26. ten Dijke P, et al. *J Biol Chem.* 1994; 269:16985-16988.
27. Szabat M, Pourghaderi P, Soukhatcheva G, et al. *Islets.* 2011; 3:175-187.
28. Smukler Simon R, et al. *Cell Stem Cell.* 2011; 8:281.
29. Ivka Afrikanova A K, et al. BioResearch Open Access. 2012; 1:184-191.
30. Inada A, Nienaber C, Fonseca S, et al. *Dev Dyn.* 2006; 235:1571-1577.
31. Baeyens L, Lemper M, Leuckx G, et al. *Nat Biotechnol.* 2013.
32. Hammer R E, Swift G H, Ornitz D M, et al. *Mol Cell Biol.* 1987; 7:2956-2967.
33. Rose S D, MacDonald R J. *Hum Mol Genet.* 1997; 6:897-903.
34. Kim M S, Pinto S M, Getnet D, et al. *Nature.* 2014; 509:575-581.
35. Furuyama K, Kawaguchi Y, Akiyama H, et al. *Nat Genet.* 2011; 43:34-41.
36. Kopp J L, Dubois C L, Schaffer A E, et al. *Development.* 2011; 138:653-665.
37. Kawaguchi Y. *J Clin Invest.* 2013; 123:1881-1886.
38. Singh J A. *BMC Med.* 2012; 10:44.
39. Hunter D J, et al. *BMC musculoskeletal disorders.* 2010; 11:232.
40. Corritore E, et al. *Cellular reprogramming.* 2014; 16:456-466.
41. Bonner-Weir S, et al. *Proc Natl Acad Sci USA.* 2000; 97:7999-8004.
42. Edlund H. *Diabetes.* 2001; 50 Suppl 1:S5-9.
43. Chen D, Zhao M, Harris S E, et al. *Front Biosci.* 2004; 9:349-358.
44. Goulley J, Dahl U, Baeza N, et al. *Cell Metab.* 2007; 5:207-219.
45. Talchai C, Xuan S, Lin H V, et al. *Cell.* 2012; 150:1223-1234.
46. Seaberg R M, Smukler S R, Kieffer T J, et al. *Nat Biotech.* 2004; 22:1115.
47. Baeyens L, Bouwens L. *Diabetes Obes Metab.* 2008; 10 Suppl 4:170-178.
48. D'Amour K A, Bang A G, Eliazer S, et al. *Nat Biotechnol.* 2006; 24:1392-1401.
49. Kroon E, Martinson L A, Kadoya K, et al. *Nat Biotechnol.* 2008; 26:443-452.
50. Rezania A, Bruin J E, Arora P, et al. *Nat Biotechnol.* 2014.
51. Pagliuca F W, Millman J R, Gurtler M, et al. *Cell.* 2014; 159:428-439.
52. Loganathan G, et al. *Transplantation.* 2011; 92:1222-1230.
53. Ricordi C, Lacy P E, Finke E H, et al. *Diabetes.* 1988; 37:413-420.
54. Gannon M, Gamer L W, Wright C V. *Dev Biol.* 2001; 238:185-201.
55. Szabat M, Luciani D S, Piret J M, et al. *Endocrinology.* 2009; 150:1627-1635.

REFERENCES FOR EXAMPLES 6-12

1. Ricordi, C. & Strom, T. B., *Nat Rev Immunol,* 2004; 4:259-68.
2. Poggioli, R., Faradji, R. N., et al. *Am J Transplant,* 2006; 4:371-378.
3. Zhou, Q., Brown, J., et al. *Nature,* 2008; 455:627-32.
4. Lee, J., Sugiyama, T., Liu, et al. *Elife* 2; 2013; e00940.
5. Bonner-Weir, S., Baxter, L. A., et al. *Diabetes,* 1993; 42:1715-20.
6. Bonner-Weir, S., Inada, A., et al. *Biochem Soc Trans.* 2008; 36:353-6.
7. Bonner-Weir, S., Toschi, E., et al. *Pediatr Diabetes,* 2004; 5 Suppl 2:16-22.
8. Wang, Y., Lanzoni, G., et al. *Stem Cells,* 2013; 31:1966-79.
9. Zeisberg, M., Hanai, J., et al. *Nat Med,* 2003; 9:964-968.
10. Cheifetz, S., Li, LW., et al. *Connect Tissue Res,* 1996; 35:71-78.
11. Jiang, F. X., Stanley, E. G., et al. *J Cell Sci,* 2002; 115:753-60.
12. Wandzioch, E. & Zaret, K. S., *Science,* 2009; 324:1707-1710.
13. Chung, W. S., Andersson, O., et al. Proc Natl Acad Sci USA, 2010; 107:1142-1147.
14. Sui, L., Geens, M., et al. *Stem Cell Rev* (2013).
15. Chen, D., Zhao, M., et al. *Front Biosci,* 2004; 9:349-58.
16. Kayton, N. S., et al. *Am J Physiol Endocrinol Metab,* 2015; 308:E592-602.
17. Klein, D., Alvarez-Cubela, S., et al. Diabetes, 2015; 64:4123-4134.
18. Sugimoto, H., LeBleu, V. S., et al. Nat Med, 2012; 18:396-404.
19. Inada, A., Nienaber, C., et al. *Dev Dyn,* 2006; 235:1571-7.
20. Singh, J. A., *BMC Med,* 2012; 10:44.
21. Hunter, D. J., Pike, M. C., et al. *BMC Musculoskelet Disord,* 2010; 11:232.
22. Bravo-Egana, V., Rosero, S., et al. Biochem Biophys Res Commun, 2008; 366:922-6.
23. Dominguez-Bendala, J., et al. *Cold Spring Harb Protoc,* 2012: 962-8.
24. Dominguez-Bendala, J., et al. *Diabetes,* 2013; 62:694-5.
25. Klein, D., Misawa, R., et al. *PLoS One;* 2013; 8:e55064.
26. Nieto, M., Hevia, P., Garcia, E., et al. *Cell Transplant,* 2011.
27. Dominguez-Bendala, J., Klein, D., et al. *Diabetes,* 2005; 54:720-6.
28. Vargas, N., Alvarez-Cubela, S., et al. *PLoS One,* 2011; 6:e22364.
29. Cardinale, V., Wang, Y., et al. *Hepatology,* 2011; 54:2159-72.
30. Dominguez-Bendala, J., Lanzoni, G., et al. *Trends Endocrinol Metab* (2016).
31. Lemper, M., Leuckx, G., Heremans, Y., et al. *Cell Death Differ,* 2015; 22:1117-30.
32. Lima, M. J., Muir, K. R., et al. *Diabetes,* 2013; 62:2821-33.
33. Baeyens, L., Lemper, M., et al. *Nat Biotechnol,* 2013; 32:76-83.

34. Yatoh, S., Dodge, R., et al. *Diabetes,* 2007; 56:1802-9.
35. Herrera, B. & Inman, G. J., *BMC Cell Biol,* 2009; 10:20.
36. Pileggi, A., Molano, R. D., Berney, T., et al. *Diabetes,* 2001; 50:1983-91.
37. Loganathan, G., Dawra, R. K., et al. *Transplantation,* 2011; 92:1222-30.
38. Russ, H. A., Ravassard, P., et al. *PLoS ONE,* 2009; 4:e6417.
39. Miyazono, K., Maeda, S. et al. *Cytokine Growth Factor Rev,* 2005; 16:251-63.
40. Sugimoto, H., Yang, C., et al. *FASEB J,* 2007; 21:256-64.
41. Yasmin, N., Bauer, T., et al. *J Exp Med,* 2013; 210:2597-610.
42. Dorrell, C., Schug, J., et al. *Diabetologia,* 2011; 54:2832-44.
43. Russ, H. A., Bar, Y., et al. *Diabetes,* 2008; 57:1575-83.
44. Gu, G., Brown, J. R. et al. *Mech Dev,* 2003; 120:35-43.
45. Talchai, C., Xuan, S., et al. *Cell,* 2012; 150:1223-34.
46. Seaberg, R. M., Smukler, S. R., et al. *Nat Biotech,* 2004; 22:1115.
47. Smukler, Simon R., Arntfield, Margot E., et al. *Cell Stem Cell,* 2011; 8:281-293.
48. Kubota, H. & Reid, L. M., *Proc Natl Acad Sci USA,* 2000; 97:12132-7.
49. Cardinale, V., Wang, Y., et al. *Nat Rev Gastroenterol Hepatol,* 2012; 9:231-40.
50. Jin, L., Gao, D., et al. *Stem Cell Res,* 2015; 16:40-53.
51. Jin, L., Feng, T., et al. *Proc Natl Acad Sci USA,* 2013; 110:3907-12.
52. Hrvatin, S., Deng, F., et al. *PLoS One,* 2014; 9:e89459.
53. Vukicevic, S., Sampath, Kuber (Eds.). 339, 2008.
54. Pileggi, A., Klein, D., Fotino, C., et al. *Immunol Res,* 2013; 57:185-96.
55. Cechin, S., Alvarez-Cubela, S., et al. *Stem Cells Transl Med,* 2014; 3:277-89.
56. ProSpec-Tany-Technogene. Human recombinant BMP-7 manufacturer's brochure.
57. Fritsche, A., Madaus, A., et al. *Diabetes,* 2002; 51 Suppl 1:S234-9.
58. Larsson, H. & Ahren, B., *J Clin Endocrinol Metab,* 1999; 84:2068-74.
59. Roder, M. E., Porte, D., Jr., et al. *J Clin Endocrinol Metab,* 1998; 83:604-8.
60. Song, Y., Margolles-Clark, E., et al. *Pharmazie,* 2012; 67:394-9.
61. Pedraza, E., Brady, A. C., et al. *Cell Transplant,* 2012.
62. Buchwald, P., Bocca, N., et al. *Pharmazie,* 2010; 65:421-8.
63. Pileggi, A., Molano, R. D., et al. *Transplantation,* 2006; 81:1318-24.
64. Bruun, C., Christensen, G. L., et al. *Diabetologia,* 2014; 57:2546-54.
65. Urbina, P. & Singla, D. K., *Am J Physiol Heart Circ Physiol,* 2014; 307:H762-72.
66. Xiao, X. & Gittes, G. K., *Stem Cells Transl Med,* 2015; 4:655-8.
67. Rocher, C. & Singla, D. K., *PLoS One,* 2013; 8:e84009.
68. Kuo, M. M., Kim, S., et al. *Biomaterials,* 2014; 35:3172-9.
69. Corradini, E., Schmidt, P. J., et al. *Gastroenterology,* 2010; 139:1721-9.
70. Maric, I., et al *Am J Physiol Gastrointest Liver Physiol,* 2012; 302:G1151-62.
71. Claudia Cavelti-Weder, W. L., Adrian Zumsteg, et al *Diabetologia* 2016; 59:522-532.

TABLE 1

Summary of SEQ ID NOS:

| SEQ ID NO | Description | Sequence |
|---|---|---|
| 1 | full length human mature chain of BMP-7 (NCBI Reference Sequence: NM_001719.2) | MHVRSLRAAAPHSFVALWAPLFLLRSALADFSLD NEVHSSFIHRRLRSQERREMQREILSILGLPHRP RPHLQGKHNSAPMFMLDLYNAMAVEEGGGPGGQG FSYPYKAVFSTQGPPLASLQDSHFLTDADMVMSF VNLVEHDKEFFHPRYHHREFRFDLSKIPEGEAVT AAEFRIYKDYIRERFDNETFRISVYQVLQEHLGR ESDLFLLDSRTLWASEEGWLVFDITATSNHWVVN PRHNLGLQLSVETLDGQSINPKLAGLIGRHGPQN KQPFMVAFFKATEVHFRSIRSTGSKQRSQNRSKT PKNQEALRMANVAENSSSDQRQACKKHELYVSFR DLGWQDWIIAPEGYAAYYCEGECAFPLNSYMNAT NHAIVQTLVHFINPETVPKPCCAPTQLNAISVLY FDDSSNVILKKYRNMVVRACGCH |
| 2 | human mature chain of BMP-7 (NCBI Reference Sequence: NM_001719.2) comprising peptide from 293-431 | IRSTGSKQRSQNRSKTPKNQEALRMANVAENSSS DQRQACKKHELYVSFRDLGWQDWIIAPEGYAAYY CEGECAFPLNSYMNATNHAIVQTLVHFINPETVP KPCCAPTQLNAISVLYFDDSSNVILKKYRNMVVR ACGCH |
| 3 | fragment of BMP-4 | SPKHHSQRARKKNKNCRRHSLYVDFSDVGWNDWI VAPPGYQAFYCHGDCPFPLADHLNSTNHAIVQTL VNSVNSSIPKACCVPTELSAISMLYLDEYDKVVL KNYQEMVVEGCGCR |

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for increasing insulin production in a mammal suffering from insulin deficiency comprising: administering a molecule that activates a BMP-7 receptor to said mammal, wherein the molecule that activates a BMP-7 receptor is THR-123, BMP-7, BMP-4, or an active variant or fragment thereof.

2. The method of claim 1, wherein the molecule that activates a BMP-7 receptor is BMP7.

3. The method of claim 1, wherein the molecule that activates a BMP-7 receptor is BMP-4.

4. The method of claim 1, wherein the molecule that activates a BMP-7 receptor is THR-123.

5. A method for treating type 1 diabetes in a mammal comprising: administering a molecule that activates a BMP-7 receptor to said mammal, wherein the molecule that activates a BMP-7 receptor is THR-123, BMP-7, BMP-4, or an active variant or fragment thereof.

6. The method of claim 5, wherein the molecule that activates a BMP-7 receptor is BMP-7.

7. The method of claim 5, wherein the molecule that activates a BMP-7 receptor is BMP-4.

8. The method of claim 5, wherein the molecule that activates a BMP-7 receptor is THR-123.

* * * * *

```
                         SEQUENCE LISTING

<160> NUMBER OF SEQ ID NOS: 3

<210> SEQ ID NO 1
<211> LENGTH: 431
<212> TYPE: PRT
<213> ORGANISM: Homo sapiens
<220> FEATURE:
<221> NAME/KEY: MISC_FEATURE
<223> OTHER INFORMATION: full length human mature chain of BMP-7

<400> SEQUENCE: 1

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
```

```
                325                 330                 335
Val Ser Phe Arg Asp Leu Gly Trp Gln Asp Trp Ile Ile Ala Pro Glu
        340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
        405                 410                 415

Leu Lys Lys Tyr Arg Asn Met Val Val Arg Ala Cys Gly Cys His
        420                 425                 430

<210> SEQ ID NO 2
<211> LENGTH: 141
<212> TYPE: PRT
<213> ORGANISM: Homo sapiens
<220> FEATURE:
<221> NAME/KEY: MISC_FEATURE
<223> OTHER INFORMATION: human mature chain of BMP-7 (NCBI Reference
      Sequence: NM_001719.2) comprising peptide from 293-431

<400> SEQUENCE: 2

Ile Arg Ser Thr Gly Ser Lys Gln Arg Ser Gln Asn Arg Ser Lys Thr
1               5                   10                  15

Pro Lys Asn Gln Glu Ala Leu Arg Met Ala Asn Val Ala Glu Asn Ser
            20                  25                  30

Ser Ser Asp Gln Arg Gln Ala Cys Lys Lys His Glu Leu Tyr Val Ser
        35                  40                  45

Phe Arg Asp Leu Gly Trp Gln Asp Trp Ile Ile Ala Pro Glu Gly Tyr
    50                  55                  60

Ala Ala Tyr Tyr Cys Glu Gly Glu Cys Ala Phe Pro Leu Asn Ser Tyr
65                  70                  75                  80

Met Asn Ala Thr Asn His Ala Ile Val Gln Thr Leu Val His Phe Ile
                85                  90                  95

Asn Pro Glu Thr Val Pro Lys Pro Cys Cys Ala Pro Thr Gln Leu Asn
            100                 105                 110

Ala Ile Ser Val Leu Tyr Phe Asp Asp Ser Ser Asn Val Ile Leu Lys
        115                 120                 125

Lys Tyr Arg Asn Met Val Val Arg Ala Cys Gly Cys His
    130                 135                 140

<210> SEQ ID NO 3
<211> LENGTH: 116
<212> TYPE: PRT
<213> ORGANISM: Homo sapiens
<220> FEATURE:
<221> NAME/KEY: MISC_FEATURE
<223> OTHER INFORMATION: fragment of BMP-4

<400> SEQUENCE: 3

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45
```

```
Cys Pro Phe Pro Leu Ala Asp His Leu Asn Ser Thr Asn His Ala Ile
    50              55                  60
Val Gln Thr Leu Val Asn Ser Val Asn Ser Ser Ile Pro Lys Ala Cys
65              70              75                          80
Cys Val Pro Thr Glu Leu Ser Ala Ile Ser Met Leu Tyr Leu Asp Glu
            85                  90                  95
Tyr Asp Lys Val Val Leu Lys Asn Tyr Gln Glu Met Val Val Glu Gly
            100             105                 110
Cys Gly Cys Arg
        115
```